(12) United States Patent
Cragg et al.

(10) Patent No.: US 10,285,833 B2
(45) Date of Patent: May 14, 2019

(54) STENT DELIVERY SYSTEMS AND ASSOCIATED METHODS

(71) Applicant: Altura Medical, Inc., Palo Alto, CA (US)

(72) Inventors: Andrew H. Cragg, Edina, MN (US); John Logan, Plymouth, MN (US); Nelson Quintana, Temecula, CA (US); Mahmood Dehdashtian, Costa Mesa, CA (US); George Tsai, Mission Viejo, CA (US)

(73) Assignee: Lombard Medical Limited (GB)

( * ) Notice: Subject to any disclaimer, the term of this patent is extended or adjusted under 35 U.S.C. 154(b) by 1276 days.

(21) Appl. No.: 13/964,013

(22) Filed: Aug. 9, 2013

(65) Prior Publication Data

US 2014/0046428 A1    Feb. 13, 2014

Related U.S. Application Data

(60) Provisional application No. 61/681,907, filed on Aug. 10, 2012, provisional application No. 61/799,591, filed on Mar. 15, 2013.

(51) Int. Cl.
*A61F 2/966* (2013.01)
*A61F 2/954* (2013.01)
(Continued)

(52) U.S. Cl.
CPC .............. *A61F 2/966* (2013.01); *A61F 2/954* (2013.01); *A61F 2002/067* (2013.01); *A61F 2002/9517* (2013.01)

(58) Field of Classification Search
CPC .... A61F 2/95; A61F 2/954; A61F 2002/9517; A61F 2/2436
(Continued)

(56) References Cited

U.S. PATENT DOCUMENTS 4,562,596 A    1/1986    Kornberg
4,655,771 A    4/1987    Wallsten
(Continued)

FOREIGN PATENT DOCUMENTS

CN    1248157 A    3/2000
CN    1272053      11/2000
(Continued)

OTHER PUBLICATIONS

Australian Patent Examination Report No. 1, Australian Patent Application No. 2009246093; dated Jan. 31, 2014; 4 pages.
(Continued)

*Primary Examiner* — Diane D Yabut
*Assistant Examiner* — Majid Jamialahmadi
(74) *Attorney, Agent, or Firm* — Craig A. Fieschko, Esq.; DeWitt LLP

(57) ABSTRACT

Stent delivery systems and associated methods for delivering stents are disclosed herein. In several embodiments, a handle assembly for delivering a stent from a tubular enclosure can include a first lead screw having a first lead thread of a first pitch and first handedness, a second lead screw having a second lead thread of a second pitch and second handedness different from the first handedness, and a housing defining threads of the first and second pitches. The first lead screw can be in mechanical communication with the tubular enclosure, and the second lead screw can be in mechanical communication with the stent. Upon rotation of a portion of the housing, the housing threads can engage the lead screws so as to induce simultaneous translations of the lead screws in opposite directions. The simultaneous translations are configured to deploy the stent from the tubular enclosure.

51 Claims, 29 Drawing Sheets

(51) Int. Cl.
*A61F 2/95* (2013.01)
*A61F 2/06* (2013.01)

(58) Field of Classification Search
USPC .............................. 623/1.11, 1.12; 606/200
See application file for complete search history.

(56) References Cited

U.S. PATENT DOCUMENTS

| | | | |
|---|---|---|---|
| 4,990,151 A | 2/1991 | Wallsten | |
| 5,078,726 A | 1/1992 | Kreamer | |
| 5,160,341 A | 11/1992 | Brenneman et al. | |
| 5,201,757 A | 4/1993 | Heyn et al. | |
| 5,316,023 A | 5/1994 | Palmaz et al. | |
| 5,360,443 A | 11/1994 | Barone et al. | |
| 5,364,352 A | 11/1994 | Cimino et al. | |
| 5,397,345 A | 3/1995 | Lazarus | |
| 5,415,664 A | 5/1995 | Pinchuk | |
| 5,433,723 A | 7/1995 | Lindenberg et al. | |
| 5,445,646 A | 8/1995 | Euteneuer et al. | |
| 5,464,449 A | 11/1995 | Ryan et al. | |
| 5,476,505 A | 12/1995 | Limon | |
| 5,476,506 A | 12/1995 | Lunn | |
| 5,480,423 A | 1/1996 | Ravenscroft et al. | |
| 5,507,731 A | 4/1996 | Hernandez et al. | |
| 5,507,769 A | 4/1996 | Marin et al. | |
| 5,522,880 A | 6/1996 | Barone et al. | |
| 5,562,724 A | 10/1996 | Vorwerk et al. | |
| 5,571,170 A | 11/1996 | Palmaz et al. | |
| 5,571,171 A | 11/1996 | Barone et al. | |
| 5,571,173 A | 11/1996 | Parodi | |
| 5,575,818 A | 11/1996 | Pinchuk et al. | |
| 5,578,071 A | 11/1996 | Parodi | |
| 5,578,072 A | 11/1996 | Barone et al. | |
| 5,591,195 A | 1/1997 | Taheri et al. | |
| 5,591,228 A | 1/1997 | Edoga | |
| 5,591,229 A | 1/1997 | Parodi | |
| 5,609,627 A | 3/1997 | Goicoechea et al. | |
| 5,626,604 A | 5/1997 | Cottone, Jr. | |
| 5,628,783 A | 5/1997 | Quiachon et al. | |
| 5,628,788 A | 5/1997 | Pinchuk | |
| 5,632,763 A | 5/1997 | Glastra | |
| 5,632,772 A | 5/1997 | Alcime et al. | |
| 5,639,278 A | 6/1997 | Dereume et al. | |
| 5,653,743 A | 8/1997 | Martin | |
| 5,662,606 A | 9/1997 | Cimino et al. | |
| 5,683,450 A | 11/1997 | Goicoechea et al. | |
| 5,683,453 A | 11/1997 | Palmaz | |
| 5,693,084 A | 12/1997 | Chuter | |
| 5,693,087 A | 12/1997 | Parodi | |
| 5,707,376 A | 1/1998 | Kavteladze et al. | |
| 5,713,917 A | 2/1998 | Leonhardt et al. | |
| 5,716,365 A | 2/1998 | Goicoechea et al. | |
| 5,755,734 A | 5/1998 | Richter et al. | |
| 5,755,735 A | 5/1998 | Richter et al. | |
| 5,755,770 A | 5/1998 | Ravenscroft | |
| 5,759,186 A | 6/1998 | Bachmann et al. | |
| 5,776,142 A * | 7/1998 | Gunderson | A61F 2/88 606/108 |
| 5,817,102 A | 10/1998 | Johnson et al. | |
| 5,824,041 A | 10/1998 | Lenker et al. | |
| 5,824,058 A | 10/1998 | Ravenscroft et al. | |
| 5,833,694 A | 11/1998 | Poncet | |
| 5,843,160 A | 12/1998 | Rhodes | |
| 5,855,598 A | 1/1999 | Pinchuk | |
| 5,871,536 A | 2/1999 | Lazarus | |
| 5,888,201 A | 3/1999 | Stinson et al. | |
| 5,897,587 A | 4/1999 | Martakos et al. | |
| 5,904,713 A | 5/1999 | Leschinsky | |
| 5,906,619 A | 5/1999 | Olson et al. | |
| 5,916,263 A | 6/1999 | Goicoechea et al. | |
| 5,928,279 A | 7/1999 | Shannon et al. | |
| 5,968,068 A | 10/1999 | Dehdashtian et al. | |
| 5,984,955 A | 11/1999 | Wisselink | |
| 5,984,964 A | 11/1999 | Roberts et al. | |
| 5,993,481 A | 11/1999 | Marcade et al. | |
| 6,001,125 A | 12/1999 | Golds et al. | |
| 6,004,348 A | 12/1999 | Banas et al. | |
| 6,015,431 A | 1/2000 | Thornton et al. | |
| 6,019,778 A | 2/2000 | Wilson et al. | |
| 6,024,763 A | 2/2000 | Lenker et al. | |
| 6,039,749 A | 3/2000 | Marin et al. | |
| 6,042,589 A | 3/2000 | Marianne | |
| 6,051,020 A | 4/2000 | Goicoechea et al. | |
| 6,053,899 A | 4/2000 | Slanda et al. | |
| 6,060,128 A | 5/2000 | Kim et al. | |
| 6,070,589 A | 6/2000 | Keith et al. | |
| 6,077,296 A | 6/2000 | Shokoohi et al. | |
| 6,090,128 A | 7/2000 | Douglas | |
| 6,090,133 A | 7/2000 | Richter et al. | |
| 6,099,558 A | 8/2000 | White et al. | |
| 6,102,940 A | 8/2000 | Robichon et al. | |
| 6,117,156 A | 9/2000 | Richter et al. | |
| 6,117,167 A | 9/2000 | Goicoechea et al. | |
| 6,120,522 A | 9/2000 | Vrba et al. | |
| 6,126,685 A | 10/2000 | Lenker et al. | |
| 6,129,756 A | 10/2000 | Kugler et al. | |
| 6,146,415 A | 11/2000 | Fitz | |
| 6,156,063 A | 12/2000 | Douglas | |
| 6,162,237 A | 12/2000 | Chan | |
| 6,162,246 A | 12/2000 | Barone | |
| 6,165,213 A | 12/2000 | Goicoechea et al. | |
| 6,168,610 B1 | 1/2001 | Marin et al. | |
| 6,168,616 B1 | 1/2001 | Brown, III | |
| 6,171,277 B1 | 1/2001 | Ponzi | |
| 6,174,330 B1 | 1/2001 | Stinson | |
| 6,179,809 B1 | 1/2001 | Khairkhahan et al. | |
| 6,183,444 B1 | 2/2001 | Glines et al. | |
| 6,183,481 B1 | 2/2001 | Lee et al. | |
| 6,187,036 B1 | 2/2001 | Shaolian et al. | |
| 6,190,360 B1 | 2/2001 | Iancea et al. | |
| 6,197,049 B1 | 3/2001 | Shaolian et al. | |
| 6,200,339 B1 | 3/2001 | Leschinsky et al. | |
| 6,203,550 B1 | 3/2001 | Olson | |
| 6,210,422 B1 | 4/2001 | Douglas | |
| 6,217,609 B1 | 4/2001 | Haverkost | |
| 6,221,102 B1 | 4/2001 | Baker et al. | |
| 6,230,476 B1 | 5/2001 | Carr et al. | |
| 6,231,597 B1 | 5/2001 | Deem et al. | |
| 6,238,402 B1 | 5/2001 | Sullivan, III et al. | |
| 6,261,316 B1 | 7/2001 | Shaolian et al. | |
| 6,267,783 B1 | 7/2001 | Letendre et al. | |
| 6,270,525 B1 | 8/2001 | Letendre et al. | |
| 6,290,731 B1 | 9/2001 | Solovay et al. | |
| 6,302,906 B1 | 10/2001 | Goicoechea et al. | |
| 6,306,141 B1 | 10/2001 | Jervis | |
| 6,306,164 B1 | 10/2001 | Kujawski | |
| 6,306,424 B1 | 10/2001 | Vyakarnam et al. | |
| 6,309,413 B1 | 10/2001 | Dereume et al. | |
| 6,325,819 B1 | 12/2001 | Pavcnik et al. | |
| 6,325,822 B1 | 12/2001 | Chouinard et al. | |
| 6,331,190 B1 | 12/2001 | Shokoohi et al. | |
| 6,331,191 B1 | 12/2001 | Chobotov | |
| 6,344,052 B1 | 2/2002 | Greenan et al. | |
| 6,344,056 B1 | 2/2002 | Dehdashtian | |
| 6,371,963 B1 | 4/2002 | Nishtala et al. | |
| 6,383,193 B1 | 5/2002 | Cathcart et al. | |
| 6,391,033 B2 | 5/2002 | Ryan | |
| 6,391,051 B2 | 5/2002 | Sullivan, III et al. | |
| 6,395,019 B2 | 5/2002 | Chobotov | |
| 6,398,802 B1 | 6/2002 | Yee | |
| 6,398,807 B1 | 6/2002 | Chouinard et al. | |
| 6,409,750 B1 | 6/2002 | Hyodoh et al. | |
| 6,413,269 B1 | 7/2002 | Bui et al. | |
| 6,416,542 B1 | 7/2002 | Marcade et al. | |
| 6,468,260 B1 | 10/2002 | Bumbalough et al. | |
| 6,478,813 B1 | 11/2002 | Keith et al. | |
| 6,482,227 B1 | 11/2002 | Solovay | |
| 6,488,700 B2 | 12/2002 | Klumb et al. | |
| 6,500,203 B1 | 12/2002 | Thompson et al. | |
| 6,517,571 B1 | 2/2003 | Brauker et al. | |
| 6,517,572 B2 | 2/2003 | Kugler et al. | |
| 6,517,574 B1 | 2/2003 | Chuter | |
| 6,520,983 B1 | 2/2003 | Colgan et al. | |
| 6,524,336 B1 | 2/2003 | Papazolgou et al. | |

(56) References Cited

U.S. PATENT DOCUMENTS

| | | |
|---|---|---|
| 6,533,811 B1 | 3/2003 | Ryan et al. |
| 6,554,794 B1 | 4/2003 | Mueller et al. |
| 6,554,858 B2 | 4/2003 | Dereume et al. |
| RE38,146 E | 6/2003 | Palmaz et al. |
| 6,572,643 B1 | 6/2003 | Gharibadeh |
| 6,576,006 B2 | 6/2003 | Limon et al. |
| 6,585,756 B1 | 7/2003 | Strecker |
| 6,602,225 B2 | 8/2003 | Eidenschink et al. |
| 6,602,280 B2 | 8/2003 | Chobotov |
| 6,629,981 B2 | 10/2003 | Bui et al. |
| 6,645,242 B1 | 11/2003 | Quinn |
| 6,652,567 B1 | 11/2003 | Deaton |
| 6,656,215 B1 | 12/2003 | Yanez et al. |
| 6,660,030 B2 | 12/2003 | Shaolian et al. |
| 6,663,645 B2 | 12/2003 | Nishtala et al. |
| 6,669,716 B1 | 12/2003 | Gilson et al. |
| 6,682,557 B1 | 1/2004 | Quiachon et al. |
| 6,695,875 B2 | 2/2004 | Stelter et al. |
| 6,730,119 B1 | 5/2004 | Smalling |
| 6,733,521 B2 | 5/2004 | Chobotov et al. |
| 6,743,247 B1 | 6/2004 | Levinson et al. |
| 6,755,854 B2 | 6/2004 | Gillick et al. |
| 6,761,733 B2 | 7/2004 | Chobotov et al. |
| 6,773,454 B2 | 8/2004 | Wholey et al. |
| 6,773,457 B2 | 8/2004 | Ivancev et al. |
| 6,786,920 B2 | 9/2004 | Shannon et al. |
| 6,790,225 B1 | 9/2004 | Shannon et al. |
| 6,792,979 B2 | 9/2004 | Konya et al. |
| 6,808,529 B2 | 10/2004 | Fulkerson |
| 6,808,533 B1 | 10/2004 | Goodwin et al. |
| 6,808,534 B1 | 10/2004 | Escano |
| 6,814,752 B1 | 11/2004 | Chuter |
| 6,814,753 B2 | 11/2004 | Schmitt |
| 6,830,575 B2 | 12/2004 | Stenzel et al. |
| 6,843,802 B1 | 1/2005 | Villalobos et al. |
| 6,843,803 B2 | 1/2005 | Ryan et al. |
| 6,849,084 B2 | 2/2005 | Rabkin et al. |
| 6,858,038 B2 | 2/2005 | Heuser |
| 6,866,669 B2 | 3/2005 | Buzzard et al. |
| 6,878,164 B2 | 4/2005 | Kujawski et al. |
| 6,887,268 B2 | 5/2005 | Butaric et al. |
| 6,911,039 B2 | 6/2005 | Shiu et al. |
| 6,913,594 B2 | 7/2005 | Coleman et al. |
| 6,926,724 B1 | 8/2005 | Chu |
| 6,929,661 B2 | 8/2005 | Bolduc et al. |
| 6,939,352 B2 | 9/2005 | Buzzard et al. |
| 6,939,371 B2 | 9/2005 | Kugler et al. |
| 6,942,691 B1 | 9/2005 | Chuter |
| 6,942,692 B2 | 9/2005 | Landau et al. |
| 6,951,572 B1 | 10/2005 | Douglas |
| 6,964,679 B1 | 11/2005 | Marcade et al. |
| 6,974,471 B2 | 12/2005 | Van Schie et al. |
| 6,981,982 B2 | 1/2006 | Armstrong et al. |
| 6,984,243 B2 | 1/2006 | Dwyer et al. |
| 6,984,244 B2 | 1/2006 | Perez et al. |
| 7,000,649 B2 | 2/2006 | Takahashi et al. |
| 7,001,423 B2 | 2/2006 | Euteneuer et al. |
| 7,014,653 B2 | 3/2006 | Ouriel et al. |
| 7,018,401 B1 | 3/2006 | Hyodoh et al. |
| 7,048,014 B2 | 5/2006 | Hyodoh et al. |
| 7,052,511 B2 | 5/2006 | Weldon et al. |
| 7,052,513 B2 | 5/2006 | Thompson |
| 7,063,721 B2 | 6/2006 | Takahashi et al. |
| 7,074,236 B2 | 7/2006 | Rabkin et al. |
| 7,105,016 B2 | 9/2006 | Shiu et al. |
| 7,112,217 B1 | 9/2006 | Kugler et al. |
| 7,118,592 B1 | 10/2006 | Dang et al. |
| 7,122,050 B2 | 10/2006 | Randall et al. |
| 7,122,052 B2 | 10/2006 | Greenhalgh |
| 7,131,991 B2 | 11/2006 | Zarins et al. |
| 7,144,421 B2 | 12/2006 | Carpenter et al. |
| 7,147,656 B2 | 12/2006 | Andreas et al. |
| 7,160,318 B2 | 1/2007 | Greenberg et al. |
| 7,169,118 B2 | 1/2007 | Reynolds et al. |
| 7,175,651 B2 | 2/2007 | Kerr |
| 7,220,274 B1 | 5/2007 | Quinn |
| 7,226,474 B2 | 6/2007 | Iancea et al. |
| 7,229,472 B2 | 6/2007 | DePalma et al. |
| 7,232,459 B2 | 6/2007 | Greenberg et al. |
| 7,238,197 B2 | 7/2007 | Sequin et al. |
| 7,252,042 B1 * | 8/2007 | Blake ................ A01C 15/02 111/95 |
| 7,264,631 B2 | 9/2007 | DiCarlo |
| 7,264,632 B2 | 9/2007 | Wright et al. |
| 7,267,685 B2 | 9/2007 | Butaric et al. |
| 7,278,998 B2 | 10/2007 | Gaschino et al. |
| 7,294,147 B2 | 11/2007 | Hartley |
| 7,306,623 B2 | 12/2007 | Watson |
| 7,314,483 B2 | 1/2008 | Landau et al. |
| 7,314,484 B2 | 1/2008 | Deem et al. |
| 7,318,835 B2 | 1/2008 | Berra |
| 7,326,237 B2 | 2/2008 | DePalma et al. |
| 7,344,562 B2 | 3/2008 | Feller et al. |
| 7,357,812 B2 | 4/2008 | Andreas et al. |
| 7,371,255 B2 | 5/2008 | Richter et al. |
| RE40,404 E | 6/2008 | Schmitt et al. |
| 7,402,163 B2 | 7/2008 | Nishtala et al. |
| 7,435,253 B1 | 10/2008 | Hartley et al. |
| 7,473,271 B2 * | 1/2009 | Gunderson ............ A61F 2/91 623/1.12 |
| 7,476,244 B2 | 1/2009 | Buzzard et al. |
| 7,481,836 B2 | 1/2009 | Greenan |
| 7,488,344 B2 | 2/2009 | Hartley et al. |
| 7,517,361 B1 | 4/2009 | Ravenscroft |
| RE40,816 E | 6/2009 | Taylor et al. |
| 7,550,004 B2 | 6/2009 | Bahler et al. |
| 7,575,591 B2 | 8/2009 | Howat et al. |
| 7,588,596 B2 | 9/2009 | Spiridigliozzi et al. |
| 7,615,044 B2 | 11/2009 | Scheibe et al. |
| 7,615,071 B2 | 11/2009 | Chobotov |
| 7,637,932 B2 | 12/2009 | Bolduc et al. |
| 7,655,034 B2 | 2/2010 | Mitchell et al. |
| 7,655,040 B2 | 2/2010 | Douk et al. |
| 7,666,220 B2 | 2/2010 | Evans et al. |
| 7,674,282 B2 | 3/2010 | Wu et al. |
| 7,678,141 B2 | 3/2010 | Greenan et al. |
| 7,682,381 B2 | 3/2010 | Rakos et al. |
| 7,691,109 B2 | 4/2010 | Armstrong et al. |
| 7,691,138 B2 | 4/2010 | Stenzel et al. |
| 7,695,506 B2 | 4/2010 | Thistle et al. |
| 7,708,771 B2 | 5/2010 | Chuter et al. |
| 7,766,960 B2 | 8/2010 | Alexander et al. |
| 7,766,961 B2 | 8/2010 | Patel et al. |
| 7,780,717 B2 | 8/2010 | Ducke et al. |
| 7,828,833 B2 | 11/2010 | Haverkost et al. |
| 7,828,838 B2 | 11/2010 | Bolduc et al. |
| 7,837,724 B2 | 11/2010 | Keeble et al. |
| 7,862,609 B2 | 1/2011 | Butaric et al. |
| 7,887,576 B2 | 2/2011 | Bahler et al. |
| 7,918,880 B2 | 4/2011 | Austin |
| 1,012,524 A1 | 5/2011 | George et al. |
| 7,935,140 B2 | 5/2011 | Griffin |
| 7,938,852 B2 | 5/2011 | Andreas et al. |
| 7,993,384 B2 | 8/2011 | Wu et al. |
| 1,021,345 A1 | 9/2011 | Maclean et al. |
| 8,021,410 B2 | 9/2011 | Melsheimer |
| 8,025,692 B2 | 9/2011 | Feeser |
| 1,026,407 A1 | 10/2011 | Tegg et al. |
| 8,075,606 B2 | 12/2011 | Dorn |
| 8,080,050 B2 | 12/2011 | Chiang et al. |
| 8,114,147 B2 | 2/2012 | Wood et al. |
| 8,136,004 B2 | 3/2012 | Umesh et al. |
| 8,163,004 B2 | 4/2012 | Amplatz et al. |
| 8,163,006 B2 | 4/2012 | Feller et al. |
| 8,164,892 B2 | 4/2012 | An |
| 8,167,892 B2 | 5/2012 | Feller, III et al. |
| 8,187,291 B2 | 5/2012 | Nishtala et al. |
| 8,241,344 B2 | 8/2012 | Kusleika et al. |
| 8,287,583 B2 | 10/2012 | LaDuca et al. |
| 8,323,239 B2 | 12/2012 | Bednarek et al. |
| 8,357,190 B2 | 1/2013 | Fearn et al. |
| 8,372,131 B2 | 2/2013 | Hestad et al. |
| 8,434,393 B2 | 5/2013 | Adams |
| 8,470,015 B2 | 6/2013 | Barthold |

(56) References Cited

U.S. PATENT DOCUMENTS

| | | |
|---|---|---|
| 8,486,128 B2 | 7/2013 | Jen et al. |
| 8,858,613 B2 | 10/2014 | Cragg et al. |
| 2001/0014823 A1 | 8/2001 | Ressemann et al. |
| 2002/0013620 A1 | 1/2002 | Kujawski |
| 2002/0019659 A1 | 2/2002 | Goicoechea et al. |
| 2002/0019664 A1 | 2/2002 | Douglas |
| 2002/0058987 A1 | 5/2002 | Butaric et al. |
| 2002/0143387 A1 | 10/2002 | Soetikno et al. |
| 2002/0151933 A1 | 10/2002 | Sheldon |
| 2002/0169497 A1 | 11/2002 | Wholey et al. |
| 2003/0014075 A1 | 1/2003 | Rosenbluth et al. |
| 2003/0125800 A1* | 7/2003 | Shulze ............... A61F 2/90 623/1.15 |
| 2003/0130720 A1 | 7/2003 | DePalma et al. |
| 2003/0130725 A1 | 7/2003 | DePalma et al. |
| 2003/0191516 A1 | 10/2003 | Weldon et al. |
| 2003/0199967 A1 | 10/2003 | Hartley et al. |
| 2003/0199973 A1 | 10/2003 | Chuter et al. |
| 2004/0019375 A1 | 1/2004 | Casey et al. |
| 2004/0054397 A1 | 3/2004 | Smith et al. |
| 2004/0059406 A1 | 3/2004 | Cully et al. |
| 2004/0059407 A1 | 3/2004 | Escamilla et al. |
| 2004/0073288 A1 | 4/2004 | Kerr |
| 2004/0082989 A1 | 4/2004 | Cook et al. |
| 2004/0098092 A1 | 5/2004 | Butaric et al. |
| 2004/0117003 A1 | 6/2004 | Ouriel et al. |
| 2004/0138734 A1 | 7/2004 | Chobotov et al. |
| 2004/0143316 A1 | 7/2004 | Spiridigliozzi et al. |
| 2004/0162604 A1 | 8/2004 | Sowinski et al. |
| 2004/0167599 A1 | 8/2004 | Goicoechea et al. |
| 2004/0193245 A1 | 9/2004 | Deem et al. |
| 2004/0193252 A1 | 9/2004 | Perez et al. |
| 2004/0215316 A1 | 10/2004 | Smalling |
| 2004/0230289 A1 | 11/2004 | DiMatteo et al. |
| 2004/0236406 A1 | 11/2004 | Gregorich |
| 2004/0260382 A1 | 12/2004 | Fogarty et al. |
| 2005/0015441 A1 | 1/2005 | Attwood et al. |
| 2005/0021123 A1 | 1/2005 | Dorn et al. |
| 2005/0033400 A1 | 2/2005 | Chuter |
| 2005/0033416 A1 | 2/2005 | Seguin et al. |
| 2005/0043780 A1 | 2/2005 | Gifford et al. |
| 2005/0049607 A1 | 3/2005 | Hart et al. |
| 2005/0085894 A1 | 4/2005 | Kershner |
| 2005/0113906 A9 | 5/2005 | Bolduc et al. |
| 2005/0119721 A1* | 6/2005 | Rabkin ............... A61F 2/95 623/1.12 |
| 2005/0131516 A1 | 6/2005 | Greenhalgh |
| 2005/0137677 A1 | 6/2005 | Rush |
| 2005/0143804 A1 | 6/2005 | Haverkost |
| 2005/0154441 A1 | 7/2005 | Schaeffer et al. |
| 2005/0171598 A1 | 8/2005 | Schaeffer |
| 2005/0222668 A1 | 10/2005 | Schaeffer et al. |
| 2005/0228475 A1 | 10/2005 | Keeble et al. |
| 2005/0228484 A1 | 10/2005 | Stephens et al. |
| 2005/0240258 A1 | 10/2005 | Bolduc et al. |
| 2005/0273154 A1 | 12/2005 | Colone |
| 2005/0288772 A1 | 12/2005 | Douglas |
| 2006/0030921 A1 | 2/2006 | Chu |
| 2006/0058864 A1 | 3/2006 | Schaeffer et al. |
| 2006/0069323 A1 | 3/2006 | Elkins et al. |
| 2006/0074481 A1 | 4/2006 | Vardi et al. |
| 2006/0085057 A1 | 4/2006 | George et al. |
| 2006/0095116 A1 | 5/2006 | Bolduc et al. |
| 2006/0142694 A1 | 6/2006 | Bednarek et al. |
| 2006/0155359 A1 | 7/2006 | Watson |
| 2006/0155366 A1 | 7/2006 | LaDuca et al. |
| 2006/0161244 A1 | 7/2006 | Seguin |
| 2006/0178733 A1 | 8/2006 | Pinchuk et al. |
| 2006/0212112 A1 | 9/2006 | Evans et al. |
| 2006/0224232 A1 | 10/2006 | Chobotov |
| 2006/0233990 A1 | 10/2006 | Humphrey et al. |
| 2006/0265055 A1 | 11/2006 | Lauterjung |
| 2006/0271153 A1* | 11/2006 | Garcia ............ A61B 17/12022 623/1.11 |
| 2006/0282155 A1 | 12/2006 | Fearn et al. |
| 2007/0032852 A1 | 2/2007 | Machek et al. |
| 2007/0051377 A1 | 3/2007 | Douk et al. |
| 2007/0055341 A1 | 3/2007 | Edoga et al. |
| 2007/0055360 A1 | 3/2007 | Hanson et al. |
| 2007/0055363 A1 | 3/2007 | Chuter et al. |
| 2007/0100429 A1 | 5/2007 | Wu et al. |
| 2007/0118208 A1 | 5/2007 | Kerr |
| 2007/0142895 A1 | 6/2007 | Castaneda et al. |
| 2007/0142896 A1 | 6/2007 | Anderson et al. |
| 2007/0150041 A1 | 6/2007 | Evans et al. |
| 2007/0156224 A1 | 7/2007 | Cioanta et al. |
| 2007/0156229 A1 | 7/2007 | Park |
| 2007/0162109 A1 | 7/2007 | Davila et al. |
| 2007/0168017 A1 | 7/2007 | Sarac |
| 2007/0168018 A1 | 7/2007 | Amplatz et al. |
| 2007/0173929 A1 | 7/2007 | Boucher et al. |
| 2007/0179592 A1 | 8/2007 | Schaeffer |
| 2007/0179600 A1 | 8/2007 | Vardi |
| 2007/0198077 A1 | 8/2007 | Cully et al. |
| 2007/0198079 A1 | 8/2007 | Casey et al. |
| 2007/0219620 A1 | 9/2007 | Eells et al. |
| 2007/0225797 A1 | 9/2007 | Krivoruhko |
| 2007/0233220 A1 | 10/2007 | Greenan |
| 2007/0233222 A1 | 10/2007 | Roeder et al. |
| 2007/0244542 A1 | 10/2007 | Greenan et al. |
| 2007/0244547 A1 | 10/2007 | Greenan |
| 2007/0265697 A1 | 11/2007 | Goicoechea et al. |
| 2007/0293940 A1 | 12/2007 | Schaeffer et al. |
| 2008/0015682 A1 | 1/2008 | Majercak et al. |
| 2008/0046065 A1 | 2/2008 | Hartley et al. |
| 2008/0082154 A1 | 4/2008 | Tseng et al. |
| 2008/0082158 A1 | 4/2008 | Tseng et al. |
| 2008/0082159 A1 | 4/2008 | Tseng et al. |
| 2008/0097572 A1 | 4/2008 | Sheldon et al. |
| 2008/0108969 A1 | 5/2008 | Kerr |
| 2008/0114435 A1 | 5/2008 | Bowe |
| 2008/0114444 A1 | 5/2008 | Yu |
| 2008/0114449 A1 | 5/2008 | Gregorich et al. |
| 2008/0125847 A1 | 5/2008 | Krever et al. |
| 2008/0132993 A1 | 6/2008 | Rasmussen et al. |
| 2008/0167704 A1 | 7/2008 | Wright et al. |
| 2008/0183272 A1 | 7/2008 | Wood et al. |
| 2008/0195191 A1 | 8/2008 | Luo et al. |
| 2008/0208325 A1 | 8/2008 | Helmus et al. |
| 2008/0221659 A1 | 9/2008 | Hartley et al. |
| 2008/0221668 A1 | 9/2008 | Pinchuk et al. |
| 2008/0249601 A1 | 10/2008 | Kerr |
| 2008/0262595 A1 | 10/2008 | Chu et al. |
| 2008/0290076 A1 | 11/2008 | Sheldon et al. |
| 2009/0030501 A1 | 1/2009 | Morris et al. |
| 2009/0036973 A1 | 2/2009 | Humphrey et al. |
| 2009/0043376 A1 | 2/2009 | Hamer et al. |
| 2009/0085186 A1 | 4/2009 | Meyer |
| 2009/0099647 A1 | 4/2009 | Glimsdale et al. |
| 2009/0099649 A1 | 4/2009 | Chobotov et al. |
| 2009/0105640 A1 | 4/2009 | Bednarek et al. |
| 2009/0125095 A1 | 5/2009 | Bui et al. |
| 2009/0138067 A1 | 5/2009 | Pinchuk et al. |
| 2009/0164001 A1 | 6/2009 | Biggs et al. |
| 2009/0171451 A1 | 7/2009 | Kuppurathanam et al. |
| 2009/0173439 A1 | 7/2009 | Hayashi et al. |
| 2009/0177265 A1 | 7/2009 | Dierking et al. |
| 2009/0182413 A1 | 7/2009 | Burkart et al. |
| 2009/0187240 A1 | 7/2009 | Clerc et al. |
| 2009/0198267 A1 | 8/2009 | Evans et al. |
| 2009/0228020 A1 | 9/2009 | Wallace et al. |
| 2009/0248144 A1 | 10/2009 | Bahler et al. |
| 2009/0264992 A1 | 10/2009 | Fleming, III et al. |
| 2009/0276035 A1 | 11/2009 | Waysbeyn et al. |
| 2009/0287145 A1 | 11/2009 | Cragg et al. |
| 2009/0318949 A1 | 12/2009 | Ganpath et al. |
| 2009/0319029 A1 | 12/2009 | Evans et al. |
| 2010/0004728 A1 | 1/2010 | Rao et al. |
| 2010/0030255 A1 | 2/2010 | Berra et al. |
| 2010/0030321 A1 | 2/2010 | Mach |
| 2010/0036360 A1 | 2/2010 | Herbowy et al. |
| 2010/0049291 A1 | 2/2010 | Yampolsky et al. |
| 2010/0094394 A1 | 4/2010 | Beach et al. |
| 2010/0094400 A1 | 4/2010 | Bolduc et al. |

(56) References Cited

U.S. PATENT DOCUMENTS

| | | |
|---|---|---|
| 2010/0094403 A1 | 4/2010 | Heraty et al. |
| 2010/0100167 A1 | 4/2010 | Bortlein et al. |
| 2010/0106239 A1 | 4/2010 | Roeder |
| 2010/0211153 A1* | 8/2010 | Cook .................. A61F 2/966 623/1.11 |
| 2010/0262216 A1 | 10/2010 | Xue |
| 2010/0268327 A1 | 10/2010 | Bruszewski et al. |
| 2010/0286756 A1 | 11/2010 | Dorn et al. |
| 2010/0292771 A1 | 11/2010 | Paskar |
| 2010/0305686 A1 | 12/2010 | Cragg et al. |
| 2011/0022149 A1 | 1/2011 | Cox et al. |
| 2011/0060398 A1* | 3/2011 | Tupil .................. A61F 2/07 623/1.15 |
| 2011/0079315 A1 | 4/2011 | Norton et al. |
| 2011/0130819 A1 | 6/2011 | Cragg et al. |
| 2011/0130820 A1 | 6/2011 | Cragg et al. |
| 2011/0130824 A1 | 6/2011 | Cragg et al. |
| 2011/0130825 A1 | 6/2011 | Cragg et al. |
| 2011/0130826 A1 | 6/2011 | Cragg et al. |
| 2011/0178589 A1 | 7/2011 | Andreas et al. |
| 2011/0213450 A1 | 9/2011 | Maclean et al. |
| 2011/0257673 A1 | 10/2011 | Heraty et al. |
| 2011/0257720 A1 | 10/2011 | Peterson et al. |
| 2011/0264186 A1* | 10/2011 | Berglung .................. A61F 2/86 623/1.11 |
| 2011/0295354 A1 | 12/2011 | Bueche et al. |
| 2011/0307049 A1* | 12/2011 | Kao .................. A61F 2/966 623/1.11 |
| 2011/0313505 A1 | 12/2011 | McHugo |
| 2012/0041536 A1 | 2/2012 | Hansen |
| 2012/0130469 A1 | 5/2012 | Cragg et al. |
| 2012/0158115 A9 | 6/2012 | Arnault De La Menardiere et al. |
| 2012/0158117 A1 | 6/2012 | Ryan |
| 2012/0165919 A1 | 6/2012 | Cox et al. |
| 2012/0172968 A1 | 7/2012 | Chuter et al. |
| 2012/0185031 A1 | 7/2012 | Ryan et al. |
| 2012/0197376 A1 | 8/2012 | Heidner et al. |
| 2012/0209063 A1 | 8/2012 | Nishtala et al. |
| 2012/0221091 A1 | 8/2012 | Hartly et al. |
| 2012/0221093 A1 | 8/2012 | McHugo |
| 2012/0330398 A1 | 12/2012 | Hyodoh et al. |
| 2013/0035749 A1 | 2/2013 | Farag |
| 2013/0096407 A1 | 4/2013 | Bednarek et al. |
| 2013/0123898 A1 | 5/2013 | Tung et al. |
| 2013/0131774 A1 | 5/2013 | Nabulsi et al. |
| 2014/0046428 A1 | 2/2014 | Cragg et al. |
| 2014/0046429 A1 | 2/2014 | Cragg et al. |
| 2014/0052232 A1 | 2/2014 | Cragg et al. |

FOREIGN PATENT DOCUMENTS

| | | |
|---|---|---|
| EP | 808613 | 11/1997 |
| EP | 971646 | 9/2004 |
| EP | 1803418 | 7/2007 |
| FR | 2743293 | 7/1997 |
| JP | A-H10-507382 | 7/1988 |
| JP | A-H08-501471 | 2/1996 |
| JP | A-H11-501243 | 2/1999 |
| JP | A-2000-185105 | 7/2000 |
| JP | A-2006-518710 | 6/2008 |
| JP | A-2008-539050 | 11/2008 |
| JP | A-2009-504349 | 2/2009 |
| WO | WO-1993019703 | 10/1993 |
| WO | WO-9632077 | 10/1996 |
| WO | 9844873 A1 | 10/1998 |
| WO | WO-1998052496 A1 | 11/1998 |
| WO | WO-9855047 | 12/1998 |
| WO | 0103762 A1 | 1/2001 |
| WO | WO-0105332 | 1/2001 |
| WO | WO-0152770 | 7/2001 |
| WO | WO 2002/066094 A2 | 8/2002 |
| WO | WO 2003/084439 A1 | 10/2003 |
| WO | WO-2003084439 | 10/2003 |
| WO | WO 2004/091450 A2 | 10/2004 |
| WO | WO-2005112823 | 12/2005 |
| WO | WO-2006116725 | 11/2006 |
| WO | WO-2008005535 | 1/2008 |
| WO | 2009085186 A1 | 7/2009 |
| WO | WO-2009132309 | 10/2009 |
| WO | WO-2009140638 | 11/2009 |
| WO | 2010127040 A1 | 11/2010 |
| WO | WO-2010132836 | 11/2010 |
| WO | WO-2011003019 | 1/2011 |
| WO | WO-2011049808 | 4/2011 |
| WO | WO-2011068915 | 6/2011 |
| WO | WO-2012040240 | 3/2012 |
| WO | 2012088888 A1 | 7/2012 |
| WO | WO-2012128846 | 9/2012 |

OTHER PUBLICATIONS

Australian Patent Examination Report No. 1, Australian Patent Application No. 2010248822; dated Nov. 26, 2014; 3 pages.
Australian Patent Examination Report No. 1, Australian Patent Application No. 2010326046; dated Feb. 27, 2015; 2 pages.
Australian Patent Examination Report No. 1, Australian Patent Application No. 2012203705; dated Jan. 31, 2013; 4 pages.
Australian Patent Examination Report No. 1, Australian Patent Application No. 2012203708; dated Feb. 1, 2013; 5 pages.
Australian Patent Examination Report No. 1, Australian Patent Application No. 2012203709; dated Jan. 30, 2013; 4 pages.
Chinese Office Action 1; Chinese Patent Application No. 200980126821.7, dated Apr. 3, 2013, 12 pages.
Chinese Office Action 1; Chinese Patent Application No. 201080031916.3, dated Jan. 16, 2014, 12 pages.
Chinese Office Action 2; Chinese Patent Application No. 200980126821.7, dated Dec. 24, 2013, 11 pages.
Extended European Search Report, European Application No. 12174632.5, dated Sep. 26, 2014, 7 pages.
Extended European Search Report, European Application No. 12174641.6, dated Sep. 29, 2014, 7 pages.
Extended European Search Report, European Application No. 12174645.7, dated Sep. 29, 2014, 5 pages.
Extended European Search Report, European Application No. 12174647.3, dated Sep. 29, 2014, 9 pages.
Final Office Action, U.S. Appl. No. 12/466,044, dated May 29, 2013, 14 pages.
Final Office Action; U.S. Appl. No. 12/958,367; dated Mar. 28, 2013; 27 pages.
Final Office Action; U.S. Appl. No. 12/958,374, dated Apr. 1, 2013, 26 pages.
Final Office Action; U.S. Appl. No. 12/958,378; dated Mar. 29, 2013; 35 pages.
International Search Report and Written Opinion, PCT/US2014/029373, dated Aug. 12, 2014, Applicant: Altura Medical, Inc., 14 pages.
Japanese Office Action, Japanese Application No. 2012-511058, dated Jan. 7, 2015, 8 pages.
Japanese Office Action; Japanese Patent Application No. 2011-509771, dated Jul. 10, 2013, 5 pages.
Non-Final Office Action, U.S. Appl. No. 12/628,131, dated Feb. 13, 2014 15 pages.
Non-Final Office Action, U.S. Appl. No. 12/958,367, dated Dec. 16, 2014, 28 pages.
Non-Final Office Action, U.S. Appl. No. 12/958,374, dated Dec. 3, 2014, 24 pages.
Non-Final Office Action, U.S. Appl. No. 12/958,383, dated Apr. 13, 2015, 45 pages.
Non-Final Office Action; U.S. Appl. No. 13/964,015; dated Dec. 29, 2014; 16 pages.
Japanese Office Action, Japanese Application No. 2012-511058, dated Apr. 3, 2014, 38 pages.
Final Office Action, U.S. Appl. No. 12/466,044, dated Jun. 19, 2014, 15 pages.
Chinese Office Action, Chinese Application No. 2009801268217, dated May 7, 2014, 12 pages.

(56) References Cited

OTHER PUBLICATIONS

Japanese Office Action; Japanese Patent Application No. 2011-509771, dated May 28, 2014, 10 pages.
Non-Final Office Action; U.S. Appl. No. 12/958,383, dated Jul. 31, 2014, 45 pages.
International Search Report and Written Opinion; App. No. PCT/US2013/054438, dated Feb. 7, 2014, Applicant: Andrew H. Cragg, 23 pages.
U.S. Appl. No. 61/265,713, filed Dec. 1, 2009, Cragg et al.
U.S. Appl. No. 12/958,367, filed Jun. 2, 2011, Cragg et al.
U.S. Appl. No. 12/958,374, filed Jun. 2, 2011, Cragg et al.
U.S. Appl. No. 12/958,378, filed Jun. 2, 2011, Cragg et al.
U.S. Appl. No. 12/958,381, filed Jun. 2, 2011, Cragg et al.
U.S. Appl. No. 12/958,383, filed Jun. 2, 2011, Cragg et al.
U.S. Appl. No. 61/053,378, filed May 15, 2008, Cragg et al.
U.S. Appl. No. 61/293,581, filed Jan. 8, 2010, Cragg et al.
U.S. Appl. No. 61/311,735, filed Mar. 8, 2010, Cragg et al.
U.S. Appl. No. 61/320,646, filed Apr. 2, 2010, Cragg et al.
U.S. Appl. No. 61/384,669, filed Sep. 20, 2010, Cragg et al.
Beebe, H.G.; "Imaging Modalities for Aortic Endografting"; J Endovasc Surg; May 1997; vol. 4, Issue 2, pp. 111-123 (20 pages).
Brewster, DC; "Initial Experience with Endovascular Aneurysm Repair: Comparison of Early Results with Outcome of Conventional Open Repair"; J Vasc Surg; Jun. 1998; vol. 27, Issue 6, pp. 992-1003; discussion 1004-5 (14 pages).
Dorros, G. et al.; "Evaluation of Endovascular Abdominal Aortic Aneurysm Repair: Anatomical Classicication, Procedural Success, Clinical Assessment, and Data Collection"; J. Endovasc Surg; May 1997; vol. 4, Issue 2; pp. 203-225 (24 pages).
Dosluoglu et al.; "Total Percutaneous Endovascular Repair of Abdominal Aortic Aneurysms Using Perclose ProGlide Closure Devices"; J. Endovasc Ther.; Apr. 2007, vol. 14, Issue 2, pp. 184-188 (5 pages).
Final Office Action; U.S. Appl. No. 12/466,044; dated Sep. 14, 2012; 9 pages.
Final Office Action; U.S. Appl. No. 12/628,131; dated Nov. 21, 2012; 19 pages.
Final Office Action; U.S. Appl. No. 12/958,383; dated Jan. 9, 2013; 29 pages.
Final Office Action; U.S. Appl. No. 12/958,381; dated Jan. 31, 2013; 36 pages.
International Search Report and Written Opinion, PCT/US09/44212, dated Jul. 14, 2009, Applicant: Altura Medical, Inc., 11 pages.
International Search Report and Written Opinion, PCT/US10/58621, dated Feb. 9, 2011, Applicant: Altura Medical, Inc., 33 pages.
International Search Report and Written Opinion, PCT/US2010/035003, dated Feb. 9, 2011, Applicant: Altura Medical, Inc., 10 pages.
International Search Report and Written Opinion, PCT/US2011/052412, dated Jan. 17, 2012, Applicant: Altura Medical, Inc., 9 pages.
Kahraman, H. et al., "The Diameters of the Aorta and Its Major Branches in Patients with Isolated Coronary Artery Ectasia," Texas Heart Institute Journal; 2006, vol. 33, No. 4, pp. 463-468.
Laborde, J.C. et al., "A Novel 14F Endograft for Abdominal Aortic Aneurysm: First in Man," *Catheterization and Cardiovascular Interventions*, Jun. 2010 (20 pages).
Laborde, J.C. et al., "Intraluminal Bypass of Abdominal Aortic Aneurysm: Feasibility Study"; Radiology; Jul. 1992; vol. 184, Issue 1; pp. 185-190 (6 pages).
Matsumura, JS; "A Multicenter Controlled Clinical Trial of Open Versus Endovascular Treatment of Abdominal Aortic Aneurysm"; J Vasc Surg; Feb. 2003; vol. 37, Issue 2, pp. 262-271 (13 pages).
Non-Final Office Action, U.S. Appl. No. 12/466,044, dated May 7, 2012, 35 pages.
Non-Final Office Action, U.S. Appl. No. 12/628,131, dated May 11, 2012, 20 pages.
Non-Final Office Action, U.S. Appl. No. 12/958,367, dated Aug. 17, 2012, 28 pages.
Non-Final Office Action, U.S. Appl. No. 12/958,374, dated Aug. 16, 2012, 28 pages.
Non-Final Office Action, U.S. Appl. No. 12/958,378, dated Aug. 16, 2012, 25 pages.
Non-Final Office Action, U.S. Appl. No. 12/958,381, dated Aug. 9, 2012, 30 pages.
Non-Final Office Action, U.S. Appl. No. 12/958,383, dated Aug. 16, 2012, 28 pages.
Non-Final Office Action, U.S. Appl. No. 12/466,044, dated Jan. 3, 2013, 12 pages.
Parodi, J.C. et al., "Transfemoral Intraluminal Graft Implantation for Abdominal Aortic Aneurysms", Ann Vasc Surg.; Nov. 1991; vol. 5, Issue 6, pp. 491-499 (9 pages).
Powell, J.T. et al.; "Final 12-year Follow-up of Surgery Versus Surveillance in the UK Small Aneurysm Trial"; Br. J. Surg.; Jun. 2007; vol. 94, Issue 6, pp. 702-708 (7 pages).
Volodos, N.L. et al.; "Clinical Experience of the use of Self-Fixing Synthetic Prostheses for Remote Endoprosthetics of the Thoracic and the Abdominal Aorta and Iliac Arteries Through the Femoral Artery and as Intraoperative Endoprosthesis for Aorta Reconstruction"; Kharkov Research Institute of General and urgent Surgery; J. Vasa Diseases—Suppl.; 1991; vol. 33, pp. 93-95 (5 pages).
Zarins, C.K.; "AneuRx Stent Graft Versus Open Surgical Repair of Abdominal Aortic Aneurysms: Multicenter Prospective Clinical Trial"; J Vasc Surg; Feb. 1999; vol. 29, Issue 2, pp. 292-308 (19 pages).
Zarins C.K.; "Endovascular Repair or Surveillance of Patients with Small AAA"; Eur. J. Vasc. Endovasc. Surg.; May 2005; vol. 29, Issue 5; pp. 496-503; located at www.sciencedirect.com (9 pages).
Dereume, J.P. et al., "Endoluminal Treatment of Abdominal Aortic Aneurysm with the Corvita Endovascular Graft. Results of a Single-Center, Prospective Feasibility Study of 90 Patients," Journal of Endovascular Survery; Nov. 1996, vol. 3, 1 page.
Chinese Preliminary Examination Report; Chinese Patent Application No. 100876, dated Mar. 30, 2012, 1 page.
Australian Patent Examination Report No. 1, Australian Patent Application No. 2012203707, dated Jan. 31, 2013, 4 pages.
Sanchez, Luis et al., "Early Experience with the Corvita Endoluminal Graft for Treatment of Arterial Injuries," From the Divisions of Vascular Surgery and Interventional Radiology, Montefiore Medical Center, New York. Presented May 31, 1997, 7 pages.
Sitsen, M. et al., "Deformation of Self-Expanding Stent-Grafts Complicating Endovascular Peripheral Aneurysm Repair," J Edovascular Surgery, 1999. 5 pages.
Non-Final Office Action, U.S. Appl. No. 13/237,822, dated Dec. 5, 2013, 11 pages.
Cao, P.; "Comparison of Surveillance vs. Aortic Endografting for Small Aneurysm Repair (CAESAR) Trial: Study Design and Progress"; Eur. J. Vasc. Endovasc. Surg.; Sep. 2005; vol. 30, Issue 3; pp. 245-251 (7 pages).
Faries, P.L.; "Endovascular Stent Graft Selection for the Treatment of Abdominal Aortic Aneurysms"; J. Cardiovasc Surg (Torino); Feb. 2005; vol. 46, Issue 1, pp. 9-17 (9 pages).
Mathison, M.N.; "Implications of Problematic Access in Transluminal Endografting of Abdominal Aortic Aneurysm"; J Vasc Interv Radiol; Jan. 2003; vol. 14, Issue 1, pp. 33-39 (7 pages).
U.S. Appl. No. 13/963,912, filed Aug. 9, 2013, Cragg et al.
U.S. Appl. No. 13/964,015, filed Aug. 9, 2013, Cragg et al.
Final Office Action, U.S. Appl. No. 12/628,131, dated Oct. 8, 2014, 20 pages.
Non-Final Office Action; U.S. Appl. No. 12/958,381, dated Oct. 3, 2014, 17 pages.
Chinese Office Action, Chinese Application No. 200980126821.7, dated Sep. 11, 2014, 5 pages.
Chinese Office Action, Chinese Application No. 201080062913.6, dated Nov. 15, 2014, 13 pages.
Japanese Office Action, Japanese Application No. 2012-542171, dated Sep. 24, 2014, 2 pages.

\* cited by examiner

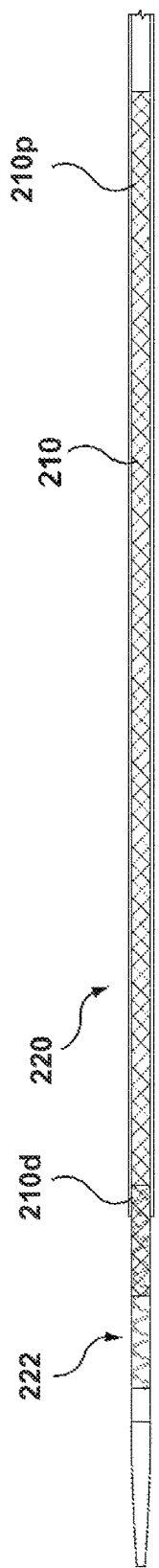
FIG. 2B
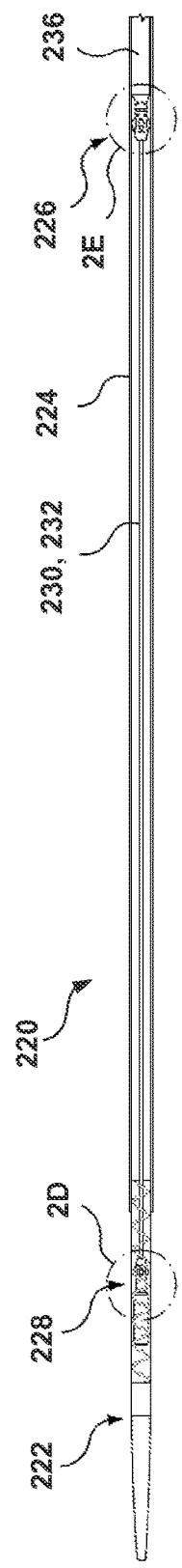
FIG. 2C
FIG. 2E
FIG. 2D

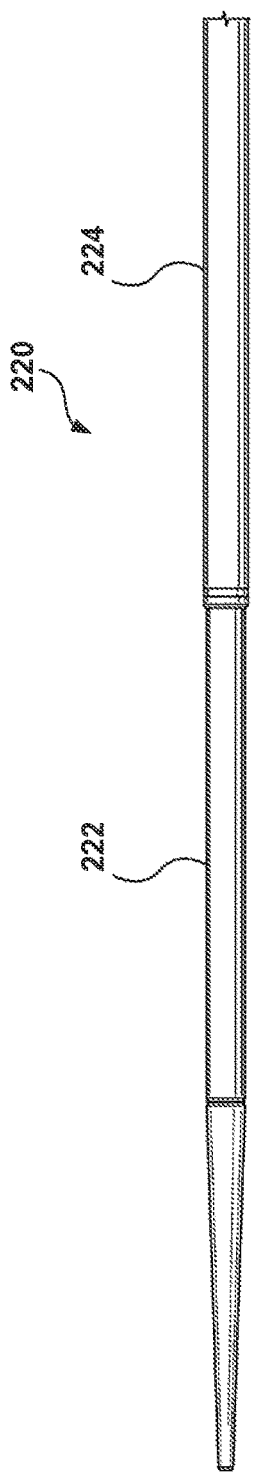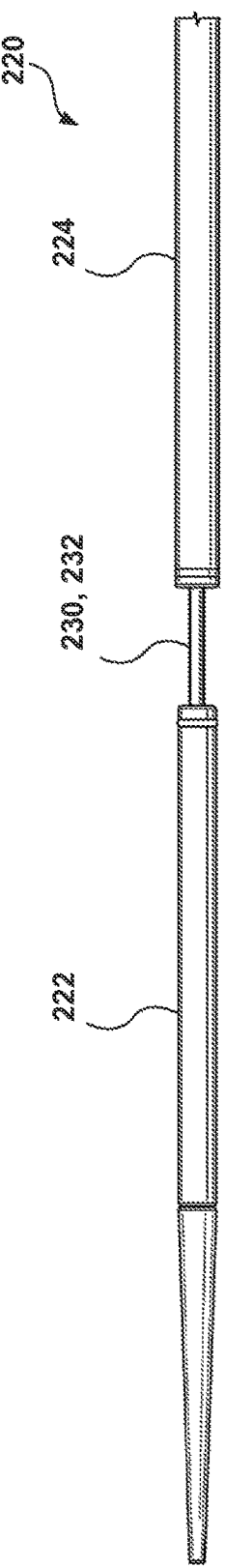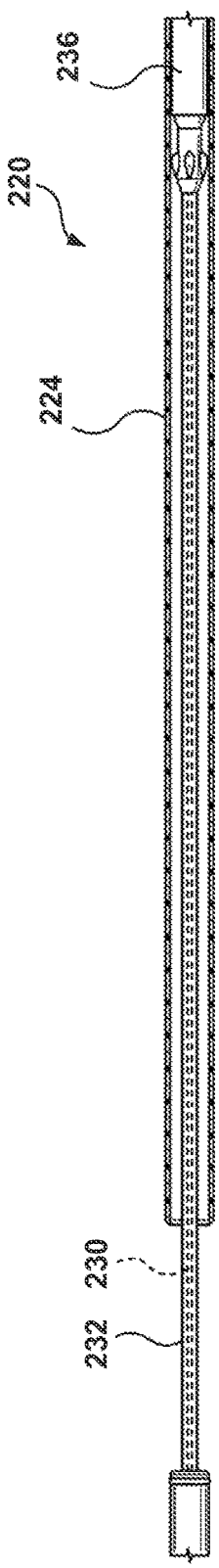

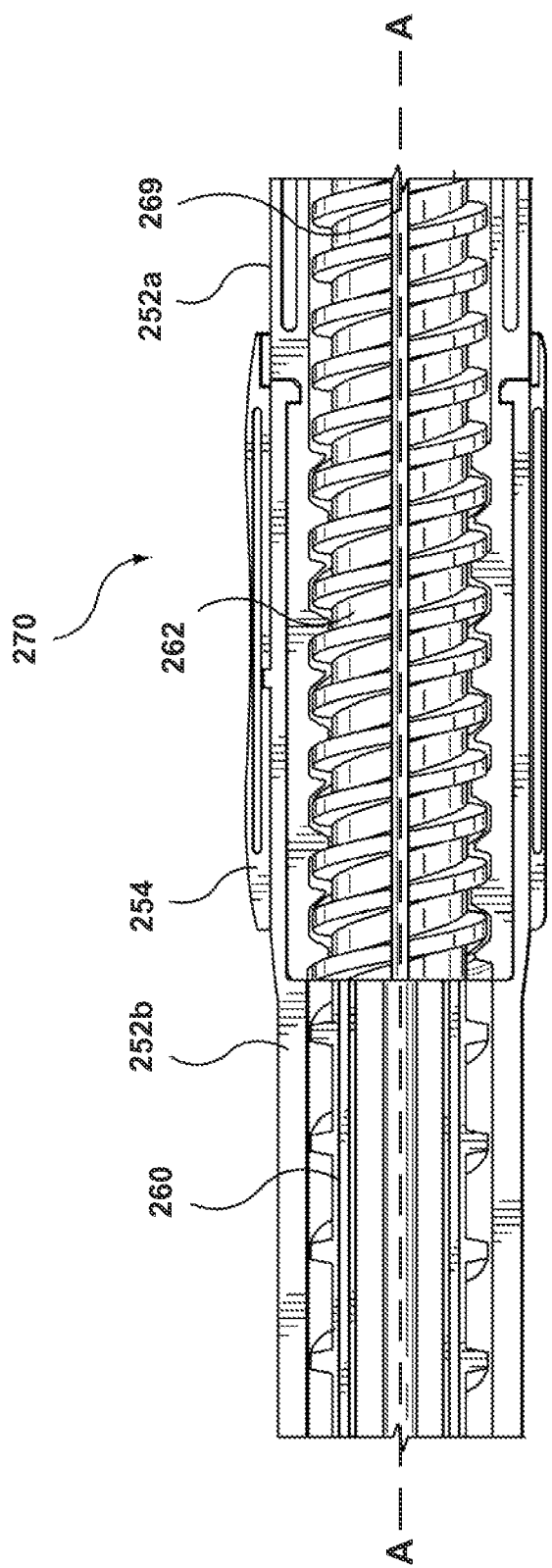
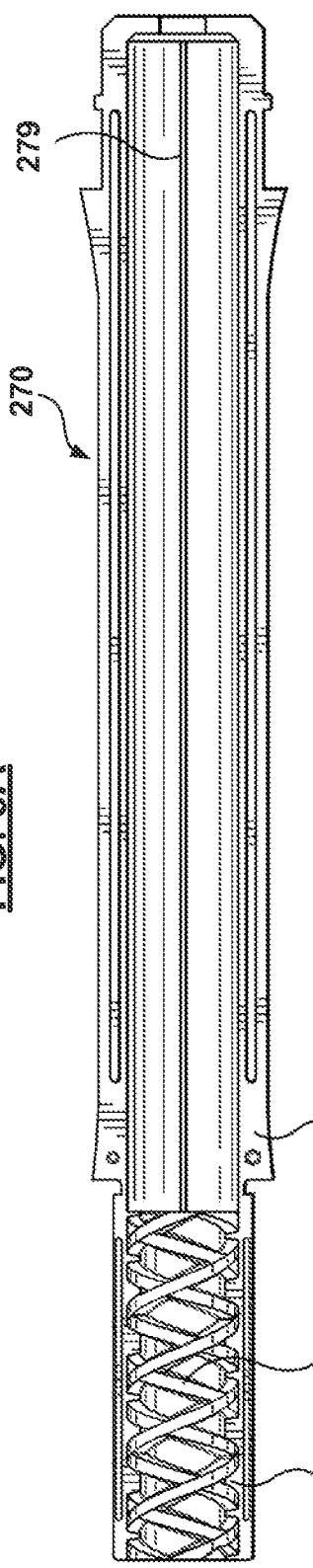
FIG. 5A
FIG. 5B

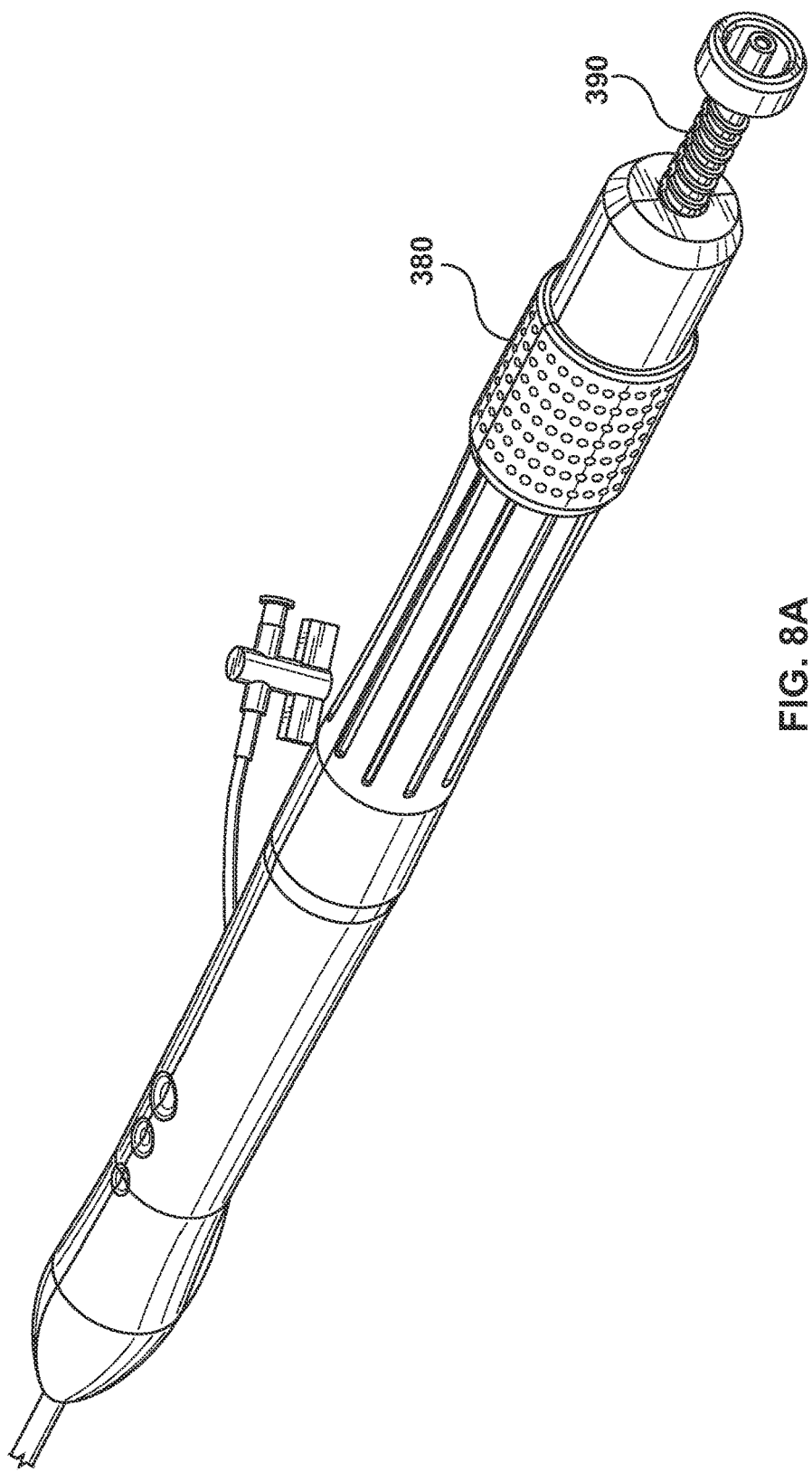

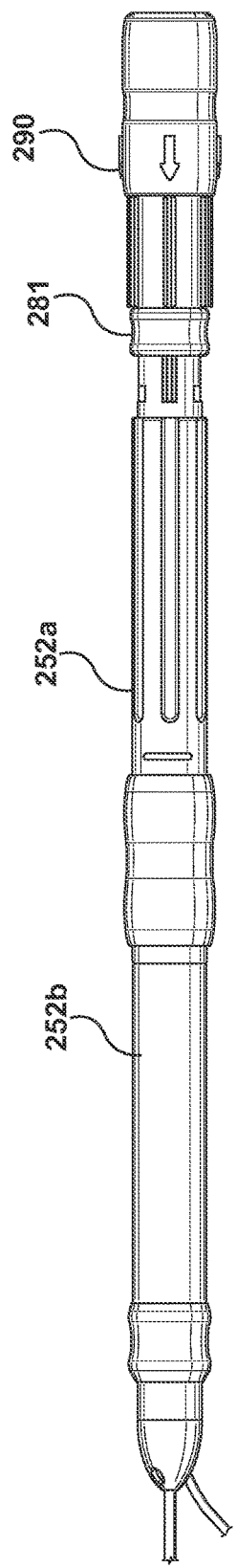
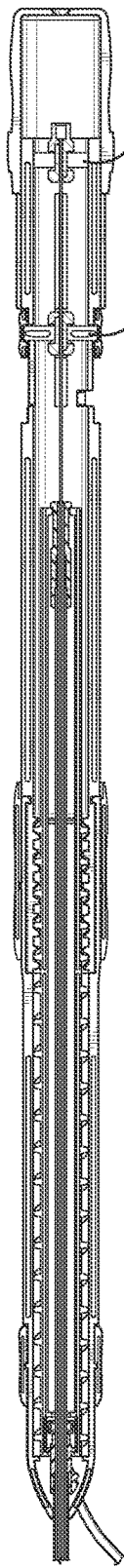
FIG. 10A
FIG. 10B

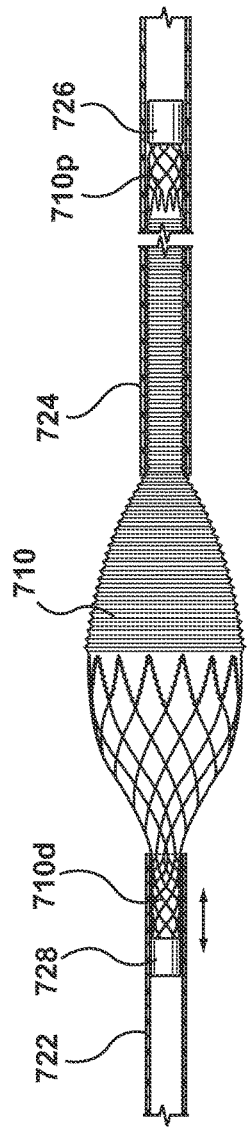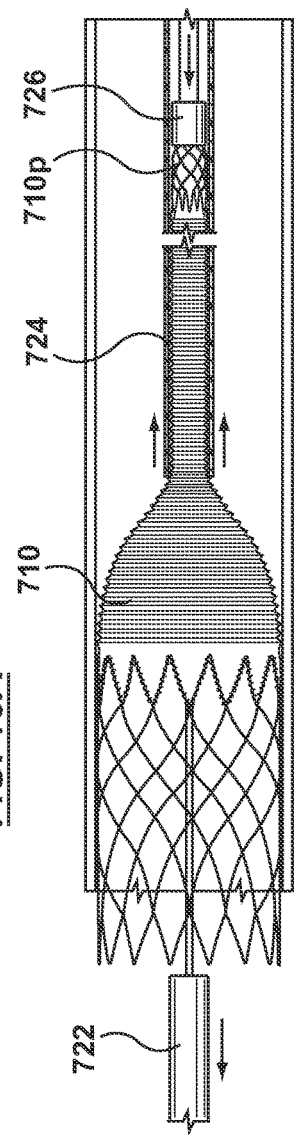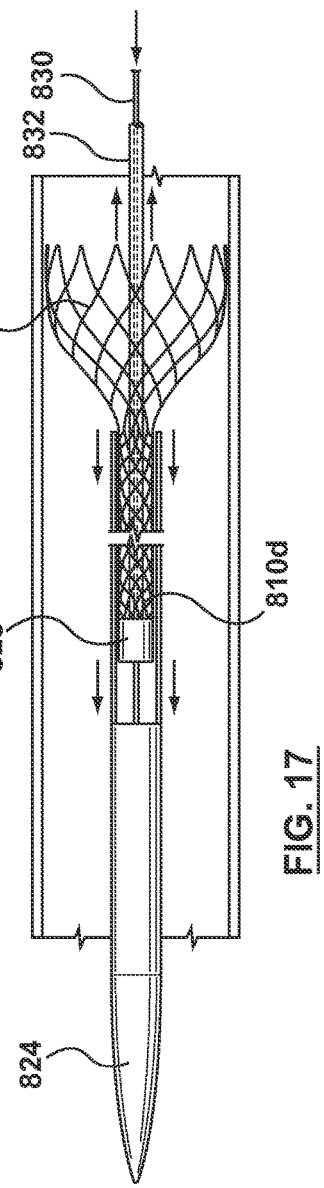
FIG. 16A
FIG. 16B
FIG. 17

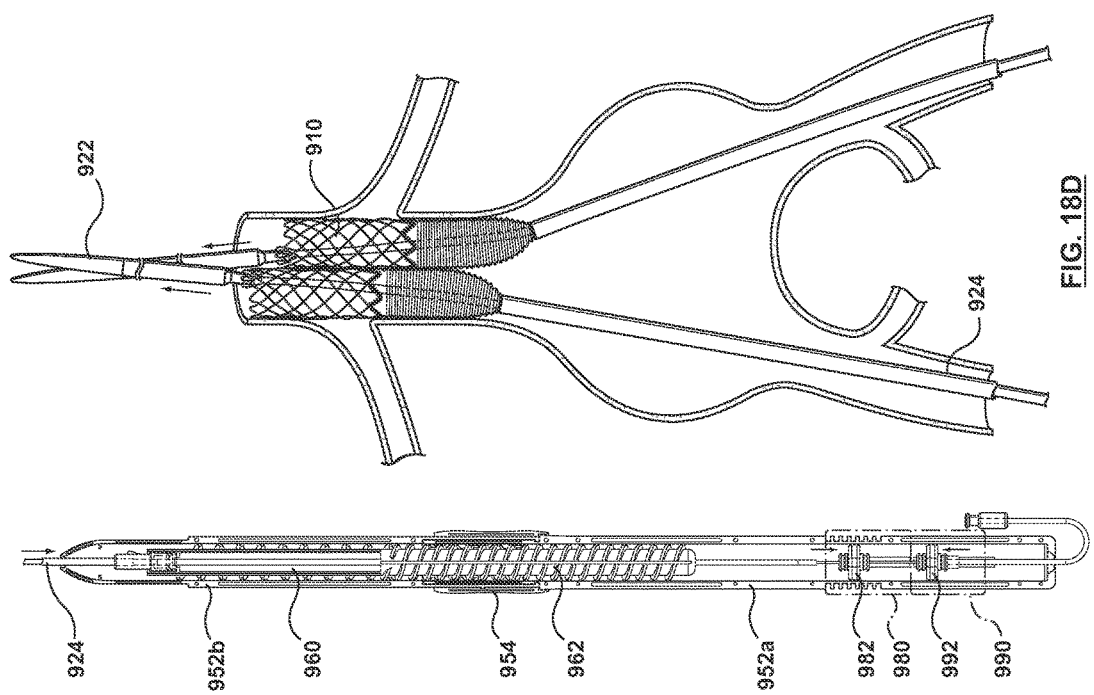

STENT DELIVERY SYSTEMS AND ASSOCIATED METHODS

CROSS-REFERENCE TO RELATED APPLICATIONS

The present application claims priority to each of the following U.S. Provisional Patent Applications:

(A) U.S. Provisional Patent Application No. 61/681,907, filed on Aug. 10, 2012 and entitled "HANDLE ASSEMBLIES FOR STENT GRAFT DELIVERY SYSTEMS AND ASSOCIATED SYSTEMS AND METHODS"; and (B) U.S. Provisional Patent Application No. 61/799,591, filed Mar. 15, 2013 and entitled "HANDLE ASSEMBLIES FOR STENT GRAFT DELIVERY SYSTEMS AND ASSOCIATED SYSTEMS AND METHODS."

Each of the foregoing applications is incorporated herein by reference in its entirety.

TECHNICAL FIELD

The present technology relates to treatment of abdominal aortic aneurysms. More particularly, the present technology relates to handle assemblies for stent graft delivery systems and associated systems and methods.

BACKGROUND

An aneurysm is a dilation of a blood vessel of at least 1.5 times above its normal diameter. The dilated vessel forms a bulge known as an aneurysmal sac that can weaken vessel walls and eventually rupture. Aneurysms are most common in the arteries at the base of the brain (i.e., the Circle of Willis) and in the largest artery in the human body, the aorta. The abdominal aorta, spanning from the diaphragm to the aortoiliac bifurcation, is the most common site for aortic aneurysms. Such abdominal aortic aneurysms (AAAs) typically occur between the renal and iliac arteries, and are presently one of the leading causes of death in the United States.

The two primary treatments for AAAs are open surgical repair and endovascular aneurysm repair (EVAR). Surgical repair typically includes opening the dilated portion of the aorta, inserting a synthetic tube, and closing the aneurysmal sac around the tube. Such AAA surgical repairs are highly invasive, and are therefore associated with significant levels of morbidity and operative mortality. In addition, surgical repair is not a viable option for many patients due to their physical conditions.

Minimally invasive endovascular aneurysm repair (EVAR) treatments that implant stent grafts across aneurysmal regions of the aorta have been developed as an alternative or improvement to open surgery. EVAR typically includes inserting a delivery catheter into the femoral artery, guiding the catheter to the site of the aneurysm via X-ray visualization, and delivering a synthetic stent graft to the AAA via the catheter. The stent graft reinforces the weakened section of the aorta to prevent rupture of the aneurysm, and directs the flow of blood through the stent graft away from the aneurismal region. Accordingly, the stent graft causes blood flow to bypass the aneurysm and allows the aneurysm to shrink over time.

Most stent and stent graft systems for cardiovascular applications (e.g., coronary, aortic, peripheral) utilize self-expanding designs that expand and contract predominantly in the radial dimension. However, other system include braided stent grafts that are delivered in a radially compressed, elongated state. Upon delivery from a delivery catheter, the stent graft will radially expand and elastically shorten into its free state. In other words, the effective length of the stent graft changes as its diameter is forced smaller or larger. For example, a stent graft having a shallower, denser helix angle will result in a longer constrained length. Once the stent graft is removed from a constraining catheter, it can elastically return to its natural, free length.

Delivering a stent graft to an artery requires accurate and precise positioning of the stent graft relative to a target location in the destination artery. For example, a misplaced stent graft can block flow to a branching artery. Some stent graft delivery systems utilize one or more markers (e.g., radiopaque markers) to establish the alignment of the stent graft relative to the artery wall. However, the location of the radiopaque markers on the stent graft can move relative to an initial marker position because of the change in the stent graft's effective length upon deployment, as described above. Accordingly, after deployment of a stent graft, the stent graft (e.g., its proximal or distal edge) may miss the target point in the artery. Therefore, there are numerous challenges associated with the accurate positioning of stent grafts that change dimensions in both the radial and longitudinal directions.

BRIEF DESCRIPTION OF THE DRAWINGS

FIGS. 2B and 2C are side views of a delivery catheter of a stent graft delivery system configured in accordance with an embodiment of the technology.

FIGS. 2D and 2E are side views of collets of a stent graft delivery system configured in accordance with an embodiment of the technology.

FIGS. 3A-3C are side views of a delivery catheter of a stent graft delivery system configured in accordance with an embodiment of the technology.

FIGS. 5A and 5B are partial side views of a handle assembly and a housing, respectively, configured in accordance with various embodiments of the technology.

FIG. 8A is an isometric view of a handle assembly configured in accordance with another embodiment of the technology.

FIGS. 10A and 10B are side and partial cut-away views, respectively, of a handle assembly configured in accordance with another embodiment of the technology.

FIGS. 16A and 16B are partially schematic representations of a method of stent graft delivery in accordance with an embodiment of the technology.

FIG. 17 is a partially schematic representation of a method of stent graft delivery in accordance with an embodiment of the technology.

FIGS. 18A-18E illustrate a stent delivery method in accordance with an embodiment of the technology.

DETAILED DESCRIPTION

The present technology is directed toward handle assemblies for stent delivery systems and associated systems and methods. Certain specific details are set forth in the following description and in FIGS. 1A-19C to provide a thorough understanding of various embodiments of the technology. For example, many embodiments are described below with respect to the delivery of stent grafts that at least partially repair AAAs. In other applications and other embodiments, however, the technology can be used to repair aneurysms in other portions of the vasculature. Furthermore, the technology can be used to deliver a stent for any suitable purpose in any suitable environment. Other details describing well-known structures and systems often associated with stent grafts and associated delivery devices and procedures have not been set forth in the following disclosure to avoid unnecessarily obscuring the description of the various embodiments of the technology. Many of the details, dimensions, angles, and other features shown in the Figures are merely illustrative of certain embodiments of the technology. For example, dimensions shown in the Figures are representative of particular embodiments, and other embodiments can have different dimensions. A person of ordinary skill in the art, therefore, will accordingly understand that the technology may have other embodiments with additional elements, or the technology may have other embodiments without several of the features shown and described below with reference to FIGS. 1A-19C.

In this application, the terms "distal" and "proximal" can reference a relative position of the portions of an implantable stent graft device and/or a delivery device with reference to an operator. Proximal refers to a position closer to the operator of the device, and distal refers to a position that is more distant from the operator of the device. Also, for purposes of this disclosure, the term "helix angle" refers to an angle between any helix and a longitudinal axis of the stent graft.

1. Selected Embodiments of Stent Delivery Systems

Figure 1A:
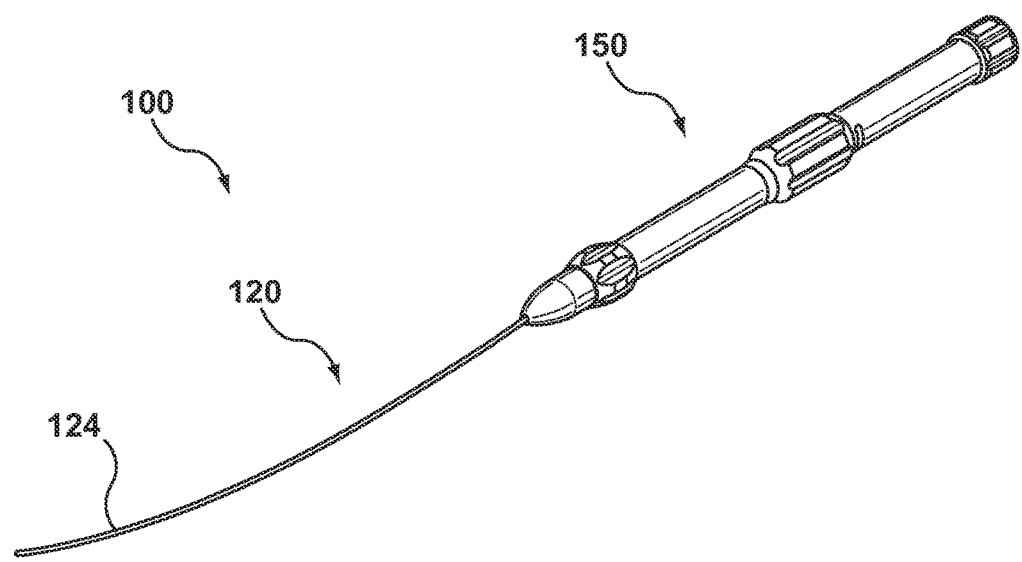
FIG. 1A is an isometric view of a stent graft delivery system configured in accordance with an embodiment of the technology.
Figure 1B:
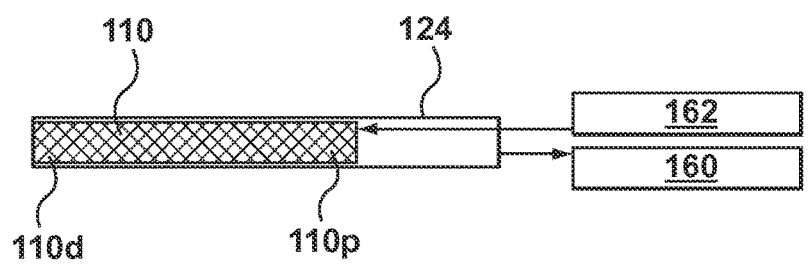
FIGS. 1B and 1C are functional schematic diagrams of a portion of a handle assembly system configured in accordance with embodiments of the technology.
Figure 1C:
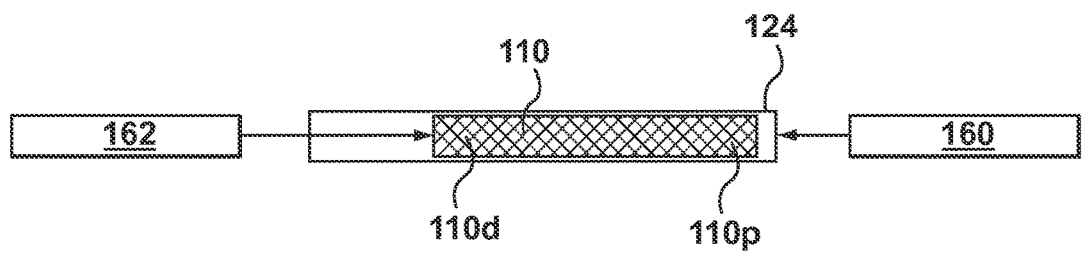

As shown in FIGS. 1A-1C, various embodiments of a stent delivery system 100 can include a delivery catheter 120 having a shaft or tubular enclosure 124 on a distal end portion of the catheter 120, a braided stent 110 (FIGS. 1B and 1C) constrained within the tubular enclosure 124, and a handle assembly 150 at a proximal end portion of the delivery catheter 120. Various embodiments of the technology may be used to deliver the braided 110 stent to a target area within a body lumen of a human. For example, one embodiment of the stent delivery system 100 can be configured to deploy a stent at a target location in an aorta such that at least a portion of the stent is superior to an aortic aneurysm. As another example, another embodiment of the stent delivery system 100 can be configured to deploy a stent at a target location in an iliac artery such that at least a portion of the stent is inferior to an aortic aneurysm. Further embodiments of the technology may be used to deliver a stent to any suitable target area.

1.1 Selected Embodiments of Delivery Catheters and Stents

The delivery catheter 120 of various embodiments can include a distal end portion insertable into a body lumen within a human and navigable toward a target area, and nested components configured to mechanically communicate actions of the handle assembly 150 to distal end portion of the delivery catheter 120. The stent 110 (FIGS. 1B and 1C) can be constrained in a radially compressed state at the distal end portion of the delivery catheter 120. In some embodiments, the delivery catheter 120 has a diameter of approximately 14 Fr, but in other embodiments the delivery catheter 120 can have a greater diameter or a smaller diameter, such as 10 Fr or 8 Fr.

Selected Embodiments of Distal End Portions of Delivery Catheters

Figure 2A:
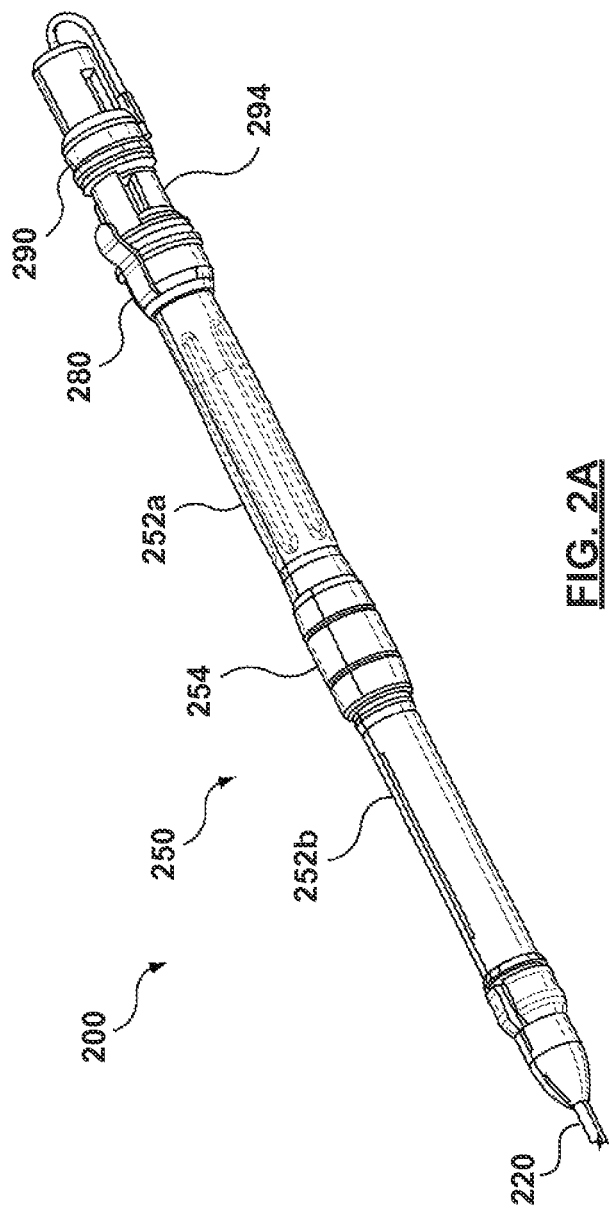
FIG. 2A is an isometric view of a handle assembly configured in accordance with an embodiment of the technology.
Figure 4A:
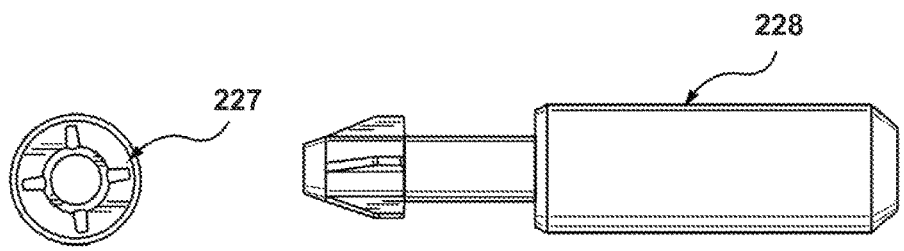
FIGS. 4A-4E are front and side views of collets of a stent graft delivery system configured in accordance with various embodiments of the technology.
Figure 4B:
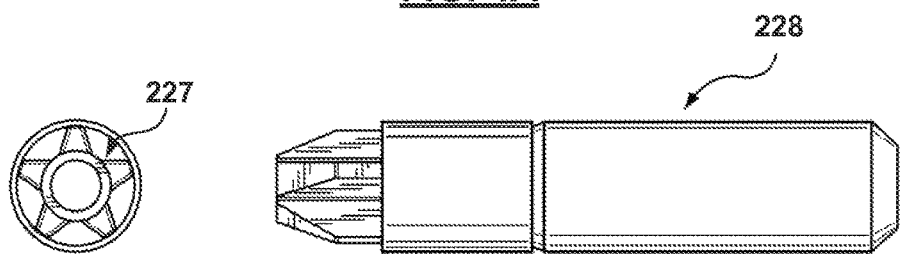
Figure 4C:
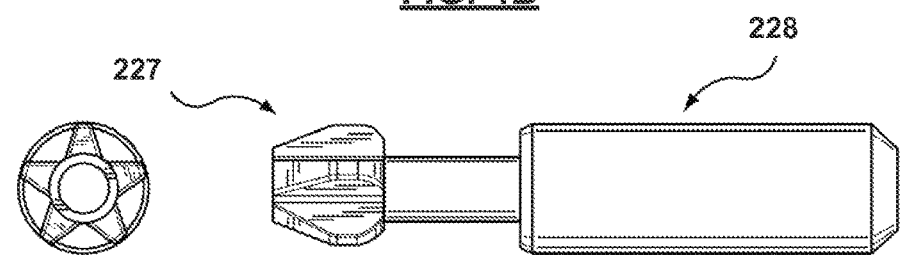
Figure 4D:
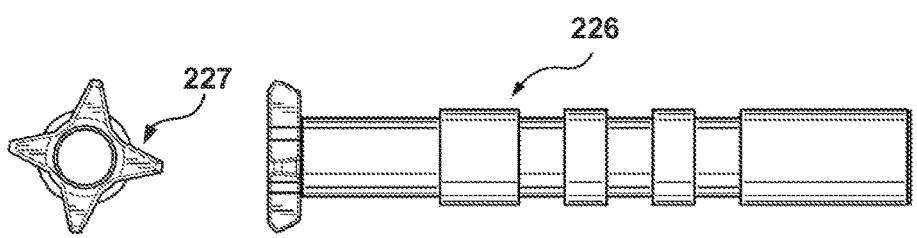
Figure 4E:
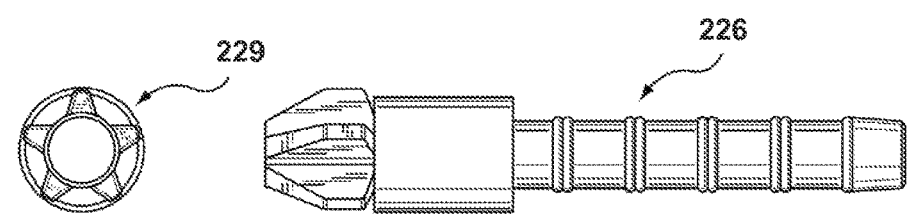

FIGS. 2A-2E illustrate an embodiment of a stent delivery system 200 configured in accordance with another embodiment of the technology, and FIGS. 3A-3C illustrate portions of a delivery catheter 220 of the stent delivery system 200 of FIGS. 2A-2C. As shown in FIG. 2A, the stent delivery system 200 can include the delivery catheter 220 and handle assembly 250 operably coupled to the delivery catheter 220. As shown in FIGS. 2B, 2C, and 3A-3C, the distal end portion of delivery catheter 220 includes a distal top cap 222 and an outer sheath 224 that engage a stent 210. More specifically, the distal top cap 222 covers and constrains at least a distal end portion 210d of the stent 210 in a radially compressed configuration, and the outer sheath 224 covers and constrains at least a proximal end portion 210p of the stent 210 in a radially compressed configuration. In some embodiments, the top cap 222 and outer sheath 224 can overlap or meet edge-to-edge so as to entirely cover the stent 210, though in other embodiments the top cap 222 and outer sheath 224 can leave a medial portion of the stent 210 uncovered. The top cap 222 can have a tapered distal end to help navigate the catheter through a patient's vasculature, and/or a radiused proximal edge that may reduce snagging or catching on vasculature or other features during catheter retraction after stent deployment.

FIGS. 11A-12D show an embodiment of a delivery system 400 configured in accordance with another embodiment of the technology. Similar to the stent delivery system 200 of FIGS. 2A-2E, the stent delivery system 400 of FIGS. 11A-12D can include a delivery catheter 420 and handle assembly 450 operably coupled to the delivery catheter 420. As shown in FIGS. 11B and 11C, the distal end portion of the delivery catheter 420 can include a distal top cap 424 having a tubular enclosure that covers and constrains the entirety of the stent 410 in a radially compressed configuration. Removing the top cap 424 in a distal direction can expose the stent 410. Similar to the top cap 222 shown in FIGS. 2B and 2C, the top cap 424 can have a tapered distal end and/or radiused proximal edge.

Other embodiments of delivery catheters can have distal end portions that include an outer sheath that covers and constrains the entirety of the stent in a radially compressed configuration such that retraction of the outer sheath in a proximal direction exposes the stent. Furthermore, in some embodiments, the top cap 222, 424 and/or the outer sheath can include radiopaque markers that provide visual aids for device positioning during deployment procedures. Such radiopaque markers can be helical, circumferential rings, and/or have any other suitable form. Additionally, in some embodiments, the top cap 222, 424 and/or the outer sheath can include structural reinforcements, such as filaments, to discourage deformation in tension or compression. For example, axially-oriented filaments can be interwoven or otherwise coupled to the top cap 222, 424 or outer sheath such that the top cap 222, 424 or outer sheath is stretch-resistant and facilitates smooth, predictable actuation by the various nested components described below. As another example, the top cap 222, 424 and/or outer sheath can include other reinforcements to increase column strength and discourage buckling during actuation by the various nested components.

Selected Embodiments of Stents and Collets

As shown in, for example, FIG. 2B, the stent 210 can be disposed at the distal end portion of the delivery catheter 220. The stent 210 can be a bare stent or a stent graft, such as those described in U.S. Application Patent Publication No. 2011/0130824, which is incorporated herein by reference in its entirety. In other embodiments, the stent 210 can be any suitable braided stent or other self-expanding stent. As described above, the stent 210 can be constrained in a radially compressed configuration by the top cap 222 and/or an outer sheath. Additionally, as shown in FIG. 2C, prior to stent deployment, the stent (not shown) can be axially constrained at the distal end portion of the delivery catheter 220 with one or more collets 226, 228 coupled to one or more nested components of the delivery catheter 220.

FIGS. 4A-4E are front and side views of various collets 226, 228 that are configured to couple stents to the distal end portion of the delivery catheter 220 (FIG. 2C). Generally, the collets 226 and 228 can each include a fluted portion with circumferentially distributed prongs 227, each of which engages an opening on a stent and constrains the longitudinal position of the stent at the point of engagement. Each prong 227 can have a radius of curvature that matches that of the stent it is configured to engage and a height that exceeds the height of the stent wire by a suitable amount so as to help ensure engagement with the stent. For example, the prongs 227 may have a height about 1.5 times the height of the stent wire. In other embodiments, the prongs 227 may have other suitable heights. The number, arrangement, and particular prong profiles can be suitably tailored to the specific application. For example, the collets 226 and 228 can include an angled tip, a 5-point angled tip, a rounded tip that reduces or eliminates friction or undesirable catching on the stent wire, and/or a spring 229 (FIG. 4E) that assists in launching the stent wire into radial expansion during stent deployment.

Delivery systems in accordance with the present technology can include a trailing or proximal collet 226 (FIGS. 4D and 4E) coupled to a proximal end portion of a stent, a leading or distal collet 228 (FIGS. 4A-4C) coupled to a distal end portion of the stent, or both the trailing collet 226 and the leading collet 228. In other embodiments, individual collets can be coupled to other suitable portions of a stent (e.g., a medial portion of a stent). As shown in FIGS. 11B and 11C, in further embodiments one or more end portions of a stent can be coupled to the distal end portion of the delivery catheter 420 with a smooth, prongless docking tip 426.

Selected Embodiments of Nested Components

Nested components along the delivery catheters 220 and 420 described above can be configured to mechanically control aspects of the distal end portion of the delivery catheter. In various embodiments, each of the nested components can be configured to longitudinally move independently of the other nested components, whereas in other embodiments two or more nested components can temporarily or permanently be locked together to permit movement in tandem. At least portions of the nested components outside of a handle assembly (e.g., the handle assemblies 250 and 450) can be sufficiently flexible to permit navigation and advancement through potentially tortuous paths through a blood vessel, though the degree of flexibility can vary depending on the application (e.g., the location of the target site and/or the path to the target site). The nested components can include a plurality of tubes and/or wires that are configured to push and/or pull various components of the distal end portion of the delivery catheter. As a person of ordinary skill in the art would appreciate, although the components of the delivery catheters 220 and 420 are described herein as "nested", in other embodiments the delivery catheters 220 and 420 can include similar operative components arranged laterally offset from one another.

Figure 6A:
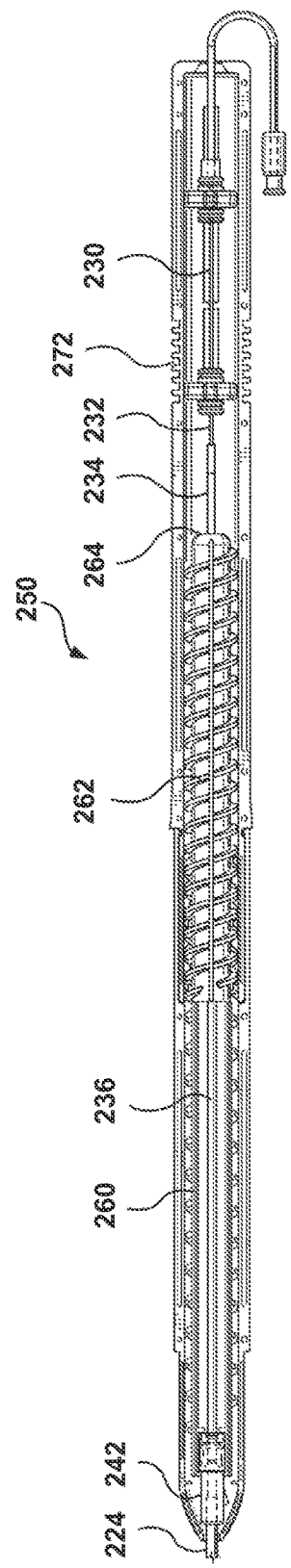
FIG. 6A is a partial cut-away view of a handle assembly configured in accordance with an embodiment of the technology.

FIG. 2C shows an embodiment of the delivery catheter 220 in which the nested components include a tip tube 230, an inner shaft 232, and a dilator 236, although in other embodiments the delivery catheter 220 can include any suitable number of tubes and/or shafts. As shown in FIGS. 6A and 6C, in various embodiments, the nested components can further include one or more stiffeners 234 disposed within and/or around other nested components. The stiffener 234 can, for example, axially reinforce a portion of a pushing component (e.g., the inner shaft 232) to increase the column strength of the pushing component. The stiffener 234 can be made of stainless steel or any other suitably rigid material. In the embodiment shown in FIGS. 2C and 6A, the tip tube 230 is disposed within the inner shaft 232, and the inner shaft 232 is disposed within the dilator 236, with the stiffener 234 (FIG. 6A) surrounding and reinforcing portions of the tip tube 230 and the inner shaft 232 within the handle assembly 250.

In the embodiment shown in FIGS. 2B and 2C, the tip tube 230 is operatively connected to the top cap 222 such that proximal and distal movement of the tip tube 230 corresponds to longitudinal movement of the top cap 222. For example, sufficient distal movement of the tip tube 230 can cause the top cap 222 to move distally enough to release the distal end portion 210d of the stent 210, thereby allowing the distal end portion 210d of the stent 210 to self-expand. In some embodiments, the tip tube 230 can be made of stainless steel, and in other embodiments the tip tube 230 can additionally or alternatively include any other suitable materials. Furthermore, the tube 230 can include suitable structural reinforcing features, such as a stainless steel braid.

In the embodiment shown in FIGS. 2A-2E, the inner shaft 232 is operatively connected to the leading collet 228, engaged with the distal end portion 210d of the stent 210 such that proximal and distal movement of the inner shaft 232 corresponds to longitudinal movement of the leading collet 228 and distal end portion 210d of the stent 210. In other embodiments, the inner shaft 232 can be in mechanical communication with the distal end portion 210d of the stent 210 in other suitable manners. The inner shaft 232 can permit, within its lumen, telescopic movement of the tip tube 230, thereby allowing longitudinal movement of the top cap 222 relative to the leading collet 228. The inner shaft 232 can be a tube made of polyimide and/or other suitable materials.

In the embodiment shown in FIG. 2C, the dilator 236 is operatively connected to the trailing collet 226, which is in turn engaged with the proximal end portion 210p of the stent 210 such that proximal and distal movement of the dilator 236 corresponds to longitudinal movement of the trailing collet 226 and the proximal end portion 210p of the stent 210. The dilator 236 can permit, within its lumen, telescopic movement of the tip tube 230 and the inner shaft 232. In turn, the outer sheath 224 can permit, within its lumen, the telescopic movement of the dilator 236. Accordingly, the top cap 222, the leading collet 228, and the trailing collet 226 may move relative to one another corresponding to relative movement of the tip tube 230, the inner shaft 232, and the dilator 236, respectively. The dilator 236 can be made from nylon and/or various other suitable materials.

In certain embodiments, the nested components described above with respect to FIGS. 2C, 6A, and 6C can be used to deliver a stent to an aorta before an aneurysm. In other embodiments, the nested components can be used to deliver stents to other blood vessels, such as the iliac arteries.

Figure 11A:
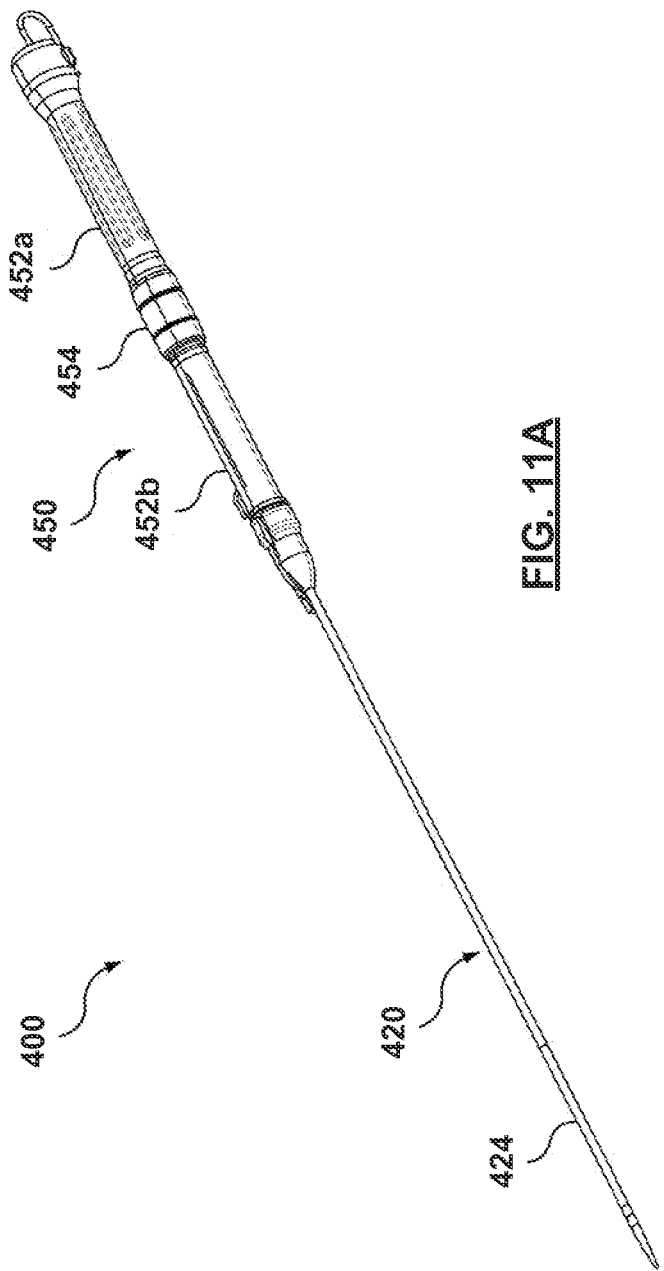
FIG. 11A is an isometric view of a stent graft delivery system configured in accordance with another embodiment of the technology.
Figure 11B:
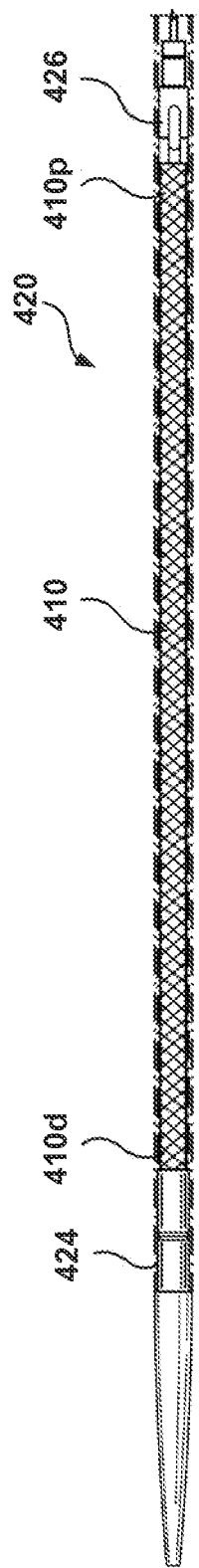
FIGS. 11B and 11C are side views of a delivery catheter of the stent graft delivery system of FIG. 11A configured in accordance with an embodiment of the technology.
Figure 11C:
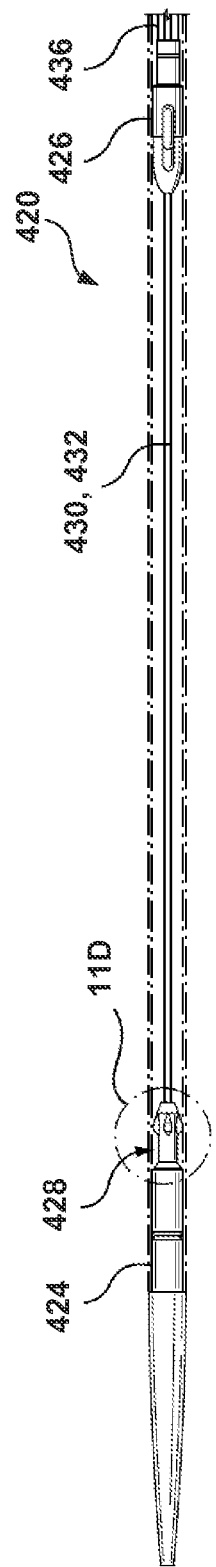
Figure 11D:
FIG. 11D is a side view of a collet of the a stent graft delivery system of FIG. 11A configured in accordance with an embodiment of the technology.
Figure 12A:
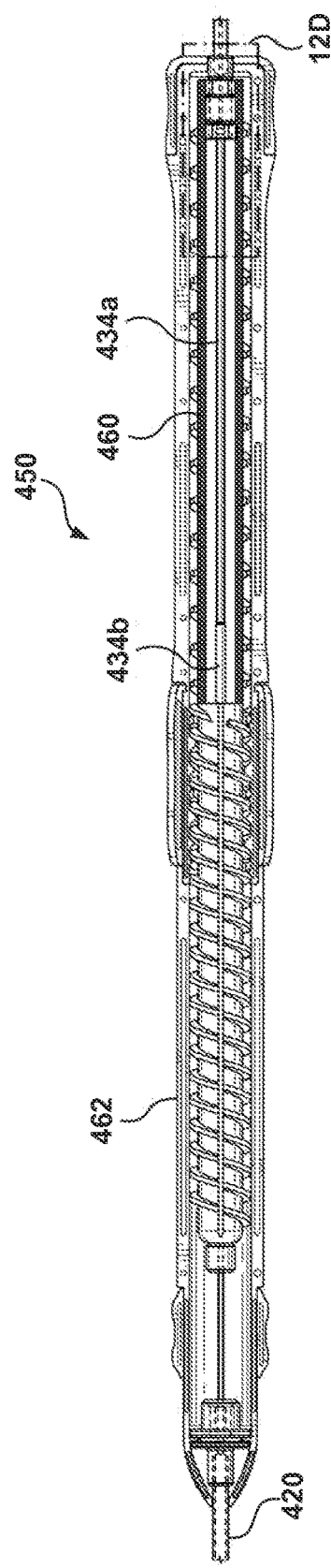
FIG. 12A is a partial cut-away view of a handle assembly configured in accordance with an embodiment of the technology.
Figure 12B:
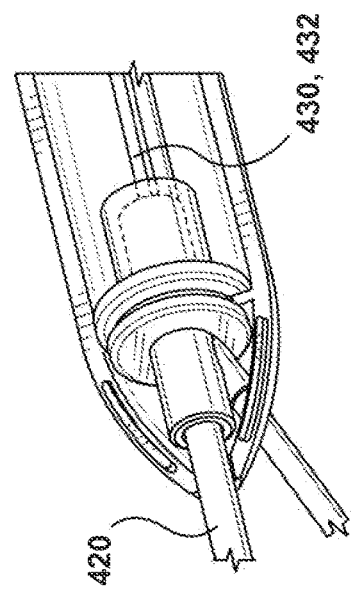
FIGS. 12B-12D are enlarged partial cut-away views of portions of the handle assembly of FIG. 12A.

FIGS. 11A-11C show another embodiment of the delivery catheter 420 in which the nested components include a tip tube 430, an inner shaft 432, and a dilator 436, although in other embodiments the delivery catheter 420 can include any suitable number of tubes and/or shafts. As shown in FIGS. 12A and 12D, the nested components can additionally include one or more stiffeners (identified individually as a first stiffener 434a and a second stiffener 434b, and referred to collectively as stiffeners 434) disposed within and/or around other nested components. Similar to the embodiment of FIG. 6A, the stiffeners 434 can, for example, reinforce a pushing component for increased column strength of that pushing component. The stiffeners 434 can be made of stainless steel or any other suitably rigid material. In the embodiment shown in FIG. 11C, a portion of the tip tube 430 is disposed within the inner shaft 432, and another portion of the tip tube 430 is disposed within the dilator 436. As shown in FIG. 12A, the first and second stiffeners 434a and 434b can surround and reinforce another portion of the tip tube 430 within the handle assembly 450. In other embodiments, however, the nested components can be configured in any suitable arrangement. Furthermore, some or all of the nested components can be replaced or supplemented with wires or other suitable control mechanisms.

In the embodiment of FIGS. 11A-12B, the tip tube 430 is operatively connected to the top cap 424 such that the proximal and distal movement of the tip tube 430 corresponds to longitudinal movement of the top cap 424. In particular, sufficient distal movement of the tip tube 430 can cause the top cap 424 to move distally enough to release the stent 410, thereby allowing the stent to self-expand. The tip tube 430 can be made of stainless steel and/or other suitable materials. Furthermore, the tube 430 can include suitable structural reinforcing features, such as a stainless steel braid.

As further shown in the embodiment of FIGS. 11A-12B, the inner shaft 432 is operatively connected to the leading collet 428, which is in turn engaged with the distal end portion 410d of the stent 410 such that proximal and distal movement of the inner shaft 432 corresponds to longitudinal movement of the leading collet 428 and the distal end portion 410d of the stent 410. In other embodiments, the inner shaft 432 can be in mechanical communication with the distal end portion 410d of the stent 410 in any suitable manner. Within its lumen, the inner shaft 432 can permit telescopic movement of the tip tube 430. The inner shaft 432 can be a tube made of polyimide and/or other suitable materials.

As shown in FIG. 11C, the dilator 436 can be coupled to a docking tip 426, which engages with the proximal end portion 410p of the stent 410 at the distal end portion of the delivery catheter 420. Within its lumen, the dilator 436 can permit telescopic movement of the inner shaft 432 and the tip tube 430. The dilator 436 is made of nylon and/or other suitable materials.

In certain embodiments, the nested components described above with respect to FIGS. 11A-12B can be used to deliver a stent to an iliac artery after an aneurysm. In other embodiments, the nested components can be used to deliver stents to other blood vessels, such as the aorta.

Though the above embodiments are described in detail with particular arrangements of nested components, in other embodiments the nested components can be configured in any suitable arrangement. Additionally, other embodiments can include any suitable number of nested push/pull components. Furthermore, some or all of the nested components can be replaced or supplemented with wires or other suitable control mechanisms.

1.2 Selected Embodiments of Handle Assemblies

Various embodiments of handle assemblies can be used in conjunction with other aspects of the stent delivery systems 200 and 400 as described above, but can additionally or alternatively be used to deploy any suitable stent or stent graft constrained within a tubular enclosure of a delivery catheter in a radially compressed, elongated state. In particular, as described in further detail below and demonstrated in the functional diagrams of FIGS. 1B and 1C, the handle assembly 150 of FIG. 1A can incorporate various mechanisms to effectuate the opposing displacement of an uncovering component 160 and a position compensating component 162 at a predetermined payout ratio, which deploys the stent 110 in a controlled manner. The uncovering component or element 160 can also configured to expose the stent 110 from the tubular enclosure 124 and allow the exposed portion of stent 110 to radially self-expand. The position compensating component 162 provides an axially compressive force on the stent 110 that counteracts the longitudinal displacement otherwise resulting from changing stent length as the stent 110 radially expands. Generally speaking, as shown in FIG. 1B, the position compensating component 162 can actuate in a distal direction while the uncovering element 160 can actuate in a proximal direction. Alternatively, as shown in FIG. 1C, the positioning compensating component 162 can actuate in a proximal direction while the uncovering component 160 can actuate in a distal direction.

The synchronized motion of the uncovering component 160 and the position compensating component 162 can control the axial position of the exposed portion of the stent 110. When the ratio of the components' movements is matched to or corresponds to the helix angle of the stent 110, the position of the deployed stent 110 can be maintained relative to a particular destination target location. Although in many applications it is desirable that at least one end of the stent 110 remain stationary during deployment, in some alternative applications it might be desirable to modify the predetermined payout ratio so that the exposed portion of the stent 110 moves in a controlled manner at a predetermined rate.

Selected Embodiments of Lead Screws

FIGS. 5A-12D illustrate various handle assemblies with lead screws configured in accordance with embodiments of the technology. For instance, as shown in FIGS. 5A and 5B, various embodiments of a handle assembly for delivering a stent from a tubular enclosure (e.g., the tubular enclosure 124 of FIG. 1A) can include a first lead screw 260, a second lead screw 262, and a housing 270 surrounding at least a portion of each of the first and second lead screws 260 and 262. The first lead screw 260 has a lead thread of a first pitch and a first handedness (i.e., the lead screw has a right-handed or left-handed thread), and is coupled to the tubular enclosure. The second lead screw 262 has a lead thread of a second pitch and a second handedness different from the first handedness, and is coupled to the stent. The housing 270 surrounds at least a portion of each of the first and second lead screws 260 and 262, and defines two housing threads, including a first housing thread 276 with the same pitch and handedness as the first lead screw 260 and a second housing thread 278 with the same pitch and handedness as the second lead screw 262. The housing 270 and lead screws 260, 262 can be configured to cooperate such that upon rotation of at least a portion of the housing around a longitudinal axis, the first housing thread 276 engages the first lead screw 260 and second housing thread 278 engages the second lead screw 262. The engagements between the housing threads 276, 278 and the lead screws 260, 262 induce simultaneous translations of the first and second lead screws 260 and 262 in opposite directions along a longitudinal axis A-A (FIG. 5A) of the housing 270, and the simultaneous translations deploy the stent from the tubular enclosure. In particular, translation of the first lead screw 260 can cause the tubular enclosure to translate to expose the stent and allow the exposed portion of the stent to radially self-expand. At the same time, translation of the second lead screw 262 can apply an axially compressive force to the stent that substantially avoids or counterbalances longitudinal displacement of the end of the stent that is initially exposed.

As shown in FIGS. 5A-12D, various embodiments of handle assemblies can include first and second lead screws that have different handedness such that their rotation in the same direction induces their movement in opposite directions. For example, the first lead screw can have a right-handed thread, and the second lead screw can have a left-handed thread. Alternatively, the first lead screw can have a left-handed thread, and the second lead screw can have a right-handed thread. Since the first and second lead screws have threads of opposite handedness, their concurrent rotation in the same direction will induce their translations in opposite directions. Additionally, the threads of lead screws can be external threads (e.g., as shown in FIG. 5A) or internal threads.

Furthermore, as shown in FIGS. 5A-12D, the first and second lead screws in various embodiments of the handle assembly can have different thread pitches such that their concurrent rotation induces their movement at different rates of travel. As shown in FIG. 5A, for example, the first lead screw 260, which is in mechanical communication with the tubular enclosure, can have a relatively coarse thread pitch, and the second lead screw 262, which is in mechanical communication with the proximal or distal end portion of the stent, can have a relatively fine thread pitch. Alternatively, the first lead screw 260 can have a relatively fine thread pitch, while the second lead screw 262 can have a relatively coarse thread pitch, or the first and second lead screws 260 and 262 can have substantially equal thread pitches. The ratio of thread pitches corresponds to a predetermined payout ratio of the first and second lead screws 260 and 262 and, in various embodiments, can correspond to the braid angle of the stent. In certain embodiments, for example, the ratio of the coarse thread (e.g., on the first lead screw 260) to the fine thread (e.g., on the second lead screw 262) is approximately 1.5:1. Payout ratios ranging from about 1:1 to about 2:1 have also been shown to provide acceptable stent deployment. In other embodiments, the payout ratio of the first and second lead screws 260 and 262 can differ depending on the application. For example, both the first and second lead screws 260 and 262 can have relatively fine thread pitches that may allow for precise deployment, since a fine lead screw axially translates less distance per rotation than a coarse lead screw would for the same rotation. In this manner, the specific pitches and/or the ratio of the pitches can be selected to achieve a particular degree of mechanical advantage, a particular speed and precision of stent deployment, and/or a selected predetermined payout ratio.

As shown in FIGS. 5A-12D, the first and second lead screws can have cross-sections that enable them to longitudinally overlap and slide adjacent to each other along the longitudinal axis of the handle. As shown in FIG. 5A, for example, at least the threaded lengths of the lead screws 260, 262 are "half" lead screws, each having an approximately semi-circular cross-section and arranged so that the lead screws 260, 262 are concentric. When mated longitudinally, the semi-circular cross-sections cooperate to define a lumen through which various push/pull tubes, wires, and/or other suitable mechanisms for stent deployment can travel and extend distally into the delivery catheter. In other embodiments, the first and second lead screws 260 and 262 can have other complementary arcuate cross-sections, and/or other suitable cross-sectional shapes.

In various embodiments, the lead screws 260 and 262 can have an initial offset arrangement prior to stent deployment such that the first and second lead screws 260 and 262 have no longitudinal overlap within the housing 270 or overlap for only a portion of the length of the lead screws 260, 262. Upon rotation of the housing 270, the lead screws 260, 262 can translate relative to one another to increase their longitudinal overlap. In certain embodiments, for example, the lead screws 260, 262 in the initial offset arrangement have an initial overlap area of approximately five to nine centimeters (e.g., seven centimeters). In operation, the handle assembly can be configured such that rotation of the housing 270 during the course of stent deployment induces the first lead screw 260 (and movement of the tubular enclosure coupled thereto) to axially translate a distance of approximately 15 to 25 centimeters relative to its position in the initial offset arrangement. Additionally, the handle assembly can be configured such that rotation of the housing during the course of stent deployment induces the second lead screw 262 (and movement of the associated end of the stent) to axially translate a distance of approximately 5 to 15 centimeters. For example, in one embodiment the second lead screw 262, which is in mechanical communication with an end of the stent, is configured to shorten the length of the stent (relative to the length of the stent in its elongated radially compressed configuration) by approximately 25% to 75% (e.g., approximately 50%). In other embodiments, the degree of change in the stent length pre-deployment to post-deployment can differ depending on the specific application. In other embodiments, rotation of the housing 270 during stent deployment can cause the first lead screw 262 to axially translate more than 25 centimeters or less than 15 centimeters from its initial position, and cause the second lead screw 262 to axially translate more than 15 centimeters or less than 5 centimeters from its initial position.

In various embodiments, the first and second lead screws 260 and 262 can define additional mating features to facilitate mutual alignment. For example, one lead screw (e.g., the first lead screw 260) can define a longitudinal key or spline that slidingly engages with a longitudinal slot on the other lead screw (e.g., the second lead screw 262) such that the lead screws maintain longitudinal alignment with each other as the lead screws longitudinally translate past one another. In other embodiments, one or both lead screws can include other suitable alignment features.

The first and second lead screws 260 and 262 can be made of injection molded plastic of suitable column strength and overall torsional rigidity to bear axial loads and/or torsional loads during stent deployment. In other embodiments, the lead screws 260, 262 can additionally or alternatively include other suitable materials that are milled, turned, casted, and/or formed in any suitable manufacturing process to create the threads and other associated features of the lead screws 260, 262. The lead screws 260, 262 can additionally or alternatively meet predetermined load requirements by including particular thread types (e.g., acme threads or other trapezoidal thread forms) and/or material reinforcements. In some embodiments, the plastic material is of a formulation including a lubricant for low-friction thread engagement, such as LUBRILOY® D2000. Furthermore, suitable external lubricants can additionally or alternatively be applied to the lead screws 260, 262 to help ensure smooth engagement of the threads.

As shown in FIGS. 5A-12D, in various embodiments of the handle assembly, the housing can include a stationary portion and rotatable shaft portion. As shown in FIG. 5A, for example, the housing 270 can include a first or rotatable shaft portion 252a and a second or stationary portion 252b coupled to one another and secured by a locking collar 254. Though the first shaft portion 252a is referred to herein as the "rotatable shaft portion 252a" of the housing 270 and the second shaft portion 252b is referred to as the "stationary shaft portion 252b", it should be understood that in other embodiments either the first or second shaft portion 252a or 252b can be rotated in an absolute frame of reference, and/or rotated relative to the other shaft portion 252a, 252b. As shown in FIG. 5B, the rotatable shaft portion 252a can define housing the first and second housing threads 276 and 278 that are configured to threadingly engage with corresponding threads on lead screws 260 and 262. Accordingly, rotation of the rotatable shaft portion 252a relative to the stationary shaft portion 252b can cause the first and second threads 276 and 278 to engage the corresponding threads on lead screws 260 and 262, and therefore cause the first and second lead screws 260 and 262 to axially translate. In other embodiments, any suitable portion of the housing 270 can define the threads 276 and 278. Similarly, FIG. 11A illustrates another embodiment in which the housing 470 includes a first or rotatable shaft portion 452a and a second or stationary portion 452b that are coupled to one another and secured by a locking collar 454.

In some embodiments, as shown in FIG. 5B, the housing 270 defines internal threads configured to engage with the externally threaded lead screws 260, 262 (FIG. 5A). In other embodiments, the housing 270 can define external threads configured to engage with internally threaded lead screws. In some embodiments, as shown in FIGS. 5A and 5B, the stationary shaft portion 252b (or another suitable part of housing 270) can include one or more keyway splines 279 (FIG. 5B), and/or any other suitable key mechanism. Each keyway spline 279 can engage a respective axial groove 269 (FIG. 5A) in one of the lead screws 260, 262 to prevent rotation of the lead screws 260, 262 when the rotatable shaft portion 252a rotates, thereby substantially constraining the lead screws 260, 262 to axial translation only.

The housing 270 can include shell pieces that mate and couple to one another to form the stationary shaft portion 252b and the rotatable shaft portion 252a. The shell pieces can define keys and/or other interlocking or alignment features to properly mate and form a volume or enclosure that is configured to house or otherwise contain the first and second lead screws 260 and 262 and/or other catheter components. The shell pieces can be snap fit together, attached by screws and/or other mechanical fasteners, and/or otherwise joined. Similar to the first and second lead screws 260 and 262, the portions of the housing 270 can be composed of a suitable rigid plastic formed by injection molding. In other embodiments, the housing 270 can additionally or alternatively include any other suitable materials and/or be formed by casting, turning, milling, and/or any other suitable manufacturing process. In various embodiments, the housing 270 can be made of a lubricious plastic material and/or coated with external lubricant to facilitate smooth thread engagement with the lead screws 260, 262 and relative rotation between the rotating and stationary shaft portions 252a and 252b of the housing 270.

FIGS. 6A-6E show an embodiment of the handle assembly 250 with the first and second lead screws 260 and 262. In this embodiment, the handle assembly 250 is configured to deploy, from the outer sheath 224 or other tubular enclosure, a distal end of the stent (not shown) before the proximal end of the stent during stent delivery. By deploying the distal end of the stent first and maintaining the axial position of the exposed distal end of the stent, the handle assembly 250 enables accurate and precise positioning of the distal end of the stent. This functionality can be useful for applications where accurate and precise placement of the distal end of the stent is clinically necessary. For example, then the aorta is accessed through the femoral artery (as is typical of EVAR procedures for AAA repair), this embodiment of handle assembly 250 can be used to deploy a stent graft in a known region of healthy aortic tissue that is superior to an aortic aneurysm but inferior to a renal artery. Precise superior positioning of the distal end of the stent is expected to increase (e.g., maximize) coverage of and sealing to healthy aortic neck tissue without blocking blood flow into the renal artery. In other embodiments, the handle assembly 250 may be used in various other applications that require or benefit from accurate placement of a distal end of the stent (with respect to the handle operator) 1.

Figure 6B:
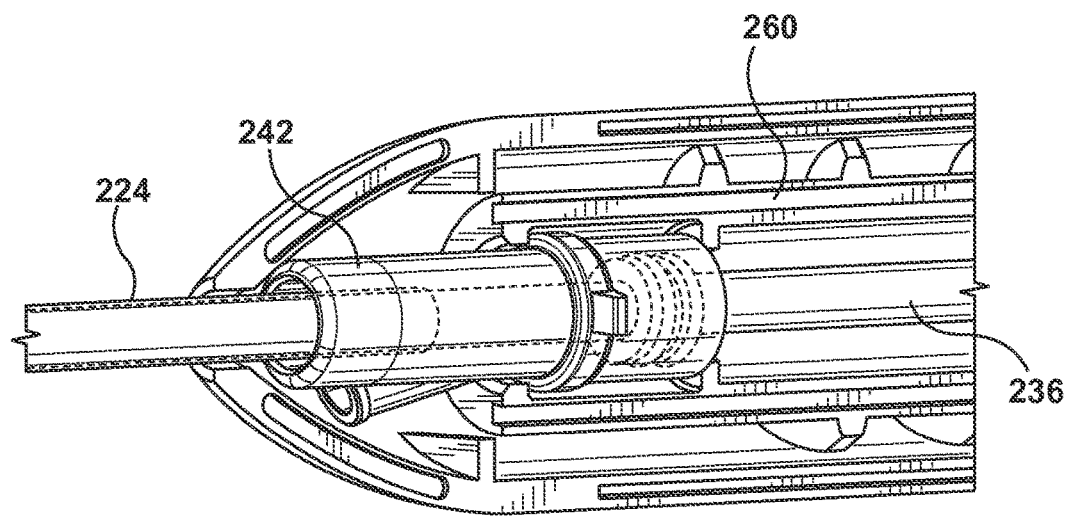
FIGS. 6B-6D are enlarged partial cut-away views of portions of the handle assembly of FIG. 6A.
Figure 6C:
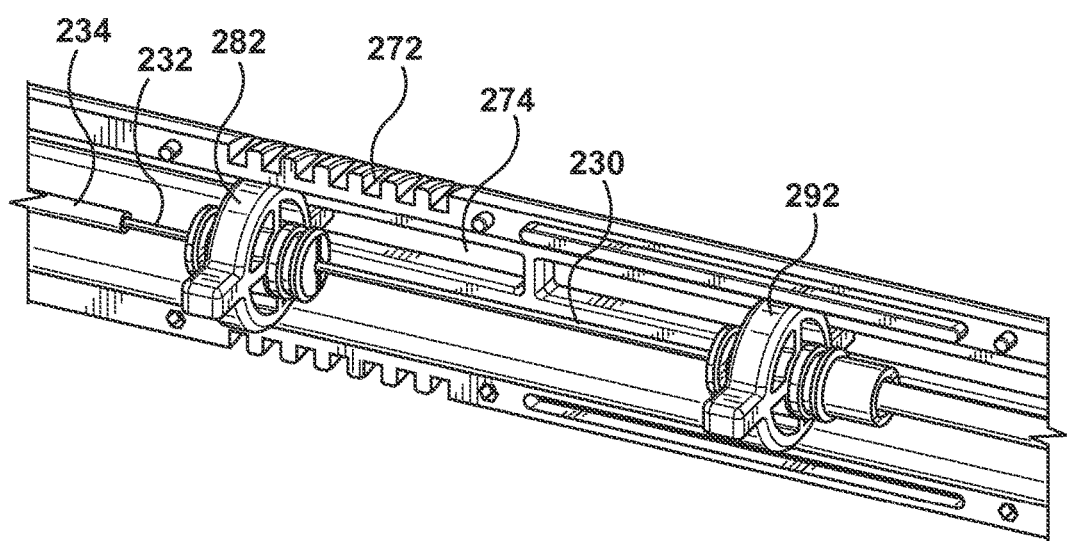

In the embodiment shown in FIGS. 6A-6E, the first lead screw 260 is directly or indirectly coupled to a tubular enclosure that can translate in a proximal direction to expose the stent. For example, as shown in FIGS. 6A and 6B, the first lead screw 260 can be coupled to outer sheath 224 of the delivery catheter such that translation of the first lead screw 260 actuates corresponding translation of the outer sheath 224. In certain embodiments, the first lead screw 260 can be coupled to a distal coupler 242, which is in turn coupled to the outer sheath 224 such that proximal and distal movement of the first lead screw 260 corresponds to proximal and distal movement of the outer sheath 224. For instance, sufficient proximal movement of the first lead screw 260 and distal coupler 242 will cause the outer sheath 224 to move proximally enough to expose the distal portion of the stent, thereby allowing the exposed portion of the stent to expand. Alternatively, the coupling between the first lead screw 260 and the outer sheath 224 can include any suitable mechanical communication between the first lead screw 260 and a tubular enclosure housing a stent. For example, the first lead screw 260 can be coupled directly to the tubular enclosure, coupled to a push or pull tube, a wire, and/or another suitable mechanism that is in turn coupled to the tubular enclosure. The first lead screw 260 can be coupled to the distal coupler 242 and/or other coupling epoxy, snap fit coupler designs, and/or any suitable mechanical fasteners. However, the coupling can additionally or alternatively include any suitable kind of coupling that effectuates movement of the tubular enclosure.

Figure 6D:
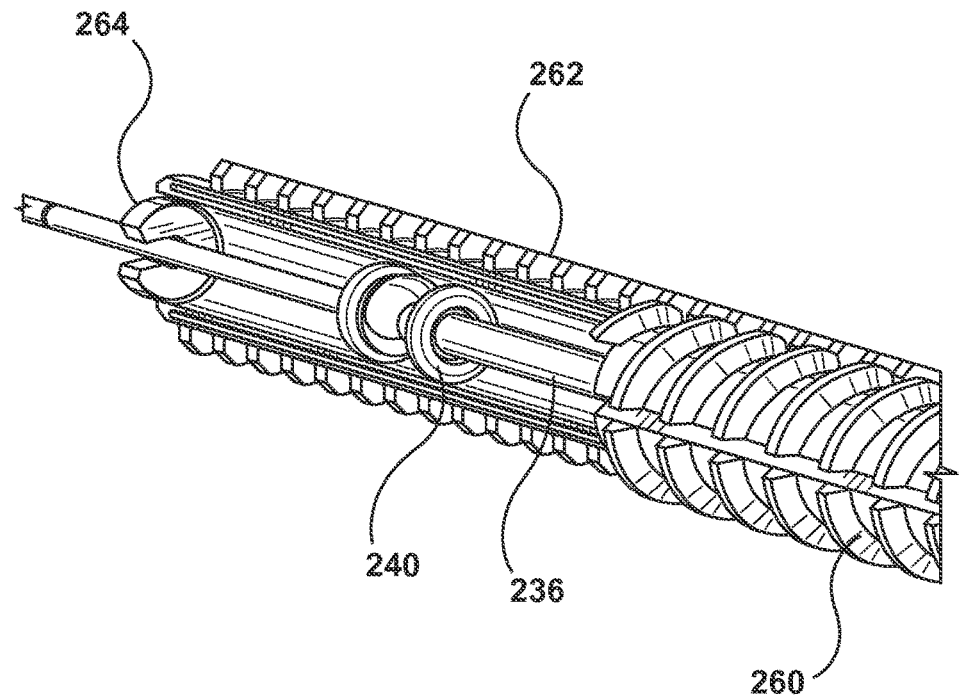

As shown in FIGS. 6A-6E, the second lead screw 262 can be directly or indirectly coupled to a proximal end of the stent (not shown) such that translation of the second lead screw 262 actuates corresponding translation of the proximal end of the stent. As shown in FIG. 6D, the second lead screw 262 is configurable to be mechanical communication with a proximal coupler 240 that is coupled to dilator 236, which is in turn coupled to the proximal end of the stent (e.g., as shown in FIG. 2C). For example, the second lead screw 262 can have a coupler engagement surface 264 in the same longitudinal path as the proximal coupler 240 such that when second lead screw 262 moves a sufficient distance in a distal direction, the coupler engagement surface 264 will abut the proximal coupler 240. After this engagement occurs, distal movement of the second lead screw 262 will cause corresponding distal advancement of the proximal coupler 240, the dilator 236, and the proximal end of the stent. Alternatively, the coupling between the second lead screw 262 and the proximal end of the stent (or other suitable stent portion) can include any suitable mechanical communication, such as those described above regarding the coupling between the first lead screw 260 and the outer sheath.

The handle assembly 250 can further include a stent compressor in mechanical communication with a first portion (e.g., a distal portion) of the stent and independently movable relative to a second portion of the stent such that movement of the stent compressor is independent of the lead screws 260, 262 and corresponds to axial compression and radial expansion of the stent. In the embodiment illustrated in FIG. 6E, for example, the stent compressor is defined by an axial compression slider 280 that is in mechanical communication with the distal end of the stent independent of the first and second lead screws 260 and 262. In other embodiments, the handle assembly 250 can include The axial compression slider 280 can be configured to axially compress the stent to facilitate positioning and longitudinal and rotational orientation. In particular, after the stent has been partially exposed and the exposed portion of the stent is able to radially expand, longitudinal proximal movement of the axial compression slider 280 can cause radial expansion and/or supplement self-expansion of the exposed portion of stent. In this manner, a practitioner can partially deploy the stent in a "jackhammer" type motion to compress the braided stent, reposition the stent as necessary to best interface with the vasculature (e.g., achieve opposition between the vessel wall and stent graft to form or confirm a seal) and/or other adjacent device components, and then fully deploy the stent by allowing the stent to self-expand (or supplementing radial expansion with the axial compression slider 280) without constraint by the outer sheath, top cap, and/or distal collet. Furthermore, the practitioner can make adjustments by manipulating the axial compression slider 280 in a stent tensioning direction, thereby radially compressing the stent again to allow for repositioning of the stent.

In one embodiment, the axial compression slider 280 is configured to expand the stent from a first radius when in its radially compressed configuration to a deployment radius that is sufficiently large to form an at least substantially fluid-tight seal against the vessel in which the stent is being deployed. For example, the axial compression slider 280 can be configured to expand from a smaller first radius to a larger deployment radius, where the deployment radius is between approximately three and five times the first radius (e.g., at least four times the first radius). However, in other embodiments the expansion ratio, or other relative change in cross-sectional stent dimension (e.g., diameter), can depend on the specific application.

Figure 6E:
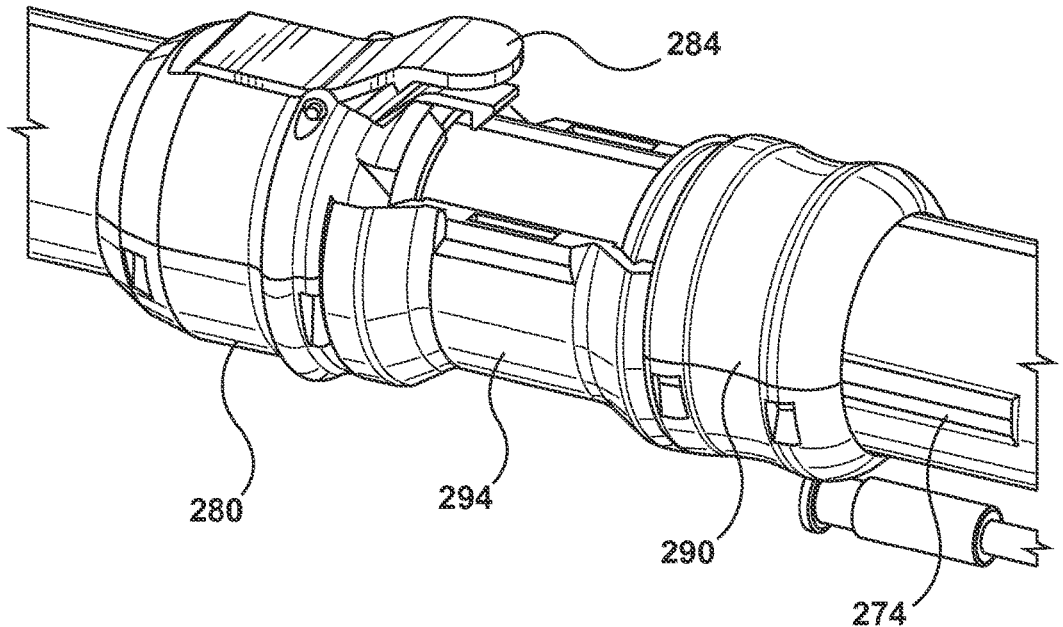
FIG. 6E is an isometric view of a portion of the handle assembly of FIG. 6A.

Referring to FIG. 6C, the axial compression slider 280 (FIG. 6E) can engage a distal bearing assembly 282, which is coupled to an inner shaft 232 by epoxy or any suitable fastening means. The inner shaft 232 can be in mechanical communication with the distal end of stent. Longitudinal movement of the compression slider 280 can correspond to longitudinal movement of the distal bearing assembly 282. The distal bearing assembly 282 can ride within one or more slots 274 on opposite sides of the handle housing 270 (FIG. 6A), and this longitudinal movement of the bearing assembly 282 can correspond to longitudinal movement of the distal end of the stent. In various embodiments, (e.g., when the proximal end of the stent is substantially stationary), proximal movement of the slider 280 will proximally pull the distal end of the stent so that the stent is in an axially compressed, radially expanded state. Similarly, distal movement of the slider 280 after some stent compression will distally extend the distal end of the stent so the stent is in a tensioned, radially constrained state, thereby allowing the practitioner to reposition the subsequently constrained stent relative to the vasculature. As shown in FIG. 6E, the axial compression slider 280 can include a locking tab 284 that selectively engages with one or more notches 272 (FIGS. 6A and 6C) and/or other types of locking portions on the handle of the housing 270. Engagement of the locking tab 284 with one of the notches 272 enables the operator to fix longitudinal position of the partially expanded/deployed stent in anticipation of full deployment. When the locking tab 284 is disengaged from the notches 272, such as by a depression of a lever or button by the device operator, the slider 280 is free to longitudinally move and axially compress the stent. When the locking tab 284 is engaged with one of the notches 272, the longitudinal position of the slider 280 is set. In various embodiments, the set of notches 272 can correspond to discrete degree of stent compression that the operator can use to gauge stent deployment. In other embodiments, the handle assembly 250 can include any suitable locking mechanism for securing the longitudinal position of slider 280.

Figure 8B:
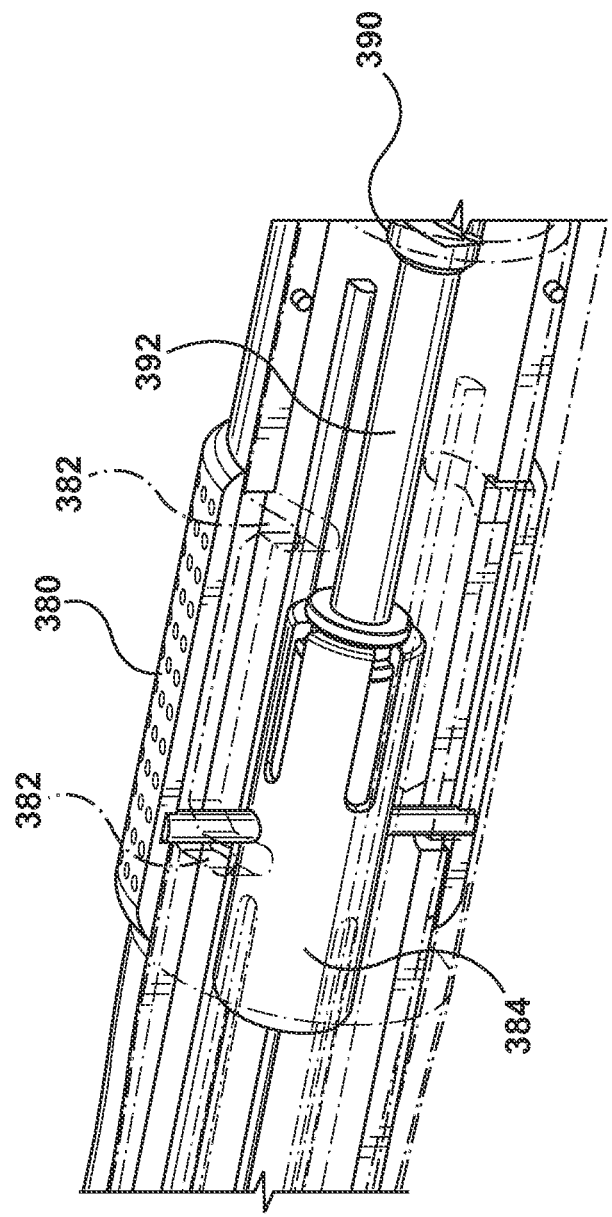
FIG. 8B is an enlarged, partially translucent isometric view of a portion of the handle assembly of FIG. 8A.
Figure 9:
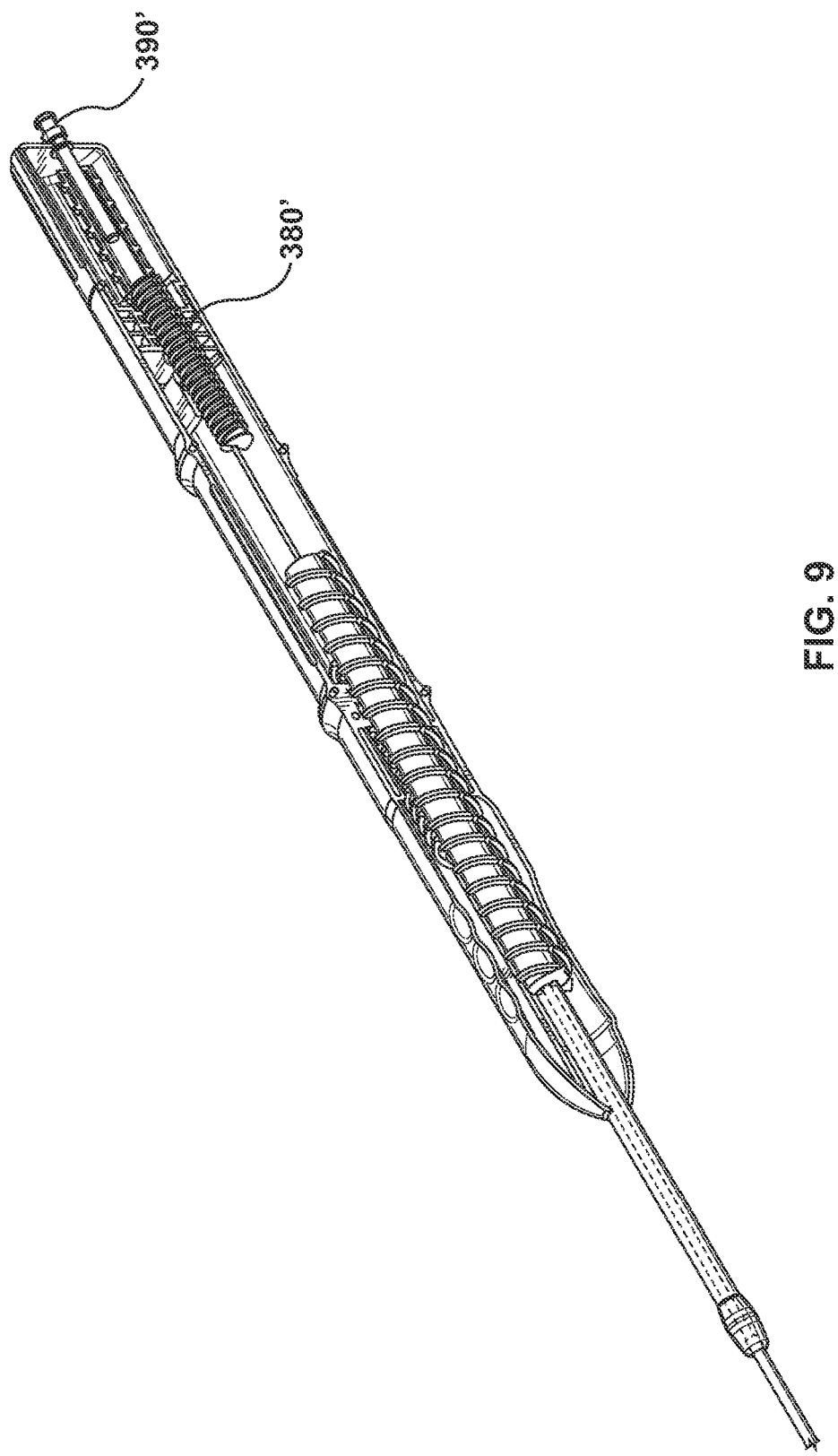
FIG. 9 is a partial cut-away isometric view of a handle assembly configured in accordance with another embodiment of the technology.

Other variations of the handle assembly 250 can include other mechanisms for facilitating axial stent compression independently of the first and second lead screws 260 and 262. For example, the embodiment of FIGS. 8A and 8B includes an axial compression slider 380 and/or other stent compressor that can be used to rotationally and longitudinally manipulate a compression coupler 384, which is coupled to the inner shaft by epoxy and/or any suitable fastening means. Similar to the slider 280 described above with reference to FIGS. 6A-6E, longitudinal translation of the slider 380 corresponds, through mechanical communication, to longitudinal movement of the distal end portion of a stent for selective and reversible axial compression of the stent. As shown in FIG. 8B, the longitudinal position of the slider 380 can be locked by rotating the slider 380 so that the coupler 384 engages one of the plurality of slider lock notches 382 in the handle housing. As another example, the embodiment of FIG. 9 includes a compression lead screw 380' coupled to the inner shaft by epoxy or any suitable fastening means. Rotation of the compression lead screw 380' will result in its longitudinal translation and corresponding longitudinal motion of the inner shaft and distal end portion of the stent for selective and reversible axial compression of the stent.

Referring back to FIGS. 6A-6E, the handle assembly 250 embodiment can further include a top cap slider 290 (FIG. 6E) that is configured to distally move the top cap 222. The top cap slider 290 can engage a proximal bearing assembly 292 (FIG. 6C), which is coupled to the tip tube 230 by epoxy or any suitable fastening means. Like the distal bearing assembly 282, the proximal bearing assembly 292 can ride along one or more slots 274 on opposite sides of the handle housing during its longitudinal movement. Because tip tube 230 is in mechanical communication with the top cap 222, longitudinal movement of the top cap slider 290 corresponds to longitudinal movement of the top cap 222. In particular, sufficient distal movement of the top cap slider 290 can completely expose a distal end portion of the stent. As shown in FIG. 6E, the top cap slider 290 can be selectively coupled to the axial compression slider 280 by means of a removable slider collar 294. When the slider collar 294 is coupled to both the compression slider 280 and the top cap slider 290 (e.g., with a snap fit or fasteners) the compression slider 280 and the top cap slider 290 can move in tandem. When the slider collar 294 is removed, the compression slider 280 and the top cap slider 290 are movable independent of one another. In some embodiments, the top cap slider 290 can also be locked directly to the compression slider 280 by a snap fit and/or other suitable fasteners (e.g., after the slider collar 294 is removed). An alternative embodiment of the top cap slider 290 is shown in FIGS. 10A and 10B, in which the top cap slider 290 is positioned on the proximal end portion of the housing and engages proximal bearing assembly 292 in a manner similar to that described above.

Other variations of the handle assembly 250 can include other mechanisms for moving a top cap. For example, the embodiment of FIGS. 8A and 8B includes a tip release screw 390. When turned, the tip release screw 390 can move distally and cause the top cap to move distally and release the distal end portion of the stent. The threads of the tip release screw 390 can prevent accidental deployment as the result of pushing axially on the head of the tip release screw 390. As another example, the embodiment of FIG. 9 includes a tip release pusher 390'. When pushed in a distal direction, the tip release pusher 390' moves distally and causes the top cap to move distally and release the distal end portion of the stent. In these and other embodiments, additional locks and/or other safety mechanisms (e.g., collars, mechanical fasteners, mechanical keys, etc.) can be removeably coupled to the mechanisms for moving the top cap to reduce the likelihood of accidental or premature deployment of the top cap.

FIGS. 11A-12D show another embodiment of the handle assembly 450 with the first and second lead screws 460 and 462. In this embodiment, the handle assembly 450 is configured to deploy, from a tubular enclosure 420 (FIG. 11A), a proximal end portion 410p of the stent 410 before the distal end portion 410d of the stent 410 during a "reverse deployment" stent delivery. By deploying the proximal end portion 410p of the stent 410 first and maintaining the axial position of the exposed proximal end of the stent 410, the handle assembly 450 can facilitate accurate and precise positioning of the proximal end portion 410p of the stent 410. This functionality can be useful for applications in which it is important to align the proximal end of the stent 410 correctly. For example, assuming an approach through the femoral artery typical of EVAR procedures for AAA repair, this embodiment can be used to deploy a stent graft in an iliac artery for overlapping and sealing with an implanted aortic stent as it may be desirable to ensure that (1) adequate stent length will be deployed in the iliac artery, and/or (2) no vessels branching from the iliac artery (e.g., the hypogastric artery) are inadvertently blocked. In other embodiments, the handle assembly 450 may be used in other applications that benefit from accurate and precise placement of a proximal end of the stent.

In the embodiment of the handle assembly 450 shown in FIGS. 11A-12D, the first lead screw 460 can be directly or indirectly coupled to a tubular enclosure that can travel in a distal direction to expose the stent. For example, the first lead screw 460 can be in mechanical communication with the top cap 424 of the delivery catheter such that distal translation of the first lead screw 460 actuates corresponding distal translation of the top cap 424. As shown in FIG. 12D, the first lead screw 460 can be coupled to a proximal coupler 440, which is in turn coupled to the tip tube 430, and the tip tube 430 is coupled to the top cap 424. In particular, sufficient distal movement of the first lead screw 460 and the proximal coupler 440 will cause the top cap 424 (and/or any outer sheath attached to and extending the top cap 424 along the stent) to move distally enough to expose the proximal end portion of the stent, and additional distal motion of the first lead screw 460 will eventually cause top cap 424 to release the entire length of the stent, thereby allowing the stent to self-expand. Alternatively, the coupling between the first lead screw 460 and the top cap 424 can include any other suitable mechanical communication between the first lead screw 460 and the top cap 424, such as the direct or indirect methods described above with respect to the embodiment of FIGS. 6A-6E. In further embodiments, the coupling can additionally or alternatively include any suitable kind of coupling that effectuates movement of the distal top cap 424.

In the embodiment of the handle assembly 450 shown in FIGS. 11A-12D, the second lead screw 462 is directly or indirectly coupled to a distal end portion 410d of the stent 410 such that translation of the second lead screw 462 actuates corresponding translation of the distal end portion 410d of the stent 410. The second lead screw 462 can be configured to be in mechanical communication with the distal coupler 442 (FIG. 12C), which is coupled to the inner shaft 432, and the inner shaft 432 is engaged with the distal end portion 410d of the stent 410 by the leading collet 428. More particularly, as shown in FIG. 12C, the second lead screw 462 has a coupler engagement surface 464 moving within a neck 444 of the distal coupler 442 such that when second lead screw 462 moves proximally enough across the neck 444, the coupler engagement surface 464 will abut and engage the distal coupler 442. After this engagement occurs, additional proximal movement of the second lead screw 462 will cause corresponding proximal advancement of the distal coupler 442, the inner shaft 432, and the distal end portion 410d of the stent 410. Alternatively, the coupling between the second lead screw 462 and the distal end portion 410d of the stent 410 (or any suitable stent portion) can include any suitable mechanical communication.

Figure 13:
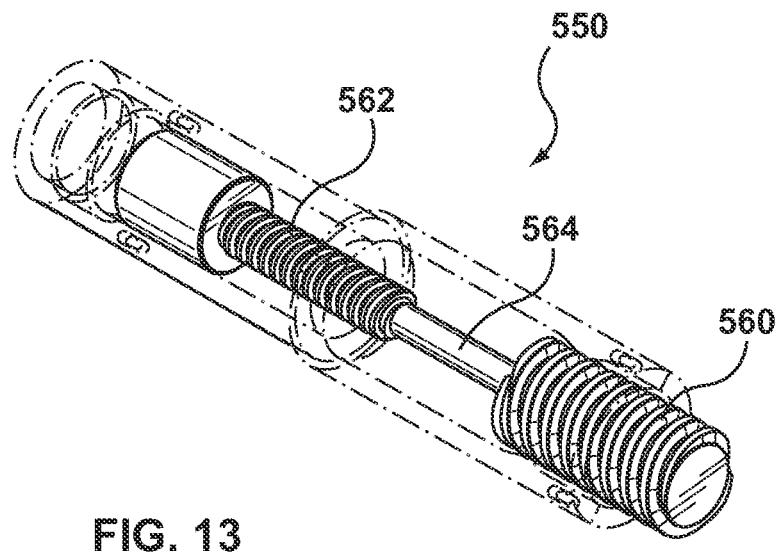
FIG. 13 is a partially translucent isometric view of a portion of a handle assembly configured in accordance with another embodiment of the technology.

FIG. 13 is a partially transparent, isometric view of a portion of a handle assembly 550 configured in accordance with another embodiment of the technology. The handle assembly 550 can include a first lead screw 560 having a first pitch and a second lead screw 562 having a second pitch different from the first pitch. Similar to the handle assemblies in the embodiments described above, one of the lead screws 560 or 562 is in mechanical communication with a tubular enclosure surrounding a stent, and the other lead screw 560 or 562 is in mechanical communication with either a proximal or distal end portion of the stent. The first and second lead screws 560 and 562 can be of opposite handedness and engaged with a shaft 564 such that a clockwise or counterclockwise rotation of the shaft 564 will cause the lead screws 560, 562 to axially translate in opposite directions. In some variations, second lead screw 562 can be internally threaded with a thread corresponding to the pitch and handedness of first lead screw 560, such that the first lead screw 560 can pass longitudinally within the second lead screw 562 as the lead screws 560, 562 axially translate.

Figure 14:
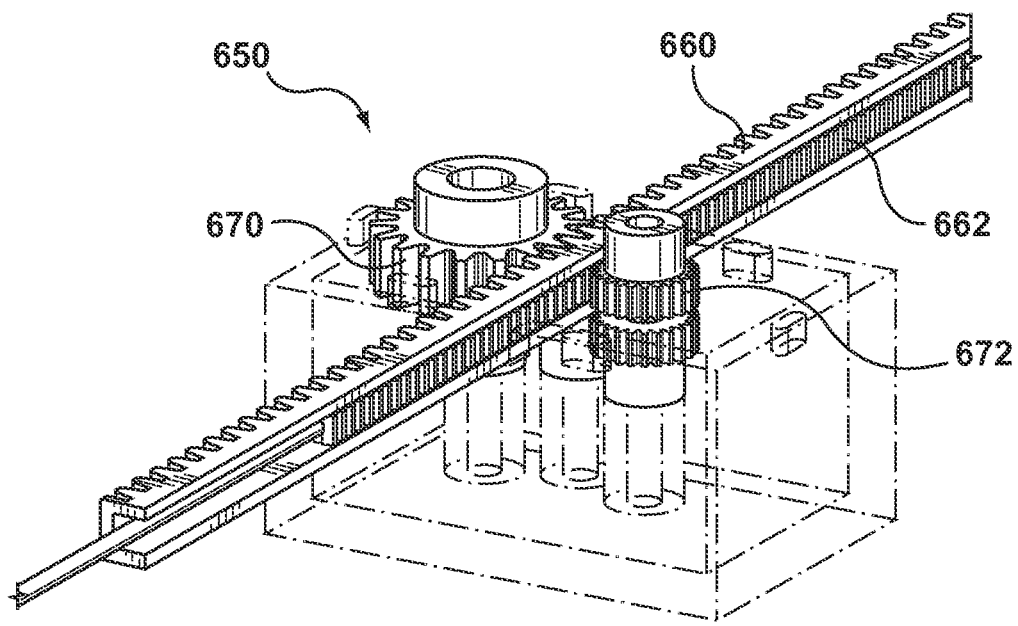
FIG. 14 is a partially translucent isometric view of a portion of a handle assembly configured in accordance with another embodiment of the technology.

FIG. 14 illustrates a handle assembly 650 configured in accordance with yet another embodiment of the technology. The handle assembly 650 can include a series of coaxial, nested first and second racks 660 and 662 that engage with respective first and second pinions 670 and 672 such that the movements of racks 660, 662 and pinions 670, 672 are interrelated by gearing. One of the racks 660 or 662 can be configured to be coupled to a tubular enclosure (e.g., a catheter or top cap), and the other rack 660 or 662 can be configured to be coupled to a stent (e.g., using similar attachment mechanisms as described above). Variations of the handle assembly 650 of FIG. 14 can include different actuation inputs that induce opposing movement of the racks 660 and 662. For example, rotation of either the first pinion 670 or the second pinion 672 by a handle component (not shown) will effectuate the simultaneous longitudinal translations of the first and second racks 660 and 662 in opposite directions. Alternatively, actuation of either the first rack 660 or the second rack 662 by a handle component (not shown) will be translated through the gearing to effectuate the simultaneous longitudinal translation of the other rack 660 or 662 in an opposite direction. The pitches of the racks 660, 662 and the pinions 670, 672 can vary to facilitate different absolute and relative rates of travel of the racks 660, 662 for each revolution of the pinions 670, 672. In still other embodiments, the handle assembly 650 can include suitable additional features, and/or have a different suitable gearing configuration.

Other Aspects of Handle Assemblies

In some embodiments, the handle assemblies described above can include a delay system that delays the synchronized actions of exposing a stent and axially compressing the stent until after a portion of the stent is exposed. In particular, in some variations, the delay system delays mechanical communication between a moving position compensating element and the stent until a predetermined portion of the stent is exposed from a tubular enclosure. In other variations, the delay system delays movement of the position compensating element until a predetermined portion of the stent is exposed from the tubular enclosure. The delay can be based on, for example, the distance that the tubular enclosure must travel before beginning to expose the stent. The delay system can accordingly avoid premature radial expansion of the stent within the tubular enclosure.

FIG. 6D illustrates one embodiment of a delay system in which there is a spatial longitudinal offset between the proximal coupler 240 and the coupler engagement surface 264 of the second lead screw 262. The longitudinal offset corresponds to a predetermined delay distance. Upon rotation of the shaft portion of the handle assembly, both the first and second lead screws 260 and 262 begin to move in opposite directions, but because of the longitudinal offset between the coupler engagement surface 264 of the second lead screw 262 and the proximal coupler 240, the coupler engagement surface 264 does not abut the proximal coupler 240 until the second lead screw 262 has traversed the offset. In other words, rotation of the handle actuates both lead screws 260, 262, but during an initial delay lasting until the coupler engagement surface 264 has traversed the predetermined delay distance, rotation of the handle can result in translation of first lead screw 260 to partially expose the stent without resulting in axial compression of the stent.

Figure 12C:
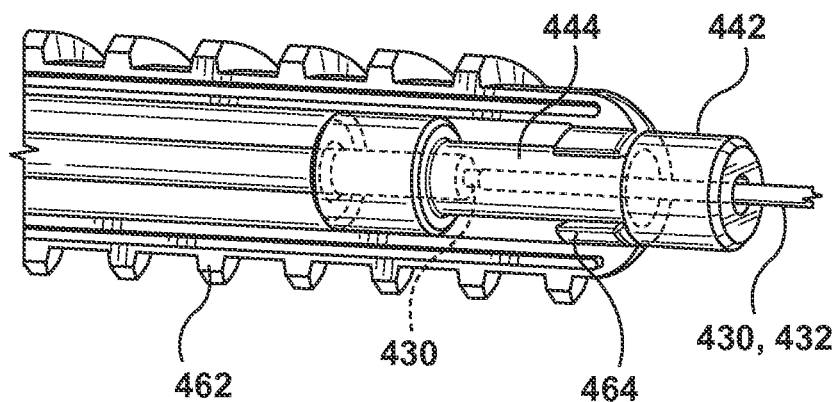
Figure 12D:
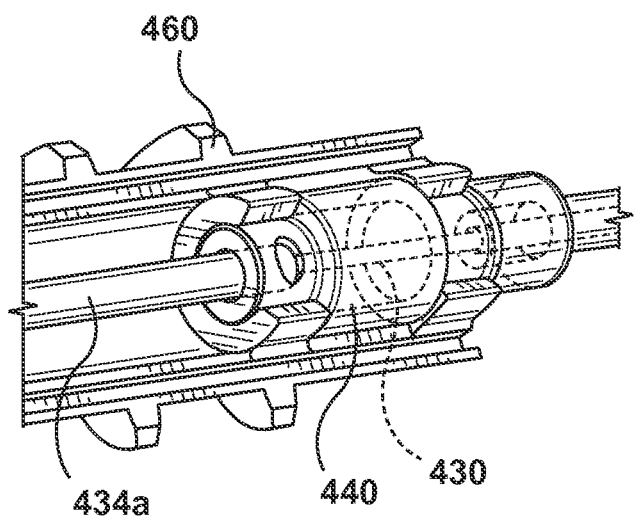

FIG. 12C illustrates another embodiment of a delay system in which the distal coupler 442 with the neck 444 is responsible for a delay in synchronization, where the length of the neck 444 is equal to a predetermined delay distance. Upon rotation of the shaft portion of the handle assembly 450, both the first and second lead screws 460 and 462 begin to move in opposite directions, but because of the neck 444 of distal coupler 442, the coupler engagement surface 464 of the second lead screw 462 does not abut the shoulder of the distal coupler 442 until the second lead screw 462 has traversed the neck 444. In other words, similar to the embodiment of FIG. 6D, rotation of portions of the handle assembly 450 actuates both lead screws 460, 462, but during an initial delay lasting until the coupler engagement surface 464 has traversed the predetermined delay distance across the coupler neck 444, rotation of the handle can result in translation of the first lead screw 460 to partially expose the stent, without resulting in axial compression of the stent.

In other embodiments of delay systems, the proximal or distal coupler can be in a reverse configuration with respect to the uncovering element and the position compensating element, and/or the delay system can include other components to facilitate a delay. Furthermore, in some embodiments, the handle assembly does not include a delay system to delay axial compression of the stent. In an auto-compression embodiment, the simultaneous actions of exposing the stent and axially compressing the stent can be carefully synchronized (e.g., with no delay of either action) with relative rates appropriate so that a suitable amount of axial compression is performed at the same time the stent is initially exposed.

In some embodiments, the housing can include a mechanism that operates additionally or alternatively to the axial compression slider 280 (FIG. 6E) and radially compresses the stent diameter after partial deployment. For example, as shown in FIGS. 10A and 10B, the handle assembly can include a repositioning ring 281 that, when moved longitudinally along the axis of the housing, can be used to reduce the outer profile of a stent that has been axially compressed to a radially expanded state (e.g., by simultaneous auto-compression as described above, or by an independent axially compressing component). The repositioning ring 281 can be in mechanical communication with an end portion of the stent by a push or pull tube such that proximal or distal movement of the repositioning ring 281 causes corresponding movement of an end of the stent, thereby extending and radially contracting the stent.

As another example, the stent can be undeployed by backdriving the shaft portion of the handle, rotating the shaft portion in a direction opposite the direction required for deployment, such as to reverse the paths of the lead screws. In this reverse deployment, the stent becomes elongated and radially compressed, and the sheath recovers the exposed portion of the stent. Once the stent returns to its radially compressed state, the device operator can reposition the stent relative to the surrounding environment.

Figure 15A:
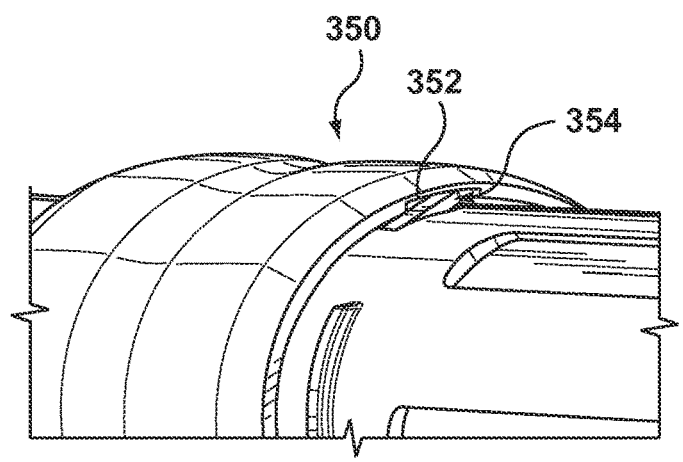
FIG. 15A is a partial isometric view of a portion of a handle assembly configured in accordance with an embodiment of the technology.

As shown in FIG. 15A, in some embodiments the housing further includes a rotational control mechanism 350 that limits rotation of the shaft portion to rotation in a deployment direction (i.e., the direction that actuates stent deployment). In preventing the rotation of the shaft portion in the direction opposite the deployment direction, the rotational control mechanism 350 can prevent axial compression of the stent when the stent is still radially constrained in the tubular enclosure, as well as selectively lock against reverse deployment while stent deployment is in progress. In some embodiments, the rotational control mechanism 350 can be selectively disengaged so as to selectively permit rotation in the direction opposite the deployment direction, such as to permit reverse deployment. When the rotational control mechanism 350 is disengaged, the shaft portion can be rotated in the direction opposite the deployment direction in order to reconstrain the stent within the tubular enclosure. By permitting reverse deployment, the handle assembly can allow repositioning of the entire stent even after the stent has been partially deployed, if so desired.

Figure 15B:
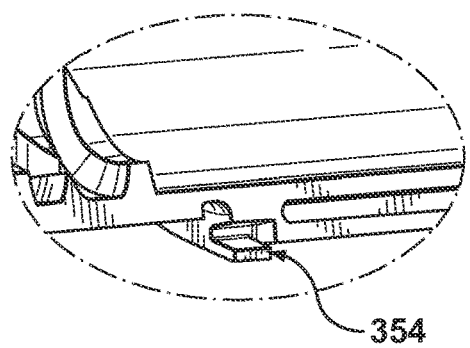
FIG. 15B is an enlarged view of a portion of the handle assembly of FIG. 15A.
Figure 15C:
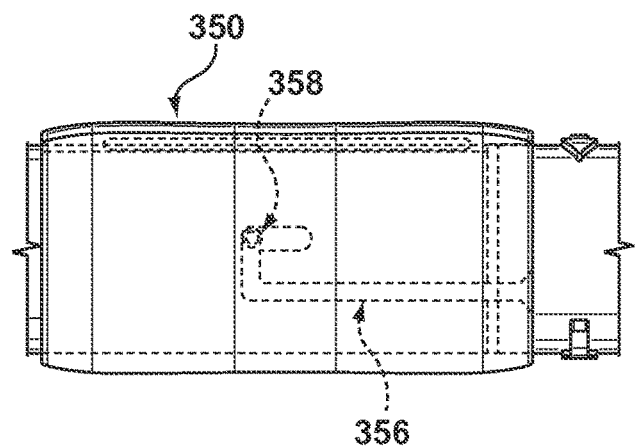
FIG. 15C is a partially translucent side view of a portion of the handle assembly of FIG. 15A.

As shown in FIGS. 15A-15C, a locking collar can define at least one channel 352 and the rotatable shaft portion can define at least one spring tab 354. As long as the rotational control mechanism 350 is engaged, the spring tab 354 flexes to accommodate rotation of the shaft portion in the deployment direction, but the spring tab 354 engages and stops against the channel 352 when the shaft portion is rotated in the direction opposite of the deployment direction. When the spring tab 354 stops against the channel 352, tactile and/or audio clicking feedback can inform the handle operator that he or she has rotated the shaft in an impermissible direction. The locking collar can include multiple channels 352 (e.g., four channels 352 equally circumferentially distributed around the collar), such that a single spring tab 354 on the shaft portion permits no more than ninety degrees of rotation in the non-deployment direction. However, in other embodiments the rotational control mechanism 350 can include any suitable number of channels 352 and/or spring tabs 354. Disengagement of the rotational control mechanism 350 can be performed, for example, by sliding the locking collar distally or proximally out of the rotational path of the spring tab 354. For example, as shown in FIG. 15C, moving the locking collar both rotationally and longitudinally to navigate a key 358 on the shaft portion through a guide path slot 356 in the locking collar will permit the locking collar to be oriented in a manner where the spring tab 354 will not engage with channel 352. Alternatively, the locking collar can be completely removed to disengage the rotational control mechanism 350. Furthermore, the housing can additionally or alternatively include other suitable features for selectively restraining rotation of the shaft portion to one direction.

In some embodiments, the housing additionally or alternatively includes other control mechanisms that selectively prevent rotation in a deployment direction. For example, the housing can include an additional or alternative rotational control mechanisms that prevent rotation of the shaft portion in the deployment direction until intentional steps are taken to disengage the rotational control mechanism, such as to prevent premature deployment of the stent (e.g., when the delivery catheter is not yet at the target area).

Figure 7:
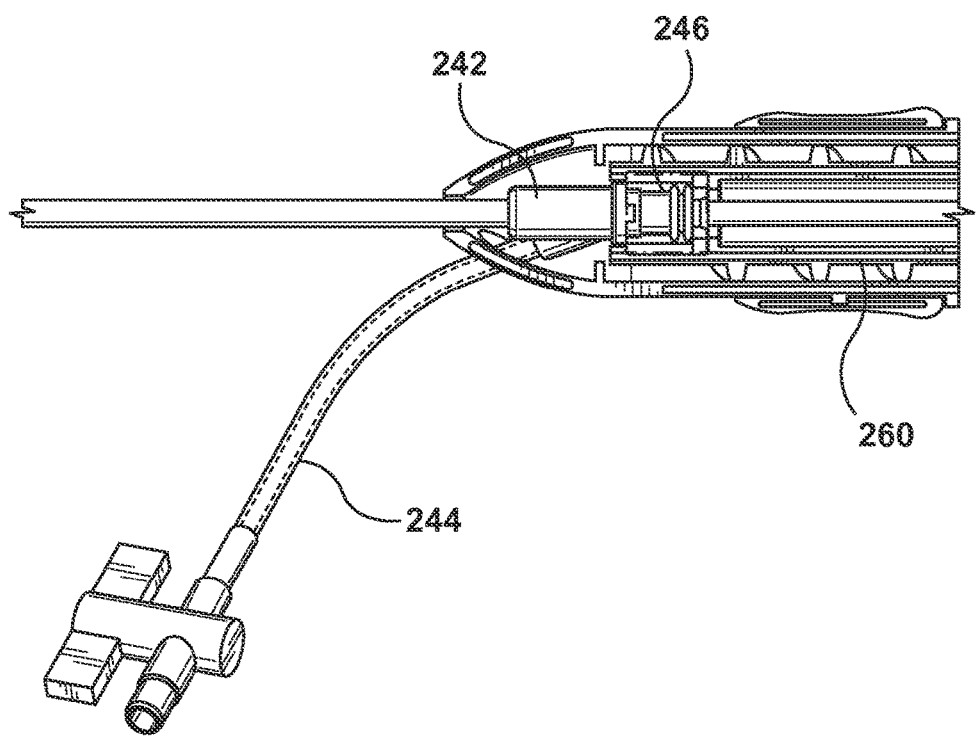
FIG. 7 is an enlarged partial cut-away view of a distal portion of the handle assembly configured in accordance with an embodiment of the technology.

In further embodiments, the handle assembly can include one or more points of entry for contrast fluid. For example, as shown in FIG. 7, the distal coupler 242 can be coupled to contrast tubing 244 to facilitate injection of contrast fluid through the delivery catheter to the stent region. The injected contrast fluid aids in imaging the target area surrounding the stent for purposes of advancing the delivery catheter and positioning and aligning the stent during deployment. The distal coupler 242 can include fluid-tight seal 246 that prevents contrast fluid and/or recirculating blood from entering the handle assembly. The fluid-tight seal 246 can include, for example, one or more o-rings. In other embodiments, the distal coupler 242 can additionally or alternatively include other suitable sealing features. Since in these embodiments the distal coupler 242 and sealing mechanism 246 may be in contact with recirculating blood, the distal coupler 242 and sealing mechanism 246 can be made of any suitable biocompatible material. In other examples, other proximal and/or distal couplers in handle assembly can be coupled to contrast tubing, and/or the handle assembly can include other fluid-tight couplers as appropriate. Furthermore, the couplers for introducing couplers can define a circular, annular space or other suitable non-circular shapes.

2. Selected Embodiments of Methods for Delivering Stent Grafts

In various embodiments, a method for implanting a stent graft at a target area for treatment of an aneurysm includes: advancing, toward the target area, a catheter comprising a tubular enclosure covering the stent graft; positioning the stent graft proximate to the target area; deploying the stent graft; allowing the stent graft to anchor in or at the target area; and withdrawing the catheter from the target area. Deploying the stent graft can include effectuating simultaneous, opposing translations of first and second handle components such that the first the handle component longitudinally displaces the tubular enclosure in a first direction, and the second handle component axially compresses the stent graft in a second direction opposite the first direction. The method is described further with reference to particular handle assemblies shown in FIGS. 16A-18E, but the method is not limited to use of the handle assemblies described herein. Furthermore, though the method is primarily described in regards to deploying a specific design of stent graft, it should be understood that the method can similarly be used to deploy other kinds of stent grafts or endografts, a bare stent, or any suitable kind of stent.

Various aspects of advancing the catheter, positioning the stent graft, allowing the stent graft to anchor in the target area, and withdrawing the catheter can be similar to those steps described in U.S. Patent Application Publication No. 2011/0130824, which is incorporated herein by reference in its entirety. For example, advancing the catheter can involve entry into a blood vessel using a percutaneous technique such as the well-known Seldinger technique.

With respect to deploying the stent graft, in one embodiment of the method, a practitioner or device operator can displace the tubular enclosure in a proximal direction to expose only a portion of the stent graft, constrain a distal endpoint of the stent graft in a radially compressed state, and axially compress the stent graft to radially expand only the exposed portion of the stent graft. For example, the device operator can initially rotate a shaft portion of handle to move the outer sheath 724 and expose a portion of the stent graft 710 (e.g., 2-3 inches). A delay system can stall any stent graft compression resulting from this initial rotation, though in other embodiments some amount of stent graft compression can automatically occur during this initial rotation. The top cap 722 can still constrain the distal end of the stent graft after this initial handle rotation. Proximal movement of an axial compression slider, which is coupled to the distal end of the stent graft 710d by leading collet 728, pulls leading collet 728 and distal stent graft end 710d proximally, which axially compresses and radially expands the exposed portion of the stent graft, as shown in FIG. 16A. During this time, the practitioner can view, through imaging methods and/or use contrast fluids and radiopaque markers, the rotational and longitudinal orientation of the exposed stent graft.

If not satisfied with the position and alignment of the stent graft, the device operator can radially collapse the stent graft down to an outer profile small enough for stent graft repositioning. In particular, distal movement of the axial compression slider pushes leading collet 728 and distal stent graft end 710d distally, which tensions and radially collapses the exposed portion of the stent graft to a degree suitable for repositioning. The repositioning process can repeat until the practitioner is satisfied. In some embodiments, the method can additionally or alternatively include resheathing the exposed stent graft with the tubular enclosure. For example, the device operator can rotate (backdrive) the shaft portion of the handle in the direction opposite that for actuating deployment, in order to reposition the sheath over the previously exposed portion of the stent graft.

When satisfied with the position and alignment of the stent graft, the device operator can release the distal end of the stent graft from its radially compressed state. For example, the device operator can move a tip slider in a distal direction to remove the top cap 722 from the stent graft, thereby releasing the distal end of the stent graft, as shown in FIG. 16B. However, the method can involve other actuation means, such as rotating a tip screw, to remove the top cap or other appropriate enclosure.

Once the distal end of the stent graft is released, the device operator can simultaneously further expose the stent graft by displacing the tubular enclosure and axially compress the stent graft by advancing the unexposed proximal end of the stent graft as the tubular enclosure is displaced, thereby compensating for stent graft foreshortening. For example, shown in FIG. 16B, the device operator can manipulate the handle to induce opposing translations of first and second handle components, where one handle component longitudinally displaces the tubular enclosure (e.g., outer sheath 224) in a proximal direction while the other handle component axially compresses the stent graft with a distally-directed force (advancing a proximal end of the stent graft 710d via trailing collet 226).

With respect to deploying the stent graft, in another embodiment of the method shown in FIG. 17, in a reverse deployment scenario, the device operator manipulates the handle to induce opposing translations of first and second handle components, where one handle component longitudinally displaces the tubular enclosure (e.g., top cap 824 via tip tube 830) in a distal direction while the other handle component axially compresses the stent graft 810 with a proximally-directed force (e.g., retracting a distal end of the stent graft 810d via leading collet 828 and inner shaft 832).

FIGS. 18A-18E show an exemplary embodiment of the method used specifically to deliver stent graft grafts for treatment of an abdominal aortic aneurysm. In this specific application of the method, the method deploys stent grafts with D-shaped cross-sections as described in U.S. Patent Application Publication No. 2011/0130824, where the flat portions of the D-shaped stent grafts press against each other to form a straight septum and the curved portions of the D-shaped stent grafts press against the aortic wall to form a seal against the aortic wall. The figures show and are described with reference to the delivery device embodiment of FIG. 6A, but it should be understood that any suitable embodiments and variations of the device can similarly be used in the method. Furthermore, FIGS. 18A-18E show and are generally described with respect to the operations of handle of only one delivery device, which is typically identical to the delivery device used for deploying the depicted contralateral stent graft.

Figure 18A:
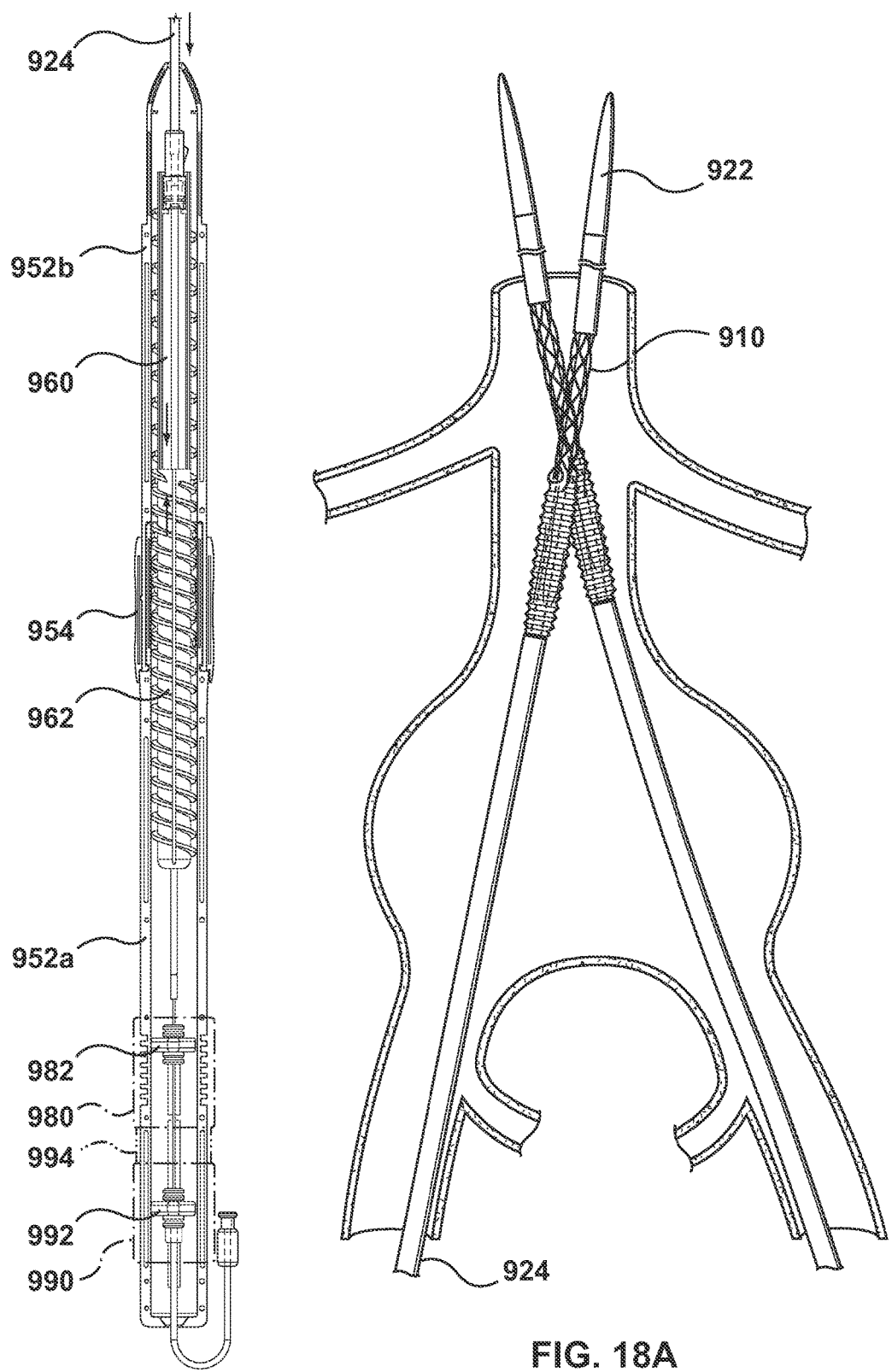

In FIG. 18A, stent grafts 910 are positioned superior to the aneurysm and partially unsheathed. The catheters of two instances of the delivery system have been advanced toward the target area in an aorta using various techniques, such as over-the-wire (guidewires not shown), with a first catheter advanced along the left iliac artery, and a second catheter advanced along the right iliac artery. The catheters have been advanced until the top caps 922 and stent grafts 910 are positioned superior to the aneurysm, where radiopaque markers can aid correct placement of the stent grafts. In one embodiment, the catheters cross paths within the aneurysm such that the distal end of each catheter approach and/or touch the side of the aortic wall that is opposite the side of entry. In other words, the crossing of catheters may induce a stent graft 910 passing through the aneurysm from the left iliac artery to appose the right side of the aortic wall, and a stent graft 910 entering from the right iliac artery to appose the left side of the aortic wall. On each delivery device, rotation of handle portion 952a has caused internal threads of handle portion 952a to simultaneously engage first and second lead screws 960 and 962, resulting in proximal translation of first lead screw 960 and distal translation of second lead screw 962. Proximal movement of first lead screw 960 has caused outer sheath 924 to retract and expose a portion of stent graft 910, though top cap 922 still constrains the distal end of stent graft 910. Meanwhile, in a delay system (not shown) as described above with respect to FIG. 6D, distally-travelling lead screw 962 has not traversed the predetermined delay distance, such that lead screw 962 does not yet axially compress the exposed stent graft 910.

Figure 18B:
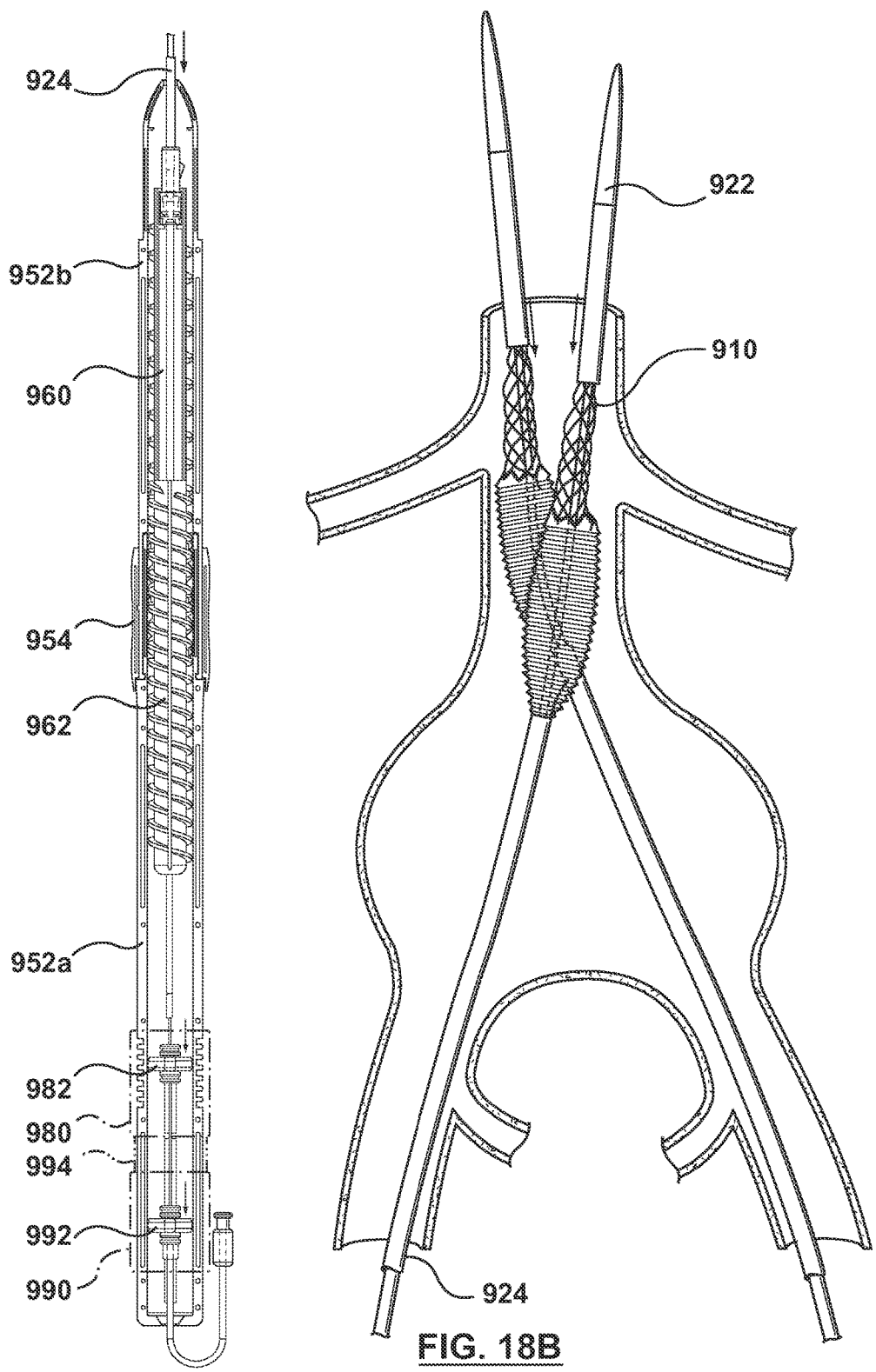

In FIG. 18B, the stent grafts 910 are slightly axially compressed such that the exposed portions of stent grafts 910 are slightly radially expanded. In particular, on each delivery device, the axial compression slider (represented by box 980), which is coupled to distal bearing assembly 982 in mechanical communication with the distal end of stent graft 910, has been pulled proximally to axially compress the exposed portion of stent graft 910. As described above, such axial compression induces and/or supplements the radial self-expansion of the stent graft 910. Since in each device, tip slider (represented by box 990) is coupled to axial compression slider 980 by removable slider collar 994, top cap 922 moves in tandem with the distal end of the stent graft 910. Additionally, axial compression slider 980 can optionally be moved distally to tension and radially collapse the exposed portion of the stent graft 910.

In other words, the longitudinal position of the axial compression slider 980 corresponds to the degree of radial expansion, so the device operator can move the axial compression slider 980 both proximally and distally to adjust the radial expansion and radial contraction, respectively, of the stent graft 910. Furthermore, the device operator can adjust the longitudinal position of the catheter as a whole by withdrawing and/or advancing the entire catheter, to adjust the longitudinal position of the stent grafts 910. Partial radial expansion of the stent grafts, when viewed under fluoroscopy by the device operator, aids optimal rotational and/or longitudinal positioning of the stent grafts 910, both relative to each other and relative to the aortic wall.

In particular, each partially deployed stent graft 910 is longitudinally positioned such that its graft material is aligned with (just inferior to) a renal artery in order to maximize overlap between the anchoring bare stent portion of stent graft 910 and healthy aortic neck tissue, without resulting in the graft material blocking blood flow to the renal arteries. Additionally, as shown in FIG. 18C, in instances in which the stent grafts 910 are being deployed in a patient having longitudinally offset renal arteries, the stent grafts 910 are optimally positioned with a corresponding longitudinal offset in order to accommodate the offset renal arteries without sacrificing coverage nor blocking blood flow to the renal arteries.

Furthermore, each partially deployed stent graft 910 is rotationally oriented such that the flat portions of the D-shaped stent grafts 910 press against each other to form a straight septum and the curved portions of the D-shaped stent grafts 910 press against the aortic wall to form a seal against the aortic wall.

Figure 18C:
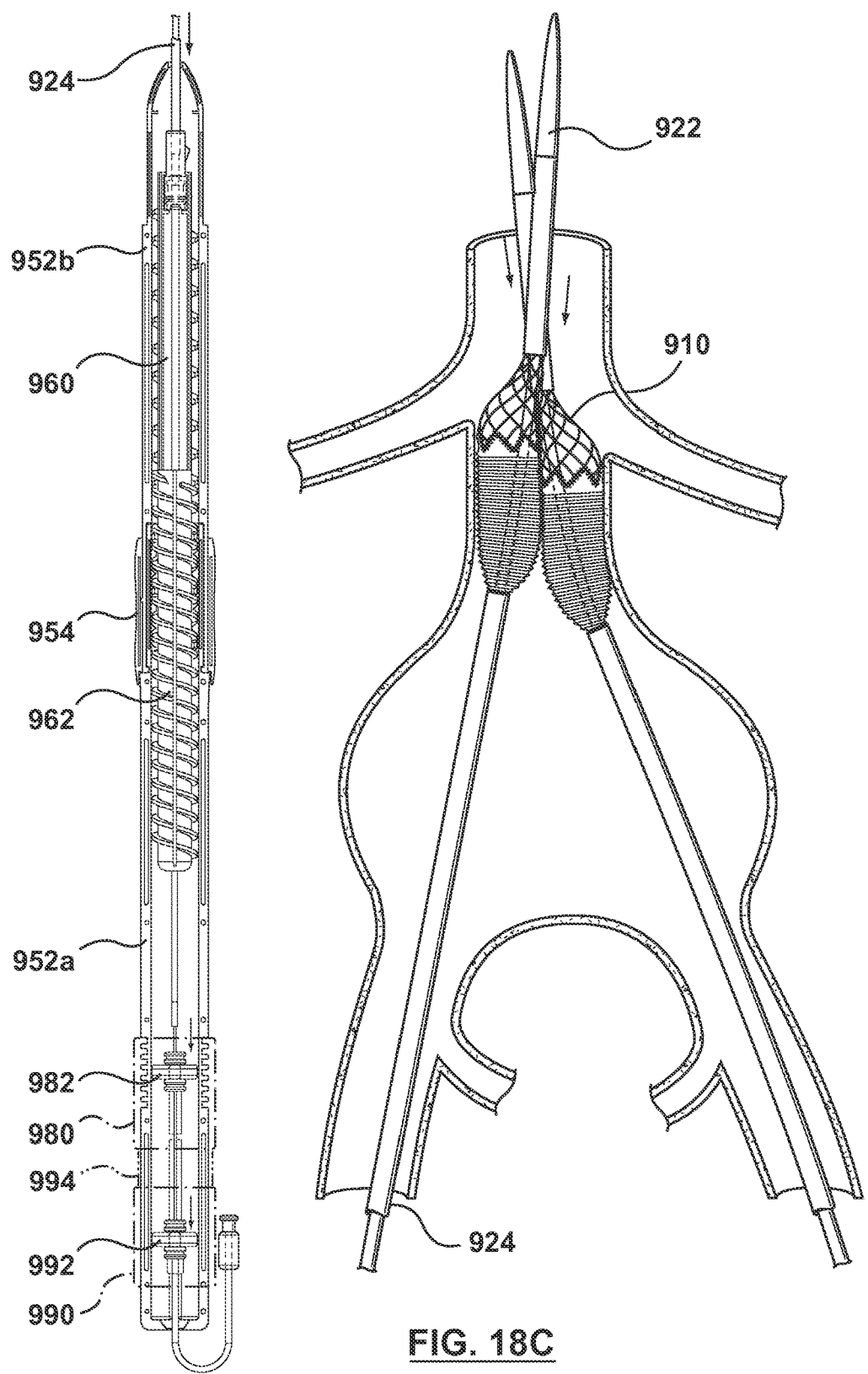

In FIG. 18C, the stent grafts are longitudinally and rotationally oriented in the desired manner, and further proximal retraction of axial compression slider 980 has induced additional radial expansion of the stent graft 910 to cause stent graft 910 to press against the aortic wall. The two stent grafts 910 in conjunction can be radially expanded to a have a deployment radius sufficiently large to form a complete seal between them, as well as with the aorta wall superior to the aneurysm. This seal can be verified or confirmed by introducing contrast fluid through the catheter (e.g., through contrast tubing in the handles) and viewing whether the expanded stent grafts 910 prevent contrast flow across the sealed region. Alternatively, other methods of contrast introduction can be performed to confirm the seal of stent grafts 910 against each other and/or against the vessel wall. As described above with respect to FIGS. 6C and 6E, axial compression slider 980 locks longitudinally in place with notches on the housing, in anticipation of full deployment of the stent grafts.

In FIG. 18D, the distal ends of stent grafts 910 are freed from top cap 922 and allowed to self-expand against each other and against the aortic wall. If the stent grafts 910 have barbs or other suitable anchoring mechanisms, the stent grafts have become anchored at their deployed position. On each delivery device, slider collar 994 has been removed to allow tip slider 990 to move independently of axial compression slider 980. The tip slider 990 has been moved distally to cause top cap 922 to move correspondingly move distally and release the distal end of the stent graft. After the distal end of the stent graft 910 self-expands, slider 990 may couple directly to axial slider 980. At this point during deployment, the device operator may choose to inject contrast fluid through one or both catheters, with contrast couplers described above, in order to verify quality of the seal formed between the stent grafts and with the aortic wall.

Following verification of position and seal, resumed rotation of the handle portion in each delivery device again effectuates the opposing longitudinal translations of the first and second lead screws 960 and 962. In particular, after the second lead screw 962 traverses the predetermined delay distance, the first lead screw 960 continues to proximally retract outer sheath 924 and the second lead screw 962 distally advances the proximal end of stent graft 910.

Figure 18E:
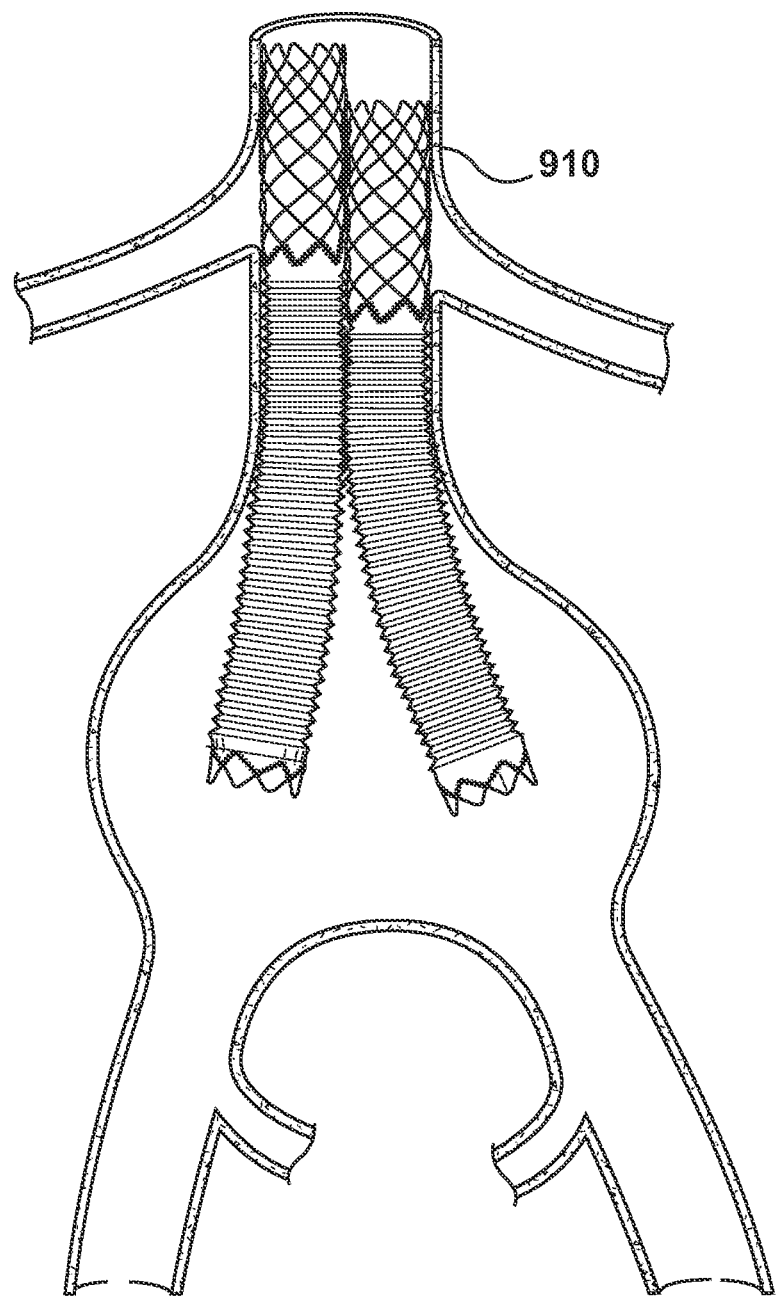

In FIG. 18E, the catheters have been withdrawn from the stent grafts 910 following full deployment of the stent grafts. The two simultaneous actions of the lead screws 960 and 962 during deployment have compensated for the displacement effects of stent graft foreshortening that would otherwise occur, thereby ensuring that the distal ends of stent grafts 910 maintain their respective positions during deployment. The stent grafts of FIG. 18E are shown with inferior ends terminating within the aneurysm. However, in other embodiments, each stent graft can extend into and anchor with a respective iliac artery. For example, the inferior graft end of the stent grafts 910 can terminate in the common iliac arteries immediately superior to the internal iliac arteries so as not to block blood flow to the internal iliac arteries. However, the stent grafts 910 can be positioned in any suitable manner.

Figure 19A:
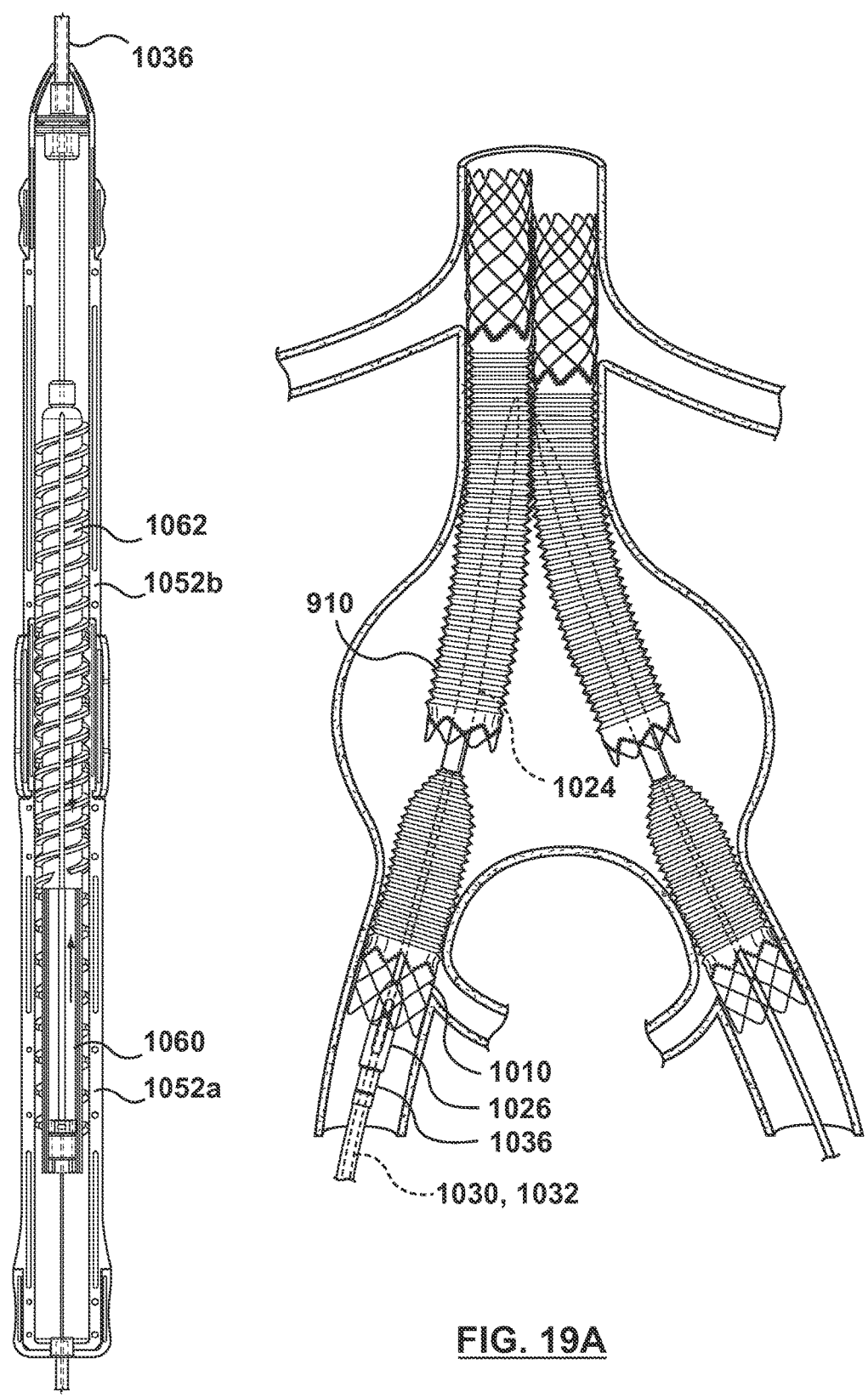
FIGS. 19A-19C illustrate a stent delivery method in accordance with another embodiment of the technology.
Figure 19B:
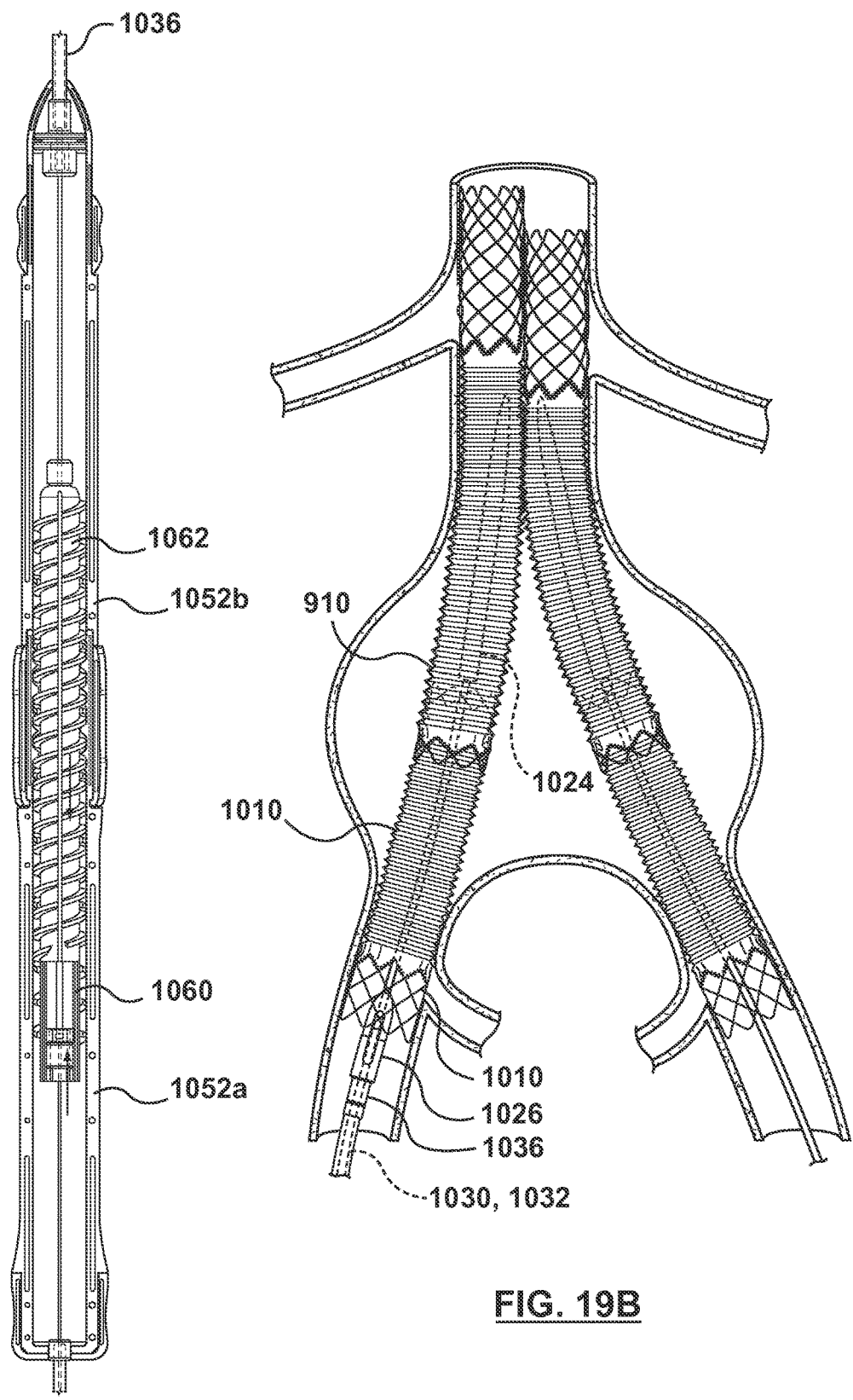
Figure 19C:
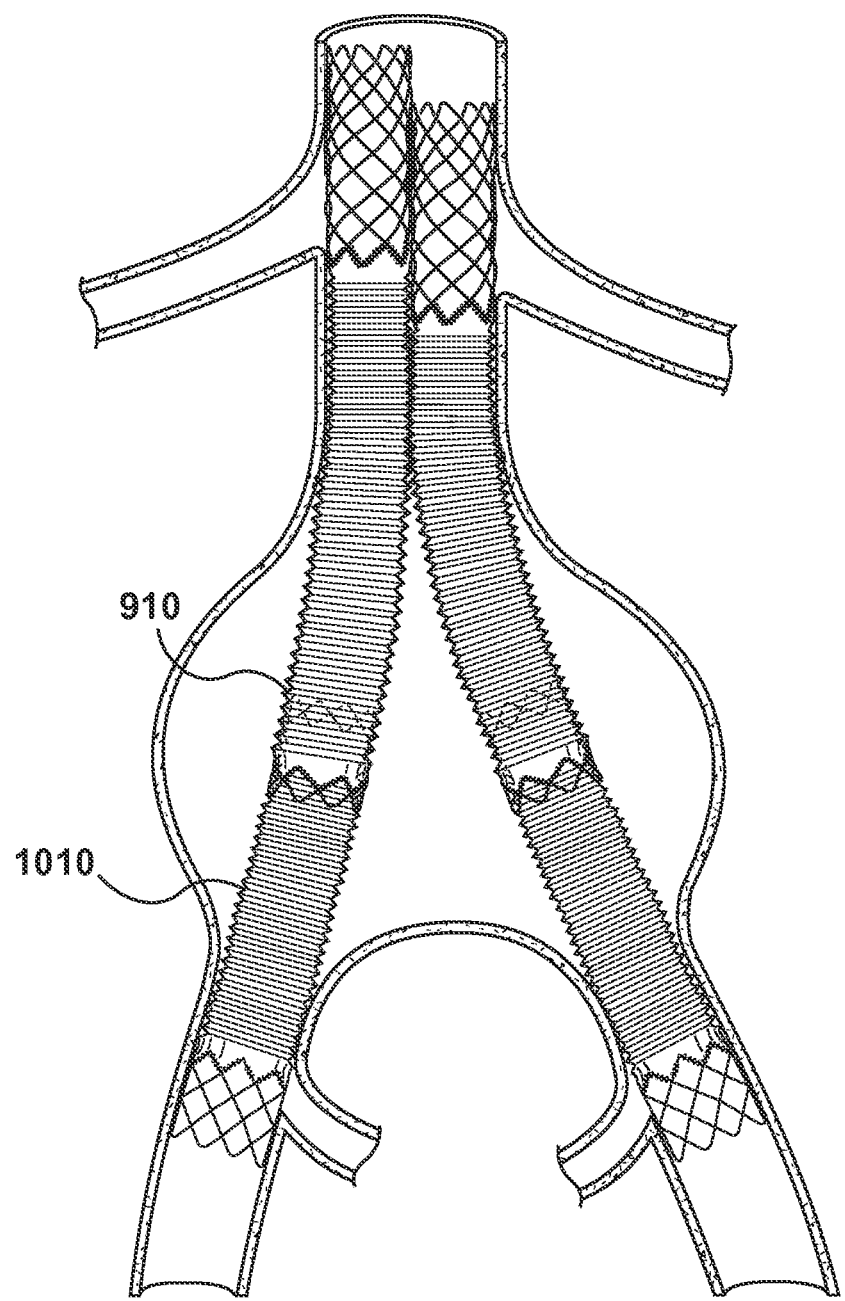

FIGS. 19A-19C show another exemplary embodiment of the method, extending that described with respect to 18A-18E. This specific application of the method deploys iliac stent grafts 1010, each of which couples to and extends a respective stent graft 910 deployed as described above. The figures show and are described with reference to the delivery device embodiment of FIG. 12A, but it should be understood that any suitable embodiments and variations of the device can similarly be used in the method. Furthermore, FIGS. 19A-19C depict the operations of handle of only one delivery device, which is typically identical to the delivery device used for deploying the depicted contralateral stent graft.

In FIG. 19A, stent grafts 1010 are partially deployed adjacent to previously deployed stent grafts 910. The catheter of each delivery device was advanced over guidewires toward the aneurysm and into the lumen of a corresponding stent graft 910. The proximal graft end of each stent graft 1010 was optimally aligned to be immediately superior to the internal iliac arteries, so as not to block the internal iliac arteries. However, the stent grafts 1010 can be positioned in any suitable manner. On each delivery device, rotation of handle portion 1052a relative to handle portion 1052b has caused internal threads of handle portion 1052a to simultaneously engage first and second lead screws 1060 and 1062, resulting in distal translation of first lead screw 1060 and proximal translation of second lead screw 1062. Distal movement of first lead screw 1060, which is in mechanical communication through tip tube 1030 to top cap 1024, has caused top cap 1024 to advance distally and expose a portion of stent graft 1010. The stent graft exposure began at the proximal end of the stent graft, which radially expanded off of docking tip 1026. Through a delay system (not shown) as described above with respect to FIG. 12C, proximally-travelling lead screw 1062 travels a predetermined delay distance before it becomes in mechanical communication with the distal end of stent graft 1010 through inner shaft 1032. Once the lead screw 1062 has traversed the predetermined delay distance, its proximal translation axially compresses the stent graft 1010 by proximally retracting the distal end of the stent graft 1010.

In FIG. 19B, the top caps 1024, and/or associated outer sheath if present, have advanced distally enough to release the distal ends of the stent grafts 1010, thereby freeing the distal end of the stent graft 1010. The superior ends of stent grafts 1010 are expanded within in the inferior ends of stent grafts 910, such as to extend the lumens of stent grafts 910 at a joining within the aneurysm. In other embodiments, the stent grafts 1010 can couple to the stent grafts 910 in any suitable location. At this point of deployment, the device operator may choose to inject contrast fluid through one or both catheters, using contrast couplers as described above, in order to verify quality of seal formed between stent grafts 910 and 1010, and/or with the iliac arterial wall.

In FIG. 19C, the catheters have been withdrawn from the stent grafts 1010 following full deployment of the stent grafts. The two simultaneous actions of the lead screws 1060 and 1062 during deployment of compensated for the displacement effects of stent graft foreshortening that would otherwise occur, thereby ensuring that the proximal ends of stent grafts 910 maintain their respective positions during deployment.

The handle assemblies and stent delivery methods shown and described herein offer several advantages over previous devices and stent delivery methods. For example, the handle assemblies provide for straightforward delivery of a stent graft to an artery while maintaining initial stent graft marker positions relative to a destination arterial wall. Embodiments employing opposing screws provide a user with the ability to deliver a stent graft at a high force with relatively little mechanical effort. This allows a user to exercise improved control over the delivery process, such as by enabling the user to control the outer diameter and/or length of the deployed stent. Further, the mechanisms disclosed herein provide effective push/pull motion while minimizing the number of parts, assembly time, and cost. The push/pull components move at relative rates according to the predetermined payout ratio (which, in the lead screw embodiment described above, is dependent on the difference in pitch between the lead screws), and determine the rate of stent deployment and degree of stent radial expansion. Such control over the rate of stent deployment and degree of stent radial expansion can allow the handle assemblies to maintain a low profile and minimize the overall bulk of the delivery device.

From the foregoing, it will be appreciated that specific embodiments of the technology have been described herein for purposes of illustration, but that various modifications may be made without deviating from the disclosure. Certain aspects of the new technology described in the context of particular embodiments may be combined or eliminated in other embodiments. Additionally, while advantages associated with certain embodiments of the new technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A stent delivery system for deploying a stent within a vessel, comprising:
    a delivery catheter comprising a tubular enclosure at a distal end portion of the catheter;
    a braided stent constrained within the tubular enclosure, wherein the stent is configured to transition between an elongated radially compressed state and a shortened radially expanded state;
    a handle assembly comprising:
    a first lead screw and a second lead screw of opposite handedness and positioned along a longitudinal axis, wherein the first lead screw is in mechanical communication with the tubular enclosure and the second lead screw is configured to be placed in mechanical communication with the stent;
    a housing coupled to the delivery catheter and having a bore wall surrounding at least a portion of each of the first and second lead screws, wherein the bore wall has a first housing thread and a second housing thread thereon, the first and second housing threads intersecting on the bore wall,
    wherein upon rotation of at least a portion of the housing about the longitudinal axis, the first housing thread engages the first lead screw and the second housing thread engages the second lead screw so as to induce at least substantially simultaneous translations of the first and second lead screws in opposite directions along the longitudinal axis, wherein the translations are configured to deploy the stent from the tubular enclosure.

2. The stent delivery system of claim 1 wherein the translations of the first and second lead screws at least substantially simultaneously expose the stent from the tubular enclosure and axially compress the stent.

3. The stent delivery system of claim 1 wherein the handle assembly further comprises a stent compressor in mechanical communication with a first end portion of the stent and independently movable relative to a second end portion of the stent such that movement of the stent compressor is independent of the first and second lead screws and corresponds to axial compression and radial expansion of the stent.

4. The stent delivery system of claim 3 wherein the stent compressor is in mechanical communication with a distal end portion of the stent such that movement of the stent compressor along the longitudinal axis corresponds to translation of the distal end portion of the stent independent of a proximal end portion of the stent.

5. The stent delivery system of claim 4 wherein the distal end portion of the catheter comprises a trailing collet coupled to the proximal end portion of the stent and a leading collet coupled to the distal end portion of the stent, wherein the second lead screw is configured to be placed in mechanical communication with the trailing collet and the stent compressor is in mechanical communication with the leading collet.

6. The stent delivery system of claim 4 wherein the stent compressor is configured to reversibly radially expand the stent to a deployment radius sufficient to form a seal against the vessel.

7. The stent delivery system of claim 4 wherein the stent compressor is configured to reversibly radially expand the stent from a first radius in the elongated radially compressed state to a deployment radius of about 3-5 times the first radius.

8. The stent delivery system of claim 3 wherein the stent compressor is configured to selectively engage with one or more discrete locking portions on the handle assembly, and wherein each locking portion corresponds to a degree of stent compression.

9. The stent delivery system of claim 8 wherein the discrete locking portions are longitudinally spaced apart from one another on the handle assembly.

10. The stent delivery system of claim 8 wherein the stent compressor comprises a slider configured to longitudinally translate along portions of the handle assembly.

11. The stent delivery system of claim 1 wherein the handle assembly further comprises a stent compressor in mechanical communication with a first end portion of the stent and independently movable relative to a second end portion of the stent such that movement of the stent compressor is independent of the first and second lead screws and corresponds to axial compression and radial expansion of the stent, and wherein the stent delivery system further comprises:
 a top cap constraining at least the first end portion of the stent; and
 a top cap slider in mechanical communication with the top cap.

12. The stent delivery system of claim 11, further comprising a slider collar selectively coupled to the stent compressor and to the top cap slider such that the top cap is selectively locked in a fixed longitudinal offset from the stent compressor.

13. The stent delivery system of claim 12 wherein the top cap slider is configured to be coupled to the stent compressor.

14. The stent delivery system of claim 1 wherein the stent has a first length in the elongated radially compressed state, and wherein the second lead screw is configured to shorten the stent relative to the first length of the stent by about 50%.

15. The stent delivery system of claim 1 further comprising a delay system configured to delay mechanical communication between the second lead screw and the stent until a predetermined portion of the stent is exposed from the tubular enclosure.

16. The stent delivery system of 15 wherein the second lead screw has a coupler engagement surface, wherein the stent delivery system further comprises a coupler in mechanical communication with the stent, and wherein the coupler has an abutment surface configured to interface with the coupler engagement surface of the second lead screw.

17. The stent delivery system of claim 16 wherein the delay system comprises a longitudinal offset between the abutment surface of the coupler and the coupler engagement surface of the second lead screw.

18. The stent delivery system of claim 1 wherein the second lead screw is configured to be in mechanical communication with a proximal end portion of the stent, wherein, upon rotation of the portion of the housing about the longitudinal axis, the first lead screw pulls the tubular enclosure in a proximal direction and the second lead screw pushes the proximal end portion of the stunt in a distal direction, and wherein translations of the first and second lead screws are configured to control an axial position of a distal end portion of the stent.

19. The stent delivery system of claim 18 wherein the translations of the first and second lead screws are configured to substantially maintain the axial position of the distal end portion of the stent in an aorta.

20. The stent delivery system of claim 1 wherein the second lead screw is configured to be in mechanical communication with a distal end portion of the stent, and wherein, upon rotation of the portion of the housing about the longitudinal axis, the first lead screw pushes the tubular enclosure in a distal direction and the second lead screw pulls the distal end portion of the stent in a proximal direction, and wherein translations of the first and second lead screws are configured to control an axial position of a proximal end portion of the stent.

21. The stent delivery system of claim 20 wherein the translations of the first and second lead screws are configured to substantially maintain the axial position of the proximal end portion of the stent in an iliac artery.

22. The stent delivery system of claim 1 wherein, at an initial position prior to stent deployment, the first and second lead screws longitudinally overlap by at least approximately 7 centimeters.

23. The stent delivery system of claim 1 wherein the tubular enclosure comprises axially-oriented filaments.

24. The stent delivery system of claim 1 wherein the first and second lead screws have an approximately semi-circular cross-section.

25. The stent delivery system of claim 24 wherein at least a portion of each of the first and second lead screws mate along the longitudinal axis to define a lumen.

26. The stent delivery system of claim 24 wherein one of the first and second lead screws defines a longitudinal key slideably engaged with a longitudinal slot on the other of the first and the second lead screws.

27. The stent delivery system of claim 1 wherein the stent comprises a braided frame and a graft cover.

28. The stent delivery system of claim 27 wherein the braided frame comprises nitinol.

29. The stent delivery system of claim 27 wherein the graft cover comprises polyester.

30. The stent delivery system of claim 1 wherein the first lead screw is situated longitudinally adjacent the second lead screw.

31. The stent delivery system of claim 30 wherein each of the first and second lead screws has an inner surface and an opposing threaded curved outer surface configured to engage one of the housing threads,
 wherein the inner surfaces of the first and second lead screws face opposite directions.

32. The stent delivery system of claim 1 wherein the first lead screw and the second lead screw are positioned adjacent each other along the longitudinal axis.

33. The stent delivery system of claim 1 wherein the first and second lead screws each have a threaded outer surface and a cross-section situated radially inwardly from the outer surface, wherein each cross-sections fits entirely on or within a respective sector of a circle, the circle being coincident with a cross-section of the handle assembly.

34. The stent delivery system of claim 1 wherein the first and second lead screws together define an approximately circular cross-section.

35. A handle assembly for delivering a stent from a tubular enclosure, the handle assembly comprising:
 a first lead screw having a first lead thread of a first pitch and a first handedness, the first lead screw having a first screw cross-section situated radially inwardly from the first lead thread, wherein the first lead screw is in mechanical communication with the tubular enclosure;
 a second lead screw having a second lead thread of a second pitch and a second handedness different from the first handedness, and a second screw cross-section situated radially inwardly from the second lead thread, wherein the second lead screw is configured to be placed in mechanical communication with the stent;

wherein the entireties of the first and second lead screw cross-sections each fit on or within a respective sector of a circle, the circle being coincident with a cross-section of the handle assembly;

a housing surrounding at least a portion of each of the first and second lead screws, the housing defining a first housing thread of the first pitch and the first handedness and a second housing thread of the second pitch and the second handedness, wherein, upon rotation of at least a portion of the housing about a longitudinal axis, the first housing thread engages the first lead thread and the second housing thread engages the second lead thread so as to induce simultaneous translations of the first and second lead screws in opposite directions along the longitudinal axis, wherein the translations are configured to deploy the stent from the tubular enclosure.

36. The handle assembly of claim 35, further comprising a stent compressor configured to move a first end portion of the stent independently of and relative to a second end portion of the stent, wherein movement of the stent compressor is independent of the first and second lead screws and corresponds to axial compression and radial expansion of the stent.

37. The handle assembly of claim 36, further comprising a top cap slider in mechanical communication with a top cap constraining at least the first end portion of the stent.

38. The handle assembly of claim 37, further comprising a slider collar selectively coupled to the stent compressor and to the top cap slider such that the top cap is selectively locked at a fixed longitudinal offset from the stent compressor.

39. The handle assembly of claim 37 wherein the top cap slider is coupled to the stent compressor.

40. The handle assembly of claim 35, further comprising a delay system configured to delay mechanical communication between the second lead screw and the stent until the second lead screw has traveled a predetermined delay distance along the longitudinal axis from an initial position to an engagement position.

41. The handle assembly of claim 35 wherein the translations are configured to deploy a distal end of the stent before a proximal end of the stent.

42. The handle assembly of claim 35 wherein the translations are configured to deploy a proximal end of the stent before a distal end of the stent.

43. The stent delivery system of claim 35 wherein the first lead screw is situated longitudinally adjacent the second lead screw.

44. The stent delivery system of claim 43 wherein each of the first and second lead screws has an inner surface and an opposing threaded curved outer surface configured to engage one of the housing threads, wherein the inner surfaces of the first and second lead screws face opposite directions.

45. The stent delivery system of claim 35 wherein the housing has a bore wall surrounding at least a portion of each of the first and second lead screws, the housing bore wall having the first housing thread and the second housing thread thereon, wherein the first and second housing threads intersect on the bore wall.

46. The stent delivery system of claim 35 wherein the first and second screw cross-sections each fit entirely on or within a semi-circle.

47. The stent delivery system of claim 35 wherein the first and second lead screws together define an approximately circular cross-section, with each lead screw defining a portion of the outer circumference of the circular cross-section.

48. A handle assembly for delivering a stent from a tubular enclosure, the handle assembly including:

a first lead screw having a first lead thread with a first handedness, wherein the first lead screw is in mechanical communication with the tubular enclosure;

a second lead screw situated adjacent the first lead screw along a longitudinal axis, wherein the second lead screw has a second lead thread with a second handedness different from the first handedness, the second lead screw being configured to be placed in mechanical communication with the stent;

a housing surrounding at least a portion of each of the first and second lead screws, the housing having an internal first housing thread of the first handedness and an internal second housing thread of the second handedness, wherein the first and second lead screws have adjacently situated lengths within the housing, the first and second lead screws together defining an approximately circular cross-section at their adjacently situated lengths, with each lead screw defining a portion of the outer circumference of the circular cross-section;

wherein, upon rotation of at least a portion of the housing about the longitudinal axis, the first housing thread engages the first lead thread and the second housing thread engages the second lead thread so as to induce simultaneous translations of the first and second lead screws in opposite directions along the longitudinal axis.

49. The stent delivery system of claim 48 wherein the housing has a bore wall surrounding at least a portion of each of the first and second lead screws, the housing bore wall having the first housing thread and the second housing thread thereon, wherein the first and second housing threads intersect on the bore wall.

50. The stent delivery system of claim 48 wherein the first and second lead screws each have a cross-section situated radially inwardly from their respective first and second lead threads, wherein each cross-sections fits entirely on or within a respective sector of a circle, the circle being coincident with a cross-section of the handle assembly.

51. The stent delivery system of claim 48 wherein the first and second lead screws each have a cross-section situated radially inwardly from their respective first and second lead threads, wherein each cross-section fits entirely on or within a semi-circle.

* * * * *